US012269876B2

(12) United States Patent
Kuramochi et al.

(10) Patent No.: US 12,269,876 B2
(45) Date of Patent: Apr. 8, 2025

(54) MODIFIED Fc REGION OF ANTIBODY

(71) Applicant: Chugai Seiyaku Kabushiki Kaisha, Tokyo (JP)

(72) Inventors: Taichi Kuramochi, Shizuoka (JP); Meiri Kawazoe, Shizuoka (JP); Futa Mimoto, Shizuoka (JP); Atsuhiko Maeda, Shizuoka (JP); Tomoyuki Igawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 688 days.

(21) Appl. No.: 16/795,676

(22) Filed: Feb. 20, 2020

(65) Prior Publication Data
US 2020/0181257 A1 Jun. 11, 2020

Related U.S. Application Data

(62) Division of application No. 14/377,556, filed as application No. PCT/JP2013/053011 on Feb. 8, 2013, now abandoned.

(30) Foreign Application Priority Data

Feb. 9, 2012 (JP) ................. 2012-026371

(51) Int. Cl.
C12P 21/06 (2006.01)
C07K 16/00 (2006.01)
C07K 16/28 (2006.01)
C07K 16/30 (2006.01)

(52) U.S. Cl.
CPC ............. *C07K 16/28* (2013.01); *C07K 16/00* (2013.01); *C07K 16/2866* (2013.01); *C07K 16/303* (2013.01); *C07K 2317/52* (2013.01); *C07K 2317/524* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,074,642 A | 6/2000 | Wang et al. | |
| 6,737,056 B1 | 5/2004 | Presta | |
| 7,662,925 B2 | 2/2010 | Lazar et al. | |
| 7,951,917 B1 | 5/2011 | Arathoon et al. | |
| 8,188,231 B2 | 5/2012 | Lazar et al. | |
| 8,329,867 B2 | 12/2012 | Lazar et al. | |
| 8,524,867 B2 | 9/2013 | Bernett et al. | |
| 8,562,991 B2 | 10/2013 | Igawa et al. | |
| 8,592,562 B2 | 11/2013 | Kannan et al. | |
| 8,802,823 B2 | 8/2014 | Lazar et al. | |
| 9,029,515 B2 | 5/2015 | Pons et al. | |
| 9,051,373 B2 | 6/2015 | Lazar et al. | |
| 9,079,949 B1 | 7/2015 | Andrien et al. | |
| 9,200,060 B2 | 12/2015 | Kannan et al. | |
| 9,765,135 B2 | 9/2017 | Ruike | |
| 9,890,218 B2 | 2/2018 | Mimoto et al. | |
| 9,890,377 B2 | 2/2018 | Igawa et al. | |
| 9,969,800 B2 | 5/2018 | Igawa et al. | |
| 10,000,560 B2 | 6/2018 | Ruike et al. | |
| 10,024,867 B2 | 7/2018 | Igawa | |
| 10,253,100 B2 | 4/2019 | Igawa et al. | |
| 10,618,965 B2 | 4/2020 | Igawa et al. | |
| 10,766,960 B2 | 9/2020 | Igawa et al. | |
| 10,919,953 B2 | 2/2021 | Katada et al. | |
| 11,718,678 B2 | 8/2023 | Igawa et al. | |
| 11,827,699 B2 | 11/2023 | Igawa et al. | |
| 2004/0110226 A1 | 6/2004 | Lazar et al. | |
| 2004/0191265 A1 | 9/2004 | Schenerman et al. | |
| 2005/0054832 A1 | 3/2005 | Lazar et al. | |
| 2005/0260213 A1 | 11/2005 | Koenig et al. | |
| 2006/0134709 A1 | 6/2006 | Stavenhagen et al. | |
| 2006/0275282 A1 | 12/2006 | Moore et al. | |
| 2006/0275283 A1 | 12/2006 | Van Vlijmen et al. | |
| 2007/0009523 A1 | 1/2007 | Presta | |
| 2007/0148164 A1 | 6/2007 | Farrington et al. | |
| 2007/0224188 A1 | 9/2007 | Allan et al. | |
| 2007/0231329 A1 | 10/2007 | Lazar et al. | |
| 2007/0237767 A1 | 10/2007 | Lazar et al. | |

(Continued)

FOREIGN PATENT DOCUMENTS

CA 2 721 052 10/2009
CA 2 815 266 5/2012

(Continued)

OTHER PUBLICATIONS

U.S. Appl. No. 14/347,034, Igawa et al., filed Mar. 25, 2014.

(Continued)

*Primary Examiner* — Chun W Dahle

(74) *Attorney, Agent, or Firm* — Fish & Richardson P.C.

(57) ABSTRACT

Polypeptides with improved stability as compared to that of a parent polypeptide were successfully obtained by modifying at least one amino acid in a loop region of the antibody Fc region. Furthermore, by combining multiple amino acid modifications in the loop region, polypeptides with maintained or enhanced FcγR-binding activity as well as improved thermal stability, polypeptides with decreased FcγR-binding activity as well as improved thermal stability, and polypeptides with not only improved thermal stability and adjusted FcγR-binding activity but also decreased aggregate content, as compared to those of a parent polypeptide, were successfully obtained.

13 Claims, 6 Drawing Sheets

Specification includes a Sequence Listing.

(56) References Cited

U.S. PATENT DOCUMENTS

| | | |
|---|---|---|
| 2007/0253951 A1 | 11/2007 | Ng et al. |
| 2008/0051563 A1 | 2/2008 | Lazar et al. |
| 2008/0089892 A1 | 4/2008 | Allan et al. |
| 2009/0041770 A1 | 2/2009 | Chamberlain et al. |
| 2009/0042291 A1 | 2/2009 | Chu et al. |
| 2009/0053211 A9* | 2/2009 | Lazar .................. C07K 16/2893 530/387.3 |
| 2009/0053240 A1 | 2/2009 | Lazar et al. |
| 2009/0076251 A1 | 3/2009 | Koenig et al. |
| 2009/0087478 A1 | 4/2009 | Hansen et al. |
| 2009/0136485 A1 | 5/2009 | Chu et al. |
| 2009/0163699 A1 | 6/2009 | Chamberlain et al. |
| 2009/0324589 A1 | 12/2009 | Igawa et al. |
| 2010/0098730 A1 | 4/2010 | Lowman et al. |
| 2010/0249482 A1 | 9/2010 | Chung et al. |
| 2010/0331527 A1 | 12/2010 | Davis et al. |
| 2011/0021755 A1 | 1/2011 | Lazar et al. |
| 2011/0076275 A1 | 3/2011 | Igawa et al. |
| 2011/0111406 A1 | 5/2011 | Igawa et al. |
| 2011/0229489 A1 | 9/2011 | Pons et al. |
| 2011/0301331 A1* | 12/2011 | Glaser .................... G16B 15/00 435/254.2 |
| 2012/0009188 A1 | 1/2012 | Behrens et al. |
| 2012/0070446 A1 | 3/2012 | Beaumont et al. |
| 2012/0149876 A1 | 6/2012 | Kreudenstein et al. |
| 2012/0244578 A1 | 9/2012 | Kannan et al. |
| 2013/0011866 A1 | 1/2013 | Igawa et al. |
| 2013/0030156 A1 | 1/2013 | Apostolou et al. |
| 2013/0052196 A1 | 2/2013 | Apostolou et al. |
| 2013/0131319 A1 | 5/2013 | Igawa et al. |
| 2013/0209457 A1 | 8/2013 | Lazar et al. |
| 2013/0303396 A1 | 11/2013 | Igawa et al. |
| 2014/0093496 A1 | 4/2014 | Mimoto et al. |
| 2014/0105889 A1 | 4/2014 | Igawa et al. |
| 2014/0112883 A1 | 4/2014 | Ponath et al. |
| 2014/0199294 A1 | 7/2014 | Mimoto et al. |
| 2014/0234340 A1 | 8/2014 | Igawa et al. |
| 2014/0255398 A1 | 9/2014 | Igawa et al. |
| 2014/0335089 A1 | 11/2014 | Igawa et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0344570 A1 | 12/2015 | Igawa et al. |
| 2015/0353630 A1 | 12/2015 | Igawa et al. |
| 2016/0200807 A1 | 7/2016 | Ruike et al. |
| 2016/0229908 A1* | 8/2016 | Igawa ...................... A61P 1/04 |
| 2016/0229915 A1 | 8/2016 | Igawa et al. |
| 2016/0244526 A1 | 8/2016 | Igawa et al. |
| 2017/0022270 A1 | 1/2017 | Igawa et al. |
| 2017/0226206 A1 | 8/2017 | Igawa et al. |
| 2017/0355756 A1 | 12/2017 | Julien et al. |
| 2018/0155451 A1 | 6/2018 | Mimoto et al. |
| 2018/0282718 A1 | 10/2018 | Igawa et al. |
| 2019/0185557 A1 | 6/2019 | Igawa et al. |
| 2019/0233525 A1 | 8/2019 | Igawa et al. |
| 2020/0199241 A1 | 6/2020 | Igawa et al. |
| 2023/0020377 A1 | 1/2023 | Katada et al. |
| 2023/0140797 A1 | 5/2023 | Igawa et al. |
| 2023/0174655 A1 | 6/2023 | Mimoto et al. |
| 2023/0220083 A1 | 7/2023 | Igawa et al. |
| 2023/0257470 A1 | 8/2023 | Igawa et al. |
| 2023/0416371 A1 | 12/2023 | Katada et al. |
| 2024/0043515 A1 | 2/2024 | Katada et al. |
| 2024/0117059 A1 | 4/2024 | Igawa et al. |
| 2024/0279325 A1 | 8/2024 | Igawa et al. |

FOREIGN PATENT DOCUMENTS

| | | |
|---|---|---|
| CA | 2 831 770 | 10/2012 |
| CN | 1291198 | 4/2001 |
| CN | 1763097 | 4/2006 |
| CN | 1867583 | 11/2006 |
| CN | 101014619 | 8/2007 |
| CN | 101098890 | 1/2008 |
| CN | 102056946 | 5/2011 |
| CN | 103827300 | 5/2014 |
| EP | 0 091 539 A | 10/1983 |
| EP | 2 194 066 | 6/2010 |
| EP | 2 196 541 | 6/2010 |
| EP | 2 206 775 A | 7/2010 |
| EP | 2 275 443 | 1/2011 |
| EP | 2 314 618 | 4/2011 |
| EP | 2 366 713 | 9/2011 |
| EP | 2 647 706 | 10/2013 |
| EP | 2 679 681 A | 1/2014 |
| EP | 2 698 431 | 2/2014 |
| EP | 2 728 002 | 5/2014 |
| EP | 2 940 135 | 11/2015 |
| JP | H01-144991 | 6/1989 |
| JP | H02-501112 | 4/1990 |
| JP | H02-163085 | 6/1990 |
| JP | 2003-512019 | 4/2003 |
| JP | 2005-501514 | 1/2005 |
| JP | 2006-512407 | 4/2006 |
| JP | 2006-524039 | 10/2006 |
| JP | 2007-525443 | 9/2007 |
| JP | 2007-532139 | 11/2007 |
| JP | 2008-510466 | 4/2008 |
| JP | 2008-511292 | 4/2008 |
| JP | 2008-519860 | 6/2008 |
| JP | 2009-511067 | 3/2009 |
| JP | 2010-079667 | 3/2010 |
| JP | 2010-250830 | 11/2010 |
| JP | 2011-507963 | 3/2011 |
| JP | 2011-184418 | 9/2011 |
| JP | 2012-505833 | 3/2012 |
| JP | 2014-528906 | 10/2014 |
| JP | 6433297 | 12/2018 |
| RU | 2236222 | 9/2004 |
| RU | 2005/112742 | 1/2006 |
| RU | 2006/142852 | 6/2008 |
| RU | 2007/121679 | 12/2008 |
| RU | 2367667 | 9/2009 |
| RU | 2390527 | 5/2010 |
| RU | 2398777 | 9/2010 |
| SG | 183867 | 10/2012 |
| TW | 2010/00127 | 1/2010 |
| TW | 2011/16625 | 5/2011 |
| WO | WO 88/04692 | 6/1988 |
| WO | WO 95/02187 | 1/1995 |
| WO | WO 95/29697 | 11/1995 |
| WO | WO 97/34631 | 9/1997 |
| WO | WO 99/40117 | 8/1999 |
| WO | WO 99/58572 | 11/1999 |
| WO | WO 00/15214 | 3/2000 |
| WO | WO 00/42072 | 7/2000 |
| WO | WO 02/60919 | 8/2002 |
| WO | WO 03/057881 | 7/2003 |
| WO | WO 03/105757 | 12/2003 |
| WO | WO 03/107009 | 12/2003 |
| WO | WO 2004/007553 | 1/2004 |
| WO | WO 2004/029207 | 4/2004 |
| WO | WO 2004/035752 | 4/2004 |
| WO | WO 2004/039826 | 5/2004 |
| WO | WO 2004/063351 | 7/2004 |
| WO | WO 2004/092219 | 10/2004 |
| WO | WO 2004/099249 | 11/2004 |
| WO | WO 2005/037867 | 4/2005 |
| WO | WO 2005/056606 | 6/2005 |
| WO | WO 2005/059106 | 6/2005 |
| WO | WO 2005/070963 | 8/2005 |
| WO | WO 2005/077981 | 8/2005 |
| WO | WO 2005/115452 | 12/2005 |
| WO | WO 2005/123780 | 12/2005 |
| WO | WO 2006/015371 | 2/2006 |
| WO | WO 2006/019447 | 2/2006 |
| WO | WO 2006/020114 | 2/2006 |
| WO | WO 2006/023403 | 3/2006 |
| WO | WO 2006/023420 | 3/2006 |

(56) References Cited

FOREIGN PATENT DOCUMENTS

| | | |
|---|---|---|
| WO | WO 2006/031370 | 3/2006 |
| WO | WO 2006/036291 | 4/2006 |
| WO | WO 2006/050166 | 5/2006 |
| WO | WO 2006/053301 | 5/2006 |
| WO | WO 2006/071877 | 7/2006 |
| WO | WO 2006/076594 | 7/2006 |
| WO | WO 2006/085938 | 8/2006 |
| WO | WO 2006/088494 | 8/2006 |
| WO | WO 2006/105338 | 10/2006 |
| WO | WO 2006/106905 | 10/2006 |
| WO | WO 2006/116260 | 11/2006 |
| WO | WO 2006/130834 | 12/2006 |
| WO | WO 2006/133486 | 12/2006 |
| WO | WO 2007/021841 | 2/2007 |
| WO | WO 2007/022520 | 2/2007 |
| WO | WO 2007/024249 | 3/2007 |
| WO | WO 2007/041635 | 4/2007 |
| WO | WO 2007/047578 | 4/2007 |
| WO | WO 2007/084253 | 7/2007 |
| WO | WO 2007/092772 | 8/2007 |
| WO | WO 2007/114325 | 10/2007 |
| WO | WO 2008/022152 | 2/2008 |
| WO | WO 2008/068048 A2 | 6/2008 |
| WO | WO 2008/092117 | 7/2008 |
| WO | WO 2008/134046 | 11/2008 |
| WO | WO 2008/143954 | 11/2008 |
| WO | WO 2008/150494 | 12/2008 |
| WO | WO 2009/041062 | 4/2009 |
| WO | WO 2009/041643 | 4/2009 |
| WO | WO 2009/053358 | 4/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/139822 | 11/2009 |
| WO | WO 2010/015608 | 2/2010 |
| WO | WO 2010/035769 | 4/2010 |
| WO | WO 2010/045193 | 4/2010 |
| WO | WO 2010/058860 | 5/2010 |
| WO | WO 2010/081173 | 7/2010 |
| WO | WO 2010/085682 | 7/2010 |
| WO | WO-2010085682 A2 * | 7/2010 ............ C07K 16/00 |
| WO | WO 2010/106180 | 9/2010 |
| WO | WO 2010/106812 | 9/2010 |
| WO | WO 2010/107109 | 9/2010 |
| WO | WO 2010/151792 | 12/2010 |
| WO | WO 2011/043643 | 4/2011 |
| WO | WO 2011/044368 | 4/2011 |
| WO | WO 2011/091177 | 7/2011 |
| WO | WO 2011/091181 | 7/2011 |
| WO | WO 2011/107989 | 9/2011 |
| WO | WO 2011/111007 | 9/2011 |
| WO | WO 2011/122011 | 10/2011 |
| WO | WO 2012/033953 | 3/2012 |
| WO | WO 2012/058768 | 5/2012 |
| WO | WO 2012/073992 | 6/2012 |
| WO | WO 2012/115241 | 8/2012 |
| WO | WO 2012/125850 | 9/2012 |
| WO | WO 2012/132067 | 10/2012 |
| WO | WO 2012/133782 | 10/2012 |
| WO | WO 2012/145238 | 10/2012 |
| WO | WO 2013/002362 | 1/2013 |
| WO | WO 2013/004842 | 1/2013 |
| WO | WO 2013/046704 | 4/2013 |
| WO | WO 2013/047748 | 4/2013 |
| WO | WO 2013/047752 | 4/2013 |
| WO | WO 2013/063702 | 5/2013 |
| WO | WO 2013/118858 | 8/2013 |
| WO | WO 2014/028354 | 2/2014 |
| WO | WO 2014/104165 | 7/2014 |
| WO | WO 2014/163101 | 10/2014 |
| WO | WO 2016/000813 | 1/2016 |
| WO | WO 2016/098356 | 6/2016 |
| WO | WO 2018/169993 | 9/2018 |
| WO | WO 2021/131021 | 7/2021 |
| WO | WO 2022/044248 A1 | 3/2022 |
| WO | WO 2022/045276 A1 | 3/2022 |
| WO | WO 2022/270611 A1 | 12/2022 |
| WO | WO 2022/270612 A1 | 12/2022 |

OTHER PUBLICATIONS

U.S. Appl. No. 14/347,187, Igawa et al., filed Jul. 25, 2014.
U.S. Appl. No. 15/210,353, Igawa et al., filed Jul. 14, 2016.
U.S. Appl. No. 15/210,360, Igawa et al., filed Jul. 14, 2016.
U.S. Appl. No. 15/230,904, Igawa et al., filed Aug. 8, 2016.
U.S. Appl. No. 15/860,163, Mimoto et al., filed Jan. 2, 2018.
U.S. Appl. No. 15/952,945, Igawa et al., filed Apr. 13, 2018.
U.S. Appl. No. 16/028,140, Igawa et al., filed Jul. 5, 2018.
U.S. Appl. No. 16/264,735, Igawa et al., filed Feb. 1, 2019.
U.S. Appl. No. 61/313,102, Pons et al., filed Mar. 11, 2010.
Alley et al., "Antibody-drug conjugates: targeted drug delivery for cancer," Curr Opin Chem Biol, Aug. 2010,14(4):529-37. doi: 10.1016/j.cbpa.2010.06.170. Epub Jul. 17, 2010.
Akbarzadeh-Sharbaf et al., "In silico design, construction and cloning of Trastuzumab humanized monoclonal antibody: A possible biosimilar for Herceptin," Adv Biomed Res, 2012, 1:21. doi: 10. 4103/ 2277-9175. 98122. Epub Jul. 6, 2012.
Alignment of SEQ ID Nos. 28-32 from WO 2009/125825 (document submitted by Opponents in EPO Opposition Procedure for EP 2 552 955 and posted by EPO on Feb. 2, 2018), 1 page.
Alignment of the amino acid sequences of the Fc regions of the antibodies exemplified in EP 2 275 443 (document submitted by Opponents in EPO Opposition Procedure for EP 2 552 955 and posted by EPO on Feb. 2, 2018), 1 page.
Alignment of variable heavy and light chain amino acid sequences from WO 2009/125825 (document submitted by Opponents in EPO Opposition Procedure for EP 2 552 955 and posted by EPO on Feb. 2, 2018), 2 pages.
Amigorena et al., "Fc gamma RII expression in resting and activated B lymphocytes," Eur J Immunol, 1989, 19(8):1379-85.
Amigorena et al., "Cytoplasmic domain heterogeneity and functions of IgG Fc receptors in B lymphocytes," 1992, Science, 256(5065):1808-12.
www.bioinf.org.uk , "Antibodies," Dr. Andrew C.R. Martin's Group, retrieved on Jul. 17, 2019, URL < http://www.bioinf.org.uk/abs/ >, 9 pages.
Araujo et al., "Increased rheumatoid factor interference observed during immunogenicity assessment of an Fc-engineered therapeutic antibody," J Pharm Biomed Anal., Jul. 15, 2011, 55(5):1041-9. doi: 10.1016/j.jpba.2011.03.008. Epub Mar. 11, 2011.
Armour et al., "Differential binding to human FcgammaRIIa and FcgammaRIIb receptors by human IgG wildtype and mutant antibodies," Mol Immunol, 2003, 40(9):585-93.
Atherton et al., "Acid-base balance: maintenance of plasma pH," Anaesthesia & Intensive Care Medicine, 2009, 10(11):557-61.
Baeuerle et al., "BiTE: Teaching antibodies to engage T-cells for cancer therapy," Curr Opin Mol Ther, 2009, 11(1):22-30.
Beringhelli et al., "pH and ionic strength dependence of protein (un)folding and ligand binding to bovine beta-lactoglobulins A and B," Biochemistry, Dec. 24, 2002, 41(51):15415-22.
Bjellqvist et al., "The focusing positions of polypeptides in immobilized pH gradients can be predicted from their amino acid sequences," Electrophoresis, Oct. 1993, 14(10):1023-31.
Blank et al., "Decreased transcription of the human FCGR2B gene mediated by the −343 G/C promoter polymorphism and association with systemic lupus erythematosus," Hum Genet, 2005, 117(2-3):220-7.
Boruchov et al., "Activating and inhibitory IgG Fc receptors on human DCs mediate opposing functions," J Clin Invest, 2005, 115(10):2914-23.
Boumpas et al., "A short course of BG9588 (anti-CD40 ligand antibody) improves serologic activity and decreases hematuria in patients with proliferative lupus glomerulonephritis," Arthritis Rheum., 2003, 48(3):719-27.

(56) References Cited

OTHER PUBLICATIONS

Brown et al., "Tolerance to Single, but Not Multiple, Amino Acid Replacements in Antibody VHCDR2," J Immunol, May 1, 1996, 156(9):3285-91.
Bruhns et al., "Specificity and affinity of human Fcgamma receptors and their polymorphic variants for human IgG subclasses," Blood, Apr. 16, 2009, 113(16):3716-25. doi: 10.1182/blood-2008-09-179754. Epub Nov. 18, 2008.
Burmeister et al., "Crystal structure of the complex of rat neonatal Fc receptor with Fc," Nature, Nov. 24, 1994, 372(6504):379-83.
Cartron et al., "Therapeutic activity of humanized anti-CD20 monoclonal antibody and polymorphism in IgG Fc receptor FcgammaRIIIa gene," Blood, Feb. 1, 2002, 99(3):754-8.
Cemerski et al., "Suppression of mast cell degranulation through a dual-targeting tandem IgE-IgG Fc domain biologic engineered to bind with high affinity to FcγRIIb," Immunol Lett, 2012, 143(1):34-43.
Chen et al., "Association of a transmembrane polymorphism of Fcgamma receptor IIb (FCGR2B) with systemic lupus erythematosus in Taiwanese patients," Arthritis Rheum, 2006, 54(12):3908-17.
Chu et al., "Reduction of total IgE by targeted coengagement of IgE B-cell receptor and FcγRIIb with Fc-engineered antibody," J Allergy Clin Immunol, 2012, 129(4):1102-15.
Chu et al., "Inhibition of B cell receptor-mediated activation of primary human B cells by coengagement of CD19 and FcgammaRIIb with Fc-engineered antibodies," Mol Immunol, 2008, 45(15):3926-33.
Chuntharapai et al., "Isotype-dependent inhibition of tumor growth in vivo by monoclonal antibodies to death receptor 4," J Immunol, 2001, 166(8):4891-8.
Granted claims of EP 2 275 443 (submitted on May 24, 2019 by the Patentee during EPO Opposition Procedure for EP 2 202 245), 1 page.
Clark, "IgG effector mechanisms," Chem Immunol, 1997, 65:88-110.
Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.
Clynes et al., "Fc receptors are required in passive and active immunity to melanoma," Proc Natl Acad Sci USA, Jan. 20, 1998, 95(2):652-6.
Clynes et al., "Inhibitory Fc receptors modulate in vivo cytotoxicity against tumor targets," Nat Med, Apr. 2000, 6(4):443-6.
Dall'Acqua et al., "Increasing the affinity of a human IgG1 for the neonatal Fc receptor: biological consequences," J Immunol, 2002, 169(9):5171-80.
Dall 'Acqua et al., "Properties of human IgG1s engineered for enhanced binding to the neonatal Fc receptor (FcRn)," J Biol Chem, Aug. 18, 2006, 281(33):23514-24. Epub Jun. 21, 2006.
Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.
Datta-Mannan et al., "Monoclonal antibody clearance. Impact of modulating the interaction of IgG with the neonatal Fc receptor," J Biol Chem, Jan. 19, 2007, 282(3):1709-17. Epub Nov. 29, 2006.
Davda et al., "Properties of a general PK/PD model of antibody-ligand interactions for therapeutic antibodies that bind to soluble endogenous targets," mAbs, Sep.-Oct. 2010, 2(5):576-88. doi: 10.4161/mabs.2.5.12833. Epub Sep. 1, 2010.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel, Apr. 2010, 23(4):195-202. doi: 10.1093/protein/gzp094. Epub Feb. 4, 2010.
Davydov, "Omalizuman (Xolair) for Treatment of Asthma," Am Fam Physician, Jan. 15, 2005, 71(2):341-2.
De Bono et al., "ING-1, a monoclonal antibody targeting Ep-CAM in patients with advanced adenocarcinomas," Clin Cancer Res, 2004, 10(22):7555-65.
Declaration of Nimish Gera, Ph.D., CV and Exhibits, dated Sep. 1, 2016 (submitted in an opposition to EP 2 275 443), 24 pages.
De Felice et al., "Formation of amyloid aggregates from human lysozyme and its disease-associated variants using hydrostatic pressure," FASEB J, Jul. 2004, 18(10):1099-101. (doi:10.1096/fj.03-1072fje; PMID 15155566).
Demarest et al., "Optimization of the antibody C(H)3 domain by residue frequency analysis of IgG sequences," J Mol Biol, Jan. 2, 2004, 335(1):41-8.
Deng et al., "Pharmacokinetics of humanized monoclonal anti-tumor necrosis factor-α antibody and its neonatal Fc receptor variants in mice and cynomolgus monkeys," Drug Metab Dispos, Apr. 2010, 38(4):600-5. doi: 10.1124/dmd.109.031310. Epub Jan. 13, 2010.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Dhodapkar et al., "Selective blockade of inhibitory Fcgamma receptor enables human dendritic cell maturation with IL-12p70 production and immunity to antibody-coated tumor cells," Proc Natl Acad Sci USA, 2005, 102(8):2910-5.
Duffau et al., "Platelet CD154 potentiates interferon-alpha secretion by plasmacytoid dendritic cells in systemic lupus erythematosus," Sci Transl Med, 2010, 2(47):47ra63.
Dufner et al., "Harnessing phage and ribosome display for antibody optimisation," Trends Biotechnol, Nov. 2006, 24(11):523-9.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
EMA product information: Annexes to file of the tocilizumab preparation RoActemra (WC500054890), published Jan. 8, 2010, 109 pages.
Epstein, "Non-randomness of amino-acid changes in the evolution of homologous proteins," Nature, Jul. 22, 1967, 215(5099):355-9.
Expert Declaration by Dr. Madhusudan Natarajan, Feb. 5, 2018 (document submitted by Opponents in EPO Opposition Procedure for EP 2 552 955 and posted by EPO on Feb. 5, 2018).
Experimental data characterizing the binding of rituximab to its antigen CD20 and to human FcRn, (document submitted by Opponents in EPO Opposition Procedure for EP 2 552 955 and posted by EPO on Feb. 2, 2018), 6 pages.
Fillipovic, Biochemical Fundamentals of Human Vital Activity, VLADOS, 2005, pp. 38-43 (with English translation).
Fillipovich, Biochemical basis of human life, VLADOS, 2005, pp. 49-50 (with English translation).
Floto et al., "Loss of function of a lupus-associated FcgammaRIIb polymorphism through exclusion from lipid rafts," Nat Med, 2005, 11(10):1056-8.
Fournier et al., "Activation of human peripheral IgM+ B cells is transiently inhibited by BCR-independent aggregation of Fc gammaRIIB," J Immunol, 2008, 181(8):5350-9.
Gaza-Bulseco et al., "Fragmentation of a recombinant monoclonal antibody at various pH," Pharm Res, Aug. 2008, 25(8):1881-90. doi: 10.1007/s11095-008-9606-3. Epub May 13, 2008.
Ghetie et al., "Increasing the serum persistence of an IgG fragment by random mutagenesis," Nat Biotechnol, 1997, 15(7):637-40.
Goebl et al., "Neonatal Fc Receptor Mediates Internalization of Fc Transfected Human Endothelial Cells," Molecular Biology of the Cell, Dec. 2008, 19(12):5490-5505. doi: 10.1091/mbc.E07-02-0101. Epub Oct. 8, 2008.
Goel et al., "Plasticity within the Antigen-Combining Site May Manifest as Molecular Mimicry in the Humoral Immune Response," J Immunol, Dec. 15, 2004, 173(12):7358-67.
Gong et al., "Engineered human antibody constant domains with increased stability," J Biol Chem, May 22, 2009, 284(21):14203-10. doi: 10.1074/jbc.M900769200. Epub Mar. 23, 2009.
Greenwood et al., "Structural motifs involved in human IgG antibody effector functions," Eur J Immunol., 1993, 23(5):1098-104.

(56) References Cited

OTHER PUBLICATIONS

Gunasekaran et al., "Enhancing Antibody Fc Heterodimer Formation through Electrostatic Steering Effects," J Biol Chem, Jun. 18, 2010, 285(25):19637-46. doi:10.1074/jbc.M110.117382.Epub Apr. 16, 2010.

Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.

Hamilton, "Molecular engineering: applications to the clinical laboratory," Clin Chem, 1993, 39(9):1988-97.

Hanson et al., "Catalytic antibodies and their applications," Curr Opin Biotechnol, 2005, 16:631-636.

Haringman et al., "A randomized controlled trial with an anti-CCL2 (anti-monocyte chemotactic protein 1) monoclonal antibody in patients with rheumatoid arthritis," Arthritis Rheum, 2006, 54(8):2387-92.

Heyman, "Feedback regulation by IgG antibodies," Immunol Lett, 2003, 88(2):157-61.

Hinton et al., "An engineered human IgG1 antibody with longer serum half-life," J Immunol, 2006, 176(1):346-56.

Hinton et al., "Engineered Human IgG Antibodies with Longer Serum Half-lives in Primates," J Biol Chem, Feb. 20, 2004, 279(8):6213-6. Epub Dec. 29, 2003.

Horton et al., "Potent in vitro and in vivo activity of an Fc-engineered anti-CD19 monoclonal antibody against lymphoma and leukemia," Cancer Res, Oct. 1, 2008, 68(19):8049-57. doi: 10.1158/0008-5472. CAN-08-2268.

Igawa et al., "Engineering the variable region of therapeutic IgG antibodies," mAbs, May-Jun. 2011, 3(3):243-52. Epub May 1, 2011.

Igawa et al., "Antibody recycling by engineered pH-dependent antigen binding improves the duration of antigen neutralization," Nat Biotechnol, 2010, 28(11):1203-7.

Igawa et al., "Reduced elimination of IgG antibodies by engineering the variable region," Protein Eng Des Sel, 2010, 23(5):385-92.

Igawa et al., "Antibody optimization technologies for developing next generation antibody therapeutics," Bio Industry, 2011, 28(7):15-21 (with English translation).

Information Meeting on Antibody Engineering Technologies, Copyright © Chugai Pharmaceutical Co., Ltd., Dec. 18, 2012, 1 page.

Irani et al., "Molecular properties of human IgG subclasses and their implications for designing therapeutic monoclonal antibodies against infectious diseases," Mol Immunol, Oct. 2015, 67(2 Pt A):171-82. doi : 10. 1016/ j. molimm. 2015. 03. 255. Epub Apr. 18, 2015.

Ishii et al., "FcRn, a critical regulator of antibody pharmacokinetics," Folia Pharmacol Jpn, 2010, 136(5):280-284 (with English translation).

Ito et al., "The His-probe method: effects of histidine residues introduced into the complementarity-determining regions of antibodies on antigen-antibody interactions at different pH values," FEBS Lett, 1992, 309:85-88.

Jaeger, Clinical Immunology and Allergology, M.: Medicina, 1990, 2:484-5 (with English translation).

Janeway et al., Immunobiology, The Immune System in Health and Disease, 3$^{rd}$ Edition, 1997 Garland Publishing Inc., pp. 3:1-3:11.

Jefferis et al., "Interaction sites on human IgG-Fc for FcgammaR: current Models," Immunol Lett, 2002, 82(1-2):57-65.

Juszczak et al., "Ipilimumab: a novel immunomodulating therapy causing autoimmune hypophysitis: a case report and review," Eur J Endocrinol, Jul. 2012, 167(1):1-5. doi: 10.1530/EJE-12-0167. Epub Apr. 10, 2012.

Kabat et al., "Sequences of proteins of immunological interest," U.S. Department of Health and Human Services, National Institutes of Health, NIH Publication No. 91-3242, 5th ed., 1991, vol. 1, pp. 679-687.

Kamei et al., "Quantitative methods for developing Fc mutants with extended half-lives," Biotechnol Bioeng, Dec. 20, 2005, 92(6):748-60.

Kim et al., "Antibody Engineering for the Development of Therapeutic Antibodies," Mol Cells, 2005, 20:17-29.

King, Applications and Engineering of Monoclonal Antibodies, 1998, pp. 68-71.

Kohrt et al., "Stimulation of natural killer cells with a CD137-specific antibody enhances trastuzumab efficacy in xenotransplant models of breast cancer," J Clin Invest, 2012, 122(3):1066-75.

Lazar et al., "Engineered antibody Fc variants with enhanced effector function," Proc Natl Acad Sci USA, Mar. 2006, 103(11):4005-10. Epub Mar. 6, 2006.

Lewis et al., "Differential responses of human tumor cell lines to anti-p185HER2 monoclonal antibodies," Cancer Immunol Immunother, 1993, 37(4):255-63.

Li et al., "Inhibitory Fcγ receptor engagement drives adjuvant and anti-tumor activities of agonistic CD40 antibodies," Science, 2011, 333(6045):1030-4.

Li et al., "CD72 down-modulates BCR-induced signal transduction and diminishes survival in primary mature B lymphocytes," J Immunol, 2006, 176(9):5321-8.

Liang et al., "Immunity against a therapeutic xenoprotein/Fc construct delivered by gene transfer is reduced through binding to the inhibitory receptor FcγRIIb," J Gene Med, 2011, 13(9):470-7.

Liu et al., "Effect of posttranslational modifications on the thermal stability of a recombinant monoclonal antibody," Immunol Lett, Aug. 15, 2006, 106(2):144-53. Epub Jun. 27, 2006.

Liu et al., "Asymmetrical Fc engineering greatly enhances antibody-dependent cellular cytotoxicity (ADCC) effector function and stability of the modified antibodies," J Biol Chem, Feb. 7, 2014, 289(6):3571-90. doi: 10.1074/jbc.M113.513366. Epub Dec. 5, 2013.

Lloyd et al., "Modelling the human immune response: performance of a 1011 human antibody repertoire against a broad panel of therapeutically relevant antigens," Protein Eng Des Sel, Mar. 2009, 22(3):159-68. doi: 10.1093/protein/gzn058. Epub Oct. 29, 2008.

Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107. Epub Jun. 28, 2010.

Luttrell et al., "Reaction coupling of chelation and antigen binding in the calcium ion-dependent antibody binding of cyclic AMP," J Biol Chem, Nov. 15, 1991, 266(32):21626-30.

Mackay et al., "Selective dysregulation of the FcgammaIIB receptor on memory B cells in SLE," J Exp Med., 2006, 203(9):2157-64.

Manger et al., "Fcgamma receptor IIa polymorphism in Caucasian patients with systemic lupus erythematosus: association with clinical symptoms," Arthritis Rheum, 1998, 41(7):1181-9.

Martin et al., "Preclinical safety and immune-modulating effects of therapeutic monoclonal antibodies to interleukin-6 and tumor necrosis factor-α in cynomolgus macaques," J Immunotoxicol, Jul. 1, 2004, 1(3):131-9. doi: 10.1080/15476910490894904.

Marvin et al., "Recombinant approaches to IgG-like bispecific antibodies," Acta Pharmacol Sin, Jun. 2005, 26(6):649-58.

Meyer et al., "Bevacizumab immune complexes activate platelets and induce thrombosis in FCGR2A transgenic mice," J Thromb Haemost, Jan. 2009, 7(1):171-81. Epub Oct. 30, 2008.

Mi et al., "Targeting the neonatal fc receptor for antigen delivery using engineered fc fragments," J Immunol, 2008, 181(11):7550-61.

Mimoto et al., "Novel asymmetrically engineered antibody Fc variant with superior FcγR binding affinity and specificity compared with afucosylated Fc variant," mAbs, Mar.-Apr. 2013, 5(2):229-36. doi: 10.4161/mabs.23452. Epub Feb. 13, 2013.

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-9.

Morgan et al., "The N-terminal end of the CH2 domain of chimeric human IgGI anti-HLA-DR is necessary for C1q, Fc gamma RI and Fc gamma RIII binding," Immunology, 1995, 86(2):319-24.

Muta et al., "A 13-amino-acid motif in the cytoplasmic domain of Fc gamma RIIB modulates B-cell receptor signaling," Nature, 1994, 368(6466):70-3.

Nakamura et al., "Fcgamma receptor IIB-deficient mice develop Goodpasture's syndrome upon immunization with type IV collagen: a novel murine model for autoimmune glomerular basement membrane disease," J Exp Med, 2000, 191(5):899-906.

(56) References Cited

OTHER PUBLICATIONS

Nam et al., "Current evidence for the management of rheumatoid arthritis with biological disease-modifying antirheumatic drugs: a systematic literature review informing the EULAR recommendations for the management of RA," Ann Rheum Dis, Jun. 2010, 69(6):976-86. doi: 10.1136/ard.2009.126573. Epub May 6, 2010.
Nicholas et al., "Regulation of the immune response. I. Reduction in ability of specific antibody to inhibit long-lasting IgG immunological priming after removal of the Fc fragment," J Exp Med, 1969, 129(6):1183-201.
Niebecker et al., "Safety of therapeutic monoclonal antibodies," Curr Drug Saf, 2010, 5(4):275-86.
Nimmerjahn et al., "Fcgamma receptors as regulators of immune responses," Nat Rev Immunol, 2008, 8(1):34-47.
Nimmerjahn et al., "Divergent immunoglobulin g subclass activity through selective Fc receptor binding," Science, Dec. 2, 2005, 310(5753):1510-2.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008, 112(10):3959-64. doi: 10.1182/blood-2008-05-155846. Epub Sep. 10, 2008.
O'Donovan et al., "EGFR and HER-2 Antagonists in Breast Cancer," Anticancer Res, May-Jun. 2007, 27(3A):1285-94.
Experimental data regarding Off-rate of Xolair Fab for binding to human lgE at pH7.4 and pH5.5 (document submitted by Opponents in EPO Opposition Procedure for EP 2 552 955 and posted by EPO on Feb. 2, 2018), 6 pages.
EP Communication dated Oct. 13, 2016, in EP Application No. 11714860. 1, issued during examination of the opposed patent, 3 pages.
Oganesyan et al., "Structural characterization of a mutated, ADCC-enhanced human Fc fragment," Mol Immunol, 2008, 45(7):1872-82.
Oganesyan et al., "Structural characterization of a human Fc fragment engineered for lack of effector functions," Acta Crystallogr D Biol Crystallogr, 2008, 64(Pt 6):700-4. doi: 10.1107/S0907444908007877. Epub May 14, 2008.
Okabe, "Proprietary Innovative Antibody Engineering Technologies in Chugai Pharmaceutical," Information meeting on Antibody Engineering Technologies, Dec. 18, 2012, 78 pages.
Olferiev et al., "The role of activating protein 1 in the transcriptional regulation of the human FCGR2B promoter mediated by the -343 G-> C polymorphism associated with systemic lupus erythematosus," J Biol Chem, 2007, 282(3):1738-46.
Pakula et al., "Genetic Analysis of Protein Stability and Function," Annu Rev Genet, 1989, 23:289-310.
Patton et al., "An acid dissociation bridging ELISA for detection of antibodies directed against therapeutic proteins in the presence of antigen," J Immunol Methods, Sep. 2005, 304(1-2):189-95.
Pavlou et al., "The therapeutic antibodies market to 2008," Eur J Pharm Biopharm, 2005, 59(3):389-396.
Petkova et al., "Enhanced half-life of genetically engineered human IgG1 antibodies in a humanized FcRn mouse model: potential application in humorally mediated autoimmune disease," Int Immunol, Dec. 2006, 18(12):1759-69. Epub Oct. 31, 2006.
Popov et al., "The Stoichiometry and Affinity of the Interaction of Murine Fc Fragments with the MHC Class I-Related Receptor, FcRn," Mol Immunol, Apr. 1996, 33(6):521-30.
Presta, "Molecular engineering and design of therapeutic antibodies," Curr Opin Immunol, Aug. 2008, 20(4):460-70. doi : 10.1016/j.coi.2008. 06.012.
Presta at el., "Humanization of an Anti-Vascular Endothelial Growth Factor Monoclonal Antibody for the Therapy of Solid Tumors and Other Disorders," Cancer Res, Oct. 15, 1997, 57(20):4593-9.
Product labelling information for Rituxan (Rituximab), dated Nov. 1997.
Properties of human lgG subclasses, Feb. 28, 2017, http://ednieuw.home. xs4al l.nl/lgGsubclasses/subk123.htm, 5 pages.

Qiao et al., "Dependence of antibody-mediated presentation of antigen on FcRn," Proc Natl Acad Sci USA, 2008, 105(27):9337-42.
Radaev et al., "The role of Fc glycosylation and the binding of peptide inhibitors," J Biol Chem, May 11, 2001, 276(19):16478-83. Epub Jan. 31, 2001.
Radaev et al., "The structure of a human type III Fcgamma receptor in complex with Fc," J Biol Chem, May 11, 2001, 276(19):16469-77. Epub Jan. 31, 2001.
Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-57.
Rajpal et al., A general method for greatly improving the affinity of antibodies by using combinatorial libraries, Proc Natl Acad Sci USA, 2005, 102:8466-71.
Raju et al., "Glycosylation in the Fc domain of IgG increases resistance to proteolytic cleavage by papain," Biochem Biophys Res Commun, Mar. 17, 2006, 341(3):797-803. Epub Jan. 19, 2006.
Rathanaswami et al., "Demonstration of an in vivo generated sub-picomolar affinity fully human monoclonal antibody to interleukin-8," Biochem Biophys Res Commun, 2005, 334:1004-13.
Ravetch et al., "Immune inhibitory receptors," Science, 2000, 290(5489):84-9.
Reichert et al., "Monoclonal antibody successes in the clinic," Nat Biotechnol, 2005, 23(9):1073-78.
Remmele et al., "Active dimer of Epratuzumab provides insight into the complex nature of an antibody aggregate," J Pharm Sci, 2006, 95(1):126-45.
Reverberi et al., "Factors affecting the antigen-antibody reaction," Blood Transfus, Nov. 2007, 5(4):227-40. doi: 10.2450/2007.0047-07.
Richards et al., "Optimization of antibody binding to FcgammaRIIa enhances macrophage phagocytosis of tumor cells," Mol Cancer Ther, 2008, 7(8):2517-27.
Riechelmann et al., "Phase I trial with the CD44v6-targeting immunoconjugate bivatuzumab mertansine in head and neck squamous cell carcinoma," Oral Oncol, Sep. 2008, 44(9):823-9. doi: 10.1016/j.oraloncology.2007.10.009. Epub Jan. 18, 2008.
Robles-Carrillo et al., "Anti-CD40L immune complexes potently activate platelets in vitro and cause thrombosis in FCGR2A transgenic mice," J Immunol, 2010, 185(3):1577-83.
Roitt et al., Immunology, M., Mir, 2000, pp. 373-374 (with English translation).
Roitt et al., Immunology, M., Mir, 2000, pp. 97-113 (in Russian, with what is believed to be a published English equivalent of those pages).
Roopenian et al., "FcRn: the neonatal Fc receptor comes of age," Nat Rev Immunol, Sep. 2007, 7(9):715-25. Epub Aug. 17, 2007.
Rosenberg, "Effects of protein aggregates: an immunologic perspective," AAPS J, 2006, 8(3):E501-7.
Rudikoff et al., "Single amino acid substitution altering antigen-binding specificity," Proc Natl Acad Sci USA, Mar. 1982, 79(6):1979-83.
Salmon et al., "Fc gamma RIIA alleles are heritable risk factors for lupus nephritis in African Americans," J Clin Invest, 1996, 97(5):1348-54.
Samuelsson et al., "Anti-inflammatory activity of IVIG mediated through the inhibitory Fc receptor," Science, Jan. 19, 2001, 291(5503):484-6.
Satoh et al., "Non-fucosylated therapeutic antibodies as next-generation therapeutic antibodies," Expert Opin Biol Ther, 2006, 6(11):1161-73.
Scappaticci et al., "Arterial thromboembolic events in patients with metastatic carcinoma treated with chemotherapy and bevacizumab," J Natl Cancer Inst, 2007, 99(16):1232-9.
Schuster et al., "Signaling of human ciliary neurotrophic factor (CNTF) revisited. The interleukin-6 receptor can serve as an alpha-receptor for CTNF," J Biol Chem, Mar. 14, 2003, 278(11):9528-35.
Seda et al., "B-cell receptor signalling and its crosstalk with other pathways in normal and malignant cells," Eur J Haematol, Aug. 1, 2014, 94:193-205. doi: 10.1111/ejh.12427.
Shields et al., "High resolution mapping of the binding site on human IgG1 for Fc gamma RI, Fc gamma RII, Fc gamma RIII, and

(56) References Cited

OTHER PUBLICATIONS

FcRn and design of IgG1 variants with improved binding to the Fc gamma R," J Biol Chem, Mar. 2, 2001, 276(9):6591-604. Epub Nov. 28, 2000.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-73. Epub Nov. 8, 2002.

Siberil et al., "Molecular aspects of human FcgammaR interactions with IgG: functional and therapeutic consequences," Immunol Lett, Aug. 15, 2006, 106(2):111-8. Epub Jun. 12, 2006.

Sims et al., "HMGB1 and RAGE in inflammation and cancer," Annu Rev Immunol, 2010, 28:367-88.

Singer et al., Genes & Genomes, Moscow, "Mir," 1998, 1:63-64 (in Russian, with what is believed to be a published English equivalent of those pages).

Smith et al., "FcgammaRIIB in autoimmunity and infection: evolutionary and therapeutic implications," Nat Rev Immunol, May 2010, 10(5):328-43.

Sondermann et al., "The 3.2-Å crystal structure of the human IgG1 Fc fragment-FcγRIII complex," Nature, 2000, 406(6793): 267.

Strohl, "Optimization of Fc-mediated effector functions of monoclonal antibodies," Curr Opin Biotechnol, Dec. 2009, 20(6):685-91.

Su et al., "Expression profile of FcgammaRIIb on leukocytes and its dysregulation in systemic lupus erythematosus," J Immunol, 2007, 178(5):3272-80.

Supplementary information provided by opponent for EP 2 552 955 (EP Application No. 11714860.1), (document submitted by Opponents in EPO Opposition Procedure for EP 2 552 955 and posted by EPO on Feb. 2, 2018), 3 pages.

Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol, 2010, 184(4):1968-76.

Takeuchi et al., "The Japanese experience with biologic therapies for rheumatoid arthritis," Nat Rev Rheumatol, Nov. 2010, 6(11):644-52. doi: 10.1038/nrrheum.2010.154. Epub Sep. 28, 2010.

Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).

Trinh et al., "Ipilimumab in the treatment of melanoma," Expert Opin Biol Ther, Jun. 2012, 12(6):773-82. doi: 10.1517/14712598.2012.675325. Epub Apr. 14, 2012.

Vaccaro et al., "Engineering the Fc region of immunoglobulin G to modulate in vivo antibody levels," Nat Biotechnol, Oct. 2005, 23(10):1283-8. Epub Sep. 25, 2005.

Vaccaro et al., "Divergent activities of an engineered antibody in murine and human systems have implications for therapeutic antibodies," Proc Natl Acad Sci USA, Dec. 5, 2006, 103(49):18709-14. Epub Nov. 20, 2006.

Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-28.

Veri et al., "Therapeutic control of B cell activation via recruitment of Fcgamma receptor IIb (CD32B) inhibitory function with a novel bispecific antibody scaffold," Arthritis Rheum, 2010, 62(7):1933-43.

Veri et al., "Monoclonal antibodies capable of discriminating the human inhibitory Fcgamma-receptor IIB (CD32B) from the activating Fcgamma-receptor IIA (CD32A): biochemical, biological and functional characterization," Immunology, 2007, 121(3):392-404.

Vidarsson et al., "IgG subclasses and allotypes: from structure to effector functions," Front Immunol, Oct. 20, 2014, 5:520. doi: 10.3389/fimmu.2014.00520. eCollection 2014.

Waelbroeck et al., "The pH Dependence of Insulin Binding," J Biol Chem, Jul. 25, 1982, 257(14):8284-91.

Ward et al., "Evidence to support the cellular mechanism involved in serum IgG homeostasis in humans," Int Immunol, Feb. 2003, 15(2):187-95.

Wang et al., "HMG-1 as a late mediator of endotoxin lethality in mice," Science, 1999, 285(5425):248-51.

Warmerdam et al., "Molecular basis for a polymorphism of human Fc gamma receptor II (CD32)," J Exp Med, 1990, 172(1):19-25.

Warncke et al., "Different adaptations of IgG effector function in human and nonhuman primates and implications for therapeutic antibody treatment," J Immunol, May 1, 2012, 188(9):4405-11. doi: 10.4049/jimmunol.1200090. Epub Mar. 28, 2012.

Weiner et al., "Monoclonal antibodies: versatile platforms for cancer immunotherapy," Nat Rev Immunol, May 2010, 10(5):317-27. doi: 10.1038/nri2744.

Welch et al., "Adalimumab (Humira) for the Treatment of Rheumatoid Arthritis," Am Fam Physician, Dec. 15, 2008, 78(12):1406-1408.

Wernersson et al., "IgG-mediated enhancement of antibody responses is low in Fc receptor gamma chain-deficient mice and increased in Fc gamma RII-deficient mice," J Immunol, 1999, 163(2):618-22.

Wilson et al., "An Fcγ receptor-dependent mechanism drives antibody-mediated target-receptor signaling in cancer cells," 2011, Cancer Cell, 19(1):101-13.

Wu et al., "Development of motavizumab, an ultra-potent antibody for the prevention of respiratory syncytial virus infection in the upper and lower respiratory tract," J Mol Biol, 2007, 368:652-665.

Wu et al., "Humanization of a Murine Monoclonal Antibody by Simultaneous Optimization of Framework and CDR Residues," J Mol Biol, Nov. 19, 1999, 294(1):151-62.

Xiao et al., "Pharmacokinetics of anti-hepcidin monoclonal antibody Ab 12B9m and hepcidin in cynomolgus monkeys," AAPS J, Dec. 2010, 12(4):646-57. doi: 10.1208/s12248-010-9222-0. Epub Aug. 25, 2010.

Xu et al., "Fc gamma Rs modulate cytotoxicity of anti-Fas antibodies: implications for agonistic antibody-based therapeutics," J Immunol, 2003, 171(2):562-8.

Yang et al., "Dataset of the binding kinetic rate constants of anti-PCSK9 antibodies obtained using the Biacore T100, ProteOn XPR36, Octet RED384, and IBIS MX96 biosensor platforms," Data Brief, Jul. 27, 2016, 8:1173-83. doi : 10. 1016/ J. dib. 2016.07.044. eCollection Sep. 2016.

Yang et al., "Maximizing in vivo target clearance by design of pH-dependent target binding antibodies with altered affinity to FcRn," mAbs, Oct. 2017, 9(7):1105-1117. doi : 10. 1080/ 19420862. 2017. 1359455. Epub Aug. 8, 2017.

Yarilin, Fundamentals of Immunology, M: Medicina, 1999, pp. 169-172, 354-358 (with English translation).

Yarilin, Fundamentals of Immunology, M: Medicina, 1999, pp. 175, 182 (with English translation).

Yarilin, Fundamentals of Immunology, M: Medicina, 1999, pp. 172-174 (with English translation).

Yarilin, Fundamentals of Immunology, M: Medicina, 1999, pp. 181-184 (with English translation).

Yeung et al., "A Therapeutic Anti-VEGF Antibody with Increased Potency Independent of Pharmacokinetic Half-life," Cancer Res, Apr. 15, 2010, 70(8):3269-77. doi : 10. 1158/ 0008-5472.CAN-09-4580. Epub Mar. 30, 2010.

Yeung et al., "Engineering human IgG1 affinity to human neonatal Fc receptor: impact of affinity improvement on pharmacokinetics in primates," J Immunol, 2009, 182(12):7663-71.

Yuasa et al., "Deletion of fcgamma receptor IIB renders H-2(b) mice susceptible to collagen-induced arthritis," J Exp Med, 1999, 189(1):187-94.

Zalevsky et al., "The impact of Fc engineering on an anti-CD19 antibody: increased Fcgamma receptor affinity enhances B-cell clearing in nonhuman primates," Blood, 2009, 113(16):3735-43. Epub Dec. 24, 2008.

Zalevsky et al., "Enhanced antibody half-life improves in vivo activity," Nat Biotechnol, 2010, 28(2):157-9.

Zhang et al., "Effective therapy for a murine model of human anaplastic large-cell lymphoma with the anti-CD30 monoclonal antibody, HeFi-1,does not require activating Fc receptors," Blood, 2006, 108(2):705-10.

(56) References Cited

OTHER PUBLICATIONS

Zheng et al., "Translational pharmacokinetics and pharmacodynamics of an FcRn-variant anti-CD4 monoclonal antibody from preclinical model to phase I study," Clin Pharmacol Ther, Feb. 2011, 89(2):283-90. doi: 10.1038/clpt.2010.311. Epub Dec. 29, 2010.
International Search Report for App. Ser. No. PCT/JP2013/053011, mailed Apr. 8, 2013, 8 pages.
International Preliminary Report on Patentability for App. Ser. No. PCT/JP2013/053011, dated Aug. 12, 2014, 9 pages.
International Search Report for App. Ser. No. PCT/JP2011/001888, mailed on Nov. 2, 2011, 7 pages.
International Preliminary Report on Patentability for App. Ser. No. PCT/JP2012/058603, dated Oct. 8, 2013, 11 pages.
International Search Report for App. Ser. No. PCT/JP2012/058603, mailed May 29, 2012, 2 pages.
International Search Report for App. Ser. No. PCT/JP2012/075083, mailed Oct. 23, 2012, 2 pages.
International Preliminary Report on Patentability for App. Ser. No. PCT/JP2012/075083, dated Apr. 1, 2014, 8 pages.
International Search Report for App. Ser. No. PCT/JP2012/006218, mailed Mar. 26, 2013, 11 pages.
International Search Report for App. Ser. No. PCT/JP2013/084809, mailed Apr. 1, 2014, 4 pages.
International Preliminary Report on Patentability for App. Ser. No. PCT/JP2013/084809, dated Jun. 30, 2015, 7 pages.
USPTO Restriction Requirement in U.S. Appl. No. 14/001,218, dated Dec. 2, 2015, 8 pages.
Fish & Richardson P.C., Reply to Restriction Requirement dated Dec. 2, 2015 in U.S. Appl. No. 14/001,218, filed Feb. 1, 2016, 1 page.
USPTO Office Action in U.S. Appl. No. 14/001,218, dated Apr. 4, 2016, 13 pages.
Fish & Richardson P.C., Reply to Office Action dated Apr. 4, 2016 in U.S. Appl. No. 14/001,218, filed Oct. 3, 2016, 15 pages.
USPTO Final Office Action in U.S. Appl. No. 14/001,218, dated Dec. 2, 2016, 10 pages.
USPTO Interview Summary in U.S. Appl. No. 14/001,218, dated Jan. 12, 2017, 3 pages.
Fish & Richardson P.C., Reply to Office Action dated Dec. 16, 2016 in U.S. Appl. No. 14/001,218, filed Jun. 16, 2017, 15 pages.
USPTO Office Action in U.S. Appl. No. 14/001,218, dated Jun. 27, 2017, 12 pages.
USPTO Final Office Action in U.S. Appl. No. 14/001,218, dated Jan. 29, 2018, 11 pages.
USPTO Advisory Action in U.S. Appl. No. 14/001,218, dated Apr. 11, 2018, 3 pages.
USPTO Non-Final Office Action in U.S. Appl. No. 14/001,218, dated Mar. 18, 2019, 32 pages.
USPTO Restriction Requirement in U.S. Appl. No. 15/015,287, dated Mar. 13, 2017, 18 pages.
USPTO Notice of Allowance in U.S. Appl. No. 15/015,287, dated Mar. 27, 2018, 90 pages.
USPTO Restriction Requirement in U.S. Appl. No. 14/347,034, dated Dec. 18, 2014, 9 pages.
USPTO Non-Final Office Action in U.S. Appl. No. 14/347,034, dated Apr. 16, 2015, 9 pages.
USPTO Final Office Action in U.S. Appl. No. 14/347,034, dated Oct. 16, 2015, 5 pages.
USPTO Non-Final Office Action in U.S. Appl. No. 14/347,034, dated May 25, 2017, 16 pages.
USPTO Non-Final Office Action in U.S. Appl. No. 14/347,034, dated Jan. 8, 2018, 15 pages.
Non-Final Office Action for U.S. Appl. No. 15/230,904, dated May 25, 2017, 9 pages.
Non-Final Office Action for U.S. Appl. No. 15/230,904, dated Jan. 8, 2018, 16 pages.
USPTO Restriction Requirement in U.S. Appl. No. 14/007,947, dated Nov. 30, 2015, 9 pages.
USPTO Non-Final Office Action in U.S. Appl. No. 14/007,947, dated Aug. 22, 2016, 31 pages.
USPTO Final Office Action in U.S. Appl. No. 14/007,947, dated Apr. 21, 2017, 9 pages.
USPTO Non-Final Office Action in U.S. Appl. No. 14/007,947, dated Apr. 2, 2018, 27 pages.
USPTO Final Office Action in U.S. Appl. No. 14/007,947, dated Dec. 10, 2018, 16 pages.
USPTO Notice of Allowance and Examiner-Initiated Interview Summary in U.S. Appl. No. 14/007,947, dated Apr. 3, 2019, 10 pages.
USPTO Restriction Requirement in U.S. Appl. No. 14/654,895, dated Sep. 21, 2017, 7 pages.
USPTO Non-final Office Action in U.S. Appl. No. 14/654,895, dated Feb. 7, 2018, 39 pages.
USPTO Non-final Office Action in U.S. Appl. No. 15/024,063, dated Feb. 7, 2018, 91 pages.
USPTO Non-Final Office Action in U.S. Appl. No. 16/028,140, dated Jul. 9, 2019, 95 pages.
Abe et al., "Effect of $\beta_2$-microglobulin adsorption column on dialysis-related amyloidosis," Kidney Int, Oct. 2003, 64(4):1522-1528. doi: 10.1046/j.1523-1755.2003.00235.x.
Nagaoka et al., "Single amino acid substitution in the mouse IgG1 Fc region induces drastic enhancement of the affinity to protein A," Protein Eng, Apr. 2003, 16(4):243-245. doi: 10.1093/proeng/gzg037.
Warmerdam et al., "The human low affinity immunoglobulin G Fc receptor IIC gene is a result of an unequal crossover event," J Biol Chem, Apr. 5, 1993, 268(10):7346-7349.
U.S. Appl. No. 13/637,415, Igawa et al., filed Feb. 4, 2013.
U.S. Appl. No. 15/050,145, Igawa et al., filed Feb. 22, 2016.
U.S. Appl. No. 15/495,026, Igawa et al., filed Apr. 24, 2017.
U.S. Pat. No. 10,618,965, Igawa et al., issued Apr. 14, 2020.
U.S. Appl. No. 16/806,027, Igawa et al., filed Mar. 2, 2020.
U.S. Appl. No. 15/230,904, Igawa et al., filed Aug. 8, 2016 (abandoned).
U.S. Appl. No. 14/347,034, Igawa et al., filed Mar. 25, 2014 (abandoned).
U.S. Pat. No. 10,253,100, Igawa et al., issued Apr. 9, 2019.
U.S. Appl. No. 14/001,218, Mimoto et al., filed Dec. 2, 2013.
U.S. Pat. No. 9,890,218, Mimoto et al., issued Feb. 13, 2018.
U.S. Appl. No. 14/377,556, Kuramochi et al., Aug. 8, 2014 (abandoned).
U.S. Pat. No. 10,766,960, Igawa et al., issued Sep. 8, 2020.
U.S. Appl. No. 15/963,455, Ruike et al., filed Apr. 26, 2018.
U.S. Appl. No. 17/028,210, Katada et al., filed Sep. 22, 2020.
Fish & Richardson P.C., Response to Restriction Requirement dated Dec. 15, 2016, in U.S. Appl. No. 14/377,556, dated Feb. 13, 2017, 1 page.
Fish & Richardson P.C., Amendment in Reply to Office Action of Feb. 27, 2017 in U.S. Appl. No. 14/377,556, dated May 26, 2017, 18 pages.
Fish & Richardson P.C., Amendment in Reply to Action of Jul. 17, 2017 in U.S. Appl. No. 14/377,556, dated Oct. 10, 2017, 18 pages.
Fish & Richardson P.C., Reply to Action of Dec. 12, 2017 in U.S. Appl. No. 14/377,556, dated Mar. 8, 2018, 14 pages.
Fish & Richardson P.C., Supplemental Reply to Office Action of Dec. 12, 2017 in U.S. Appl. No. 14/377,556, dated Mar. 14, 2018, 2 pages.
Fish & Richardson P.C., Brief on Appeal in U.S. Appl. No. 14/377,556, dated Jan. 29, 2019, 40 pages.
Fish & Richardson P.C. Reply to Action of Apr. 18, 2019 in U.S. Appl. No. 14/377,556, dated Jul. 17, 2019, 6 pages.
U.S. Appl. No. 14/347,321, Igawa et al., filed Mar. 26, 2014.
Decision of the Opposition Division dated Dec. 19, 2019 in EP 2 552 955 (document submitted by Patentee (Chugai Seiyaku Kabushiki Kaisha) in the grounds of appeal on Apr. 28, 2020 in EP 2 552 955).
Patentee submission dated Jul. 16, 2015 (Response to Search Report filed on Jul. 16, 2015) (document submitted by the Opponent on May 6, 2020 in Opposition of EP 2 679 681).
U.S. Appl. No. 16/539,765, IGAWA et al..
U.S. Appl. No. 17/144,342, IGAWA et al..
Application as filed for EP 2 698 431, 375 pages (document cited during EPO opposition proceedings of EP 2 698 431 on Jun. 23, 2021).

(56) References Cited

OTHER PUBLICATIONS

Borrok et al., "pH-dependent Binding Engineering Reveals an FcRn Affinity Threshold That Governs IgG Recycling," J Biol Chem, Feb. 13, 2015, 290(7):4282-4290. doi: 10.1074/jbc.M114.603712. Epub Dec. 23, 2014.

Crowe et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol, Jan. 1992, 87(1):105-110.

Decision of the Opposition Division in EP 2 275 443, dated Apr. 26, 2018, 29 pages (submitted on Sep. 3, 2021 with a response to EPO office action in EP 3 702 360 A).

English translation of PCT/JP2011/072550, 283 pages (corresponding to WO 2012/132067, which was cited in IDS filed on Feb. 20, 2020). The translation was submitted in the EPO opposition proceedings of EP 2 698 431 on Jun. 23, 2021.

English translation of PCT/JP2012/054624, 110 pages (corresponding to WO 2012/115241, which was cited in IDS filed on Feb. 20, 2020). The translation was submitted in the EPO opposition proceedings of EP 2 698 431 on Jun. 23, 2021.

Han et al., "Monoclonal antibodies: interspecies scaling with minimal preclinical information," Ther Deliv, Mar. 2011, 2(3):359-368.

James et al., "1.9 A structure of the therapeutic antibody CAMPATH-1H fab in complex with a synthetic peptide antigen," J Mol Biol, Jun. 4, 1999, 289(2):293-301.

Jung et al., "Aglycosylated IgG variants expressed in bacteria that selectively bind FcKRI potentiate tumor cell killing by monocyte-dendritic cells," Proc Natl Acad Sci USA, Jan. 12, 2010, 107(2):604-609.

Mimoto et al., "Engineered antibody Fc variant with selectively enhanced FcγRIIb binding over both FcγRIIa$^{R131}$ and FcγRIIa$^{H131}$," Protein Eng Des Sel, Oct. 2013, 26(10):589-598. doi: 10.1093/protein/gzt022. Epub Jun. 5, 2013.

PCT/JP2011/001888, filed Mar. 30, 2011, 203 pages, corresponding to WO 2011/122011, which was cited in IDS filed on Feb. 20, 2020 (document cited in EPO opposition proceedings of EP 2 698 431 on Jun. 23, 2021).

Presta et al., "Engineering therapeutic antibodies for improved function," Biochem Soc Trans, Aug. 2002, 30(4):487-490.

Salfeld et al., "Isotype selection in antibody engineering," Nat. Biotechnol, 2007, 25(12):1369-1372.

Siberil et al., "Molecular aspects of human FcKR interactions with IgG: Functional and therapeutic consequences," Immunol Lett, Aug. 15, 2006, 106(2):111-118. Epub Jun. 12, 2006.

U.S. Appl. No. 14/007,947, Igawa et al., filed Dec. 30, 2013.

U.S. Appl. No. 14/654,895, Igawa et al., filed Jun. 23, 2015.

Chugai Seiyaku Kabushiki Kaisha, "Verification of the Tm-increasing effect of the T250V/T307P substitutions," Sep. 9, 2019 (with English translation).

Ghetie et al., "Multiple Roles for the Major Histocompatibility Complex Class I—Related Receptor FcRn," Annu Rev Immunol, Apr. 2000, 18:739-66.

Kanyavuz et al., "Breaking the law: unconventional strategies for antibody diversification," Nat Rev Immunol, Jun. 2019, 19(6):355-368. doi: 10.1038/s41577-019-0126-7.

Kipriyanov et al., "Generation of Recombinant Antibodies," Mol Biotechnol, Sep. 1999, 12(2):173-201.

Medesan et al., "Comparative studies of rat IgG to further delineate the Fc:FcRn interaction site," Eur J Immunol, Jul. 1998, 28(7):2092-100.

USPTO Restriction Requirement in U.S. Appl. No. 14/377,556, dated Dec. 15, 2016, 11 pages.

USPTO Non-Final Office Action in U.S. Appl. No. 14/377,556, dated Feb. 27, 2017, 10 pages.

USPTO Applicant-Initiated Interview Summary in U.S. Appl. No. 14/377,556, dated May 25, 2017, 3 pages.

USPTO Final Office Action in U.S. Appl. No. 14/377,556, dated Jul. 7, 2017, 10 pages.

USPTO Non-Final Office Action in U.S. Appl. No. 14/377,556, dated Dec. 12, 2017, 11 pages.

USPTO Final Office Action in U.S. Appl. No. 14/377,556, dated May 11, 2018, 11 pages.

USPTO Non-Final Office Action in U.S. Appl. No. 14/377,556, dated Apr. 18, 2019, 9 pages.

USPTO Final Office Action in U.S. Appl. No. 14/377,556, dated Sep. 24, 2019, 12 pages.

USPTO Restriction Requirement in U.S. Appl. No. 14/347,187, dated Jan. 26, 2017, 9 pages.

USPTO Non-Final Office Action in U.S. Appl. No. 14/347,187, dated Jun. 14, 2017, 23 pages.

USPTO Final Office Action in U.S. Appl. No. 14/347,187, dated Jan. 19, 2018, 17 pages.

USPTO Non-Final Office Action in U.S. Appl. No. 14/347,187, dated Sep. 4, 2018, 11 pages.

U.S. Appl. No. 14/377,556, Kuramochi et al., Aug. 8, 2014.

Annotated amino acid sequence of the variable heavy (VH) and variable light (VL) domains of the monoclonal antibodies bevacizumab/Avastin, adalimumab/Humira, omalizumab/Xolair, and rituximab/Mabthera, dated Jul. 2019, 10 pages (submitted to the EPO with the written submission to attend oral proceedings on Sep. 6, 2019 by Opponent 1 in EP 11714860.1).

Evidence for the publication date of Zalevsky et al., "Enhanced antibody half-life improves in vivo activity," Nat Biotechnol, Feb. 2010, 28(2):157-9, 1 page (submitted to the EPO with the written submission to attend oral proceedings on Sep. 6, 2019 by Opponent 1 in EP 11714860.1).

Expert declaration of Dr. Joachim Boucneau, dated Sep. 6, 2019, 13 pages (submitted to the EPO with the written submission to attend oral proceedings on Sep. 6, 2019 by Opponent 1 in EP 11714860.1).

Proprietor's (Chugai Seiyaku Kabushiki Kaisha) Submission dated Sep. 5, 2016 in EP 11714860.1, 6 pages (submitted to the EPO with the written submission to attend oral proceedings on Sep. 6, 2019 by Opponent 1 in EP 11714860.1).

Proprietor's (Chugai Seiyaku Kabushiki Kaisha) Submission dated Sep. 19, 2016 in EP 11714860.1, 3 pages (submitted to the EPO with the written submission to attend oral proceedings on Sep. 6, 2019 by Opponent 1 in EP 11714860.1).

Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 5 in EP 2 275 443).

Rich et al., "A global benchmark study using affinity-based biosensors," Anal Biochem, Mar. 15, 2009, 386(2):194-216. doi: 10.1016/j.ab.2008.11.021. Epub Nov. 27, 2008.

Schlothauer et al., "Novel human IgG1 and IgG4 Fc-engineered antibodies with completely abolished immune effector functions," Protein Eng Des Sel, Oct. 2016, 29(10):457-466. doi: 10.1093/protein/gzw040. Epub Aug. 29, 2016.

Sigma product information for ACES buffer, 1 page (submitted to the EPO with the written submission to attend oral proceedings on Sep. 6, 2019 by Opponent 1 in EP 11714860.1).

Table pertaining to WO 2009/086320A, 4 pages (submitted to the EPO with the written submission to attend oral proceedings on Sep. 6, 2019 by Opponent 1 in EP 11714860.1).

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

USPTO Final Office Action in U.S. Appl. No. 14/001,218, dated Dec. 16, 2016, 11 pages.

USPTO Final Office Action in U.S. Appl. No. 14/001,218, dated Nov. 21, 2019, 17 pages.

U.S. Appl. No. 17/846,672, Mimoto et al., filed Jun. 22, 2022.

U.S. Appl. No. 17/788,998, Katada et al., filed Jun. 24, 2022.

EUTM register extract—Biacore, 4 pages (document downloaded on Aug. 26, 2020, submitted during the EPO opposition proceedings of EP 2 552 955, and posted by EPO on Sep. 15, 2020).

Guidance on the use of International Nonproprietary Names (INNs) for Pharmaceutical Substances, World Health Organization, 2017, 55 pages (submitted by the Opponents in Mar. 2020 in EPO opposition proceedings of EP 2 708 558 and EP 2 708 559).

(56) References Cited

OTHER PUBLICATIONS

Lescar et al., "Crystal Structure of a Cross-reaction Complex between Fab F9.13.7 and Guinea Fowl Lysozyme," J Biol Chem, Jul. 28, 1995, 270(30):18067-18076.
USPTO Non-Final Office Action in U.S. Appl. No. 14/001,218, dated Jun. 16, 2020, 9 pages.
USPTO Final Office Action in U.S. Appl. No. 14/001,218, dated Feb. 2, 2021, 11 pages.
USPTO Non-Final Office Action in U.S. Appl. No. 14/001,218, dated Dec. 29, 2021, 10 pages.
U.S. Appl. No. 17/848,983, Katada et al., filed Jun. 24, 2022.
U.S. Appl. No. 18/052,258, Igawa et al., filed Nov. 3, 2022.
U.S. Appl. No. 18/022,342, Katada et al., filed Feb. 21, 2023.
U.S. Appl. No. 18/023,038, Katada et al., filed Feb. 24, 2023.
U.S. Appl. No. 18/298,743, Igawa et al., filed Apr. 11, 2023.
U.S. Appl. No. 18/470,185, Katada et al., filed Sep. 19, 2023.
U.S. Appl. No. 18/480,730, Igawa et al., filed Oct. 4, 2023.
U.S. Appl. No. 18/533,360, Igawa et al., filed Dec. 8, 2023.
U.S. Pat. No. 11,718,678 B2, Igawa et al., issued Aug. 8, 2023.
U.S. Pat. No. 11,827,699 B2, Igawa et al., issued Nov. 28, 2023.
USPTO Restriction Requirement in U.S. Appl. No. 17/848,983, dated Jul. 19, 2023, 9 pages.
Attwood, "The Babel of Bioinformatics," Science, Oct. 20, 2000, 290(5491):471-473.
Chen et al., "Enhancement and destruction of antibody function by somatic mutation; unequal occurrence is controlled by V gene combinatorial associations," EMBO J, Jun. 15, 1995, 14(12):2784-2794.
Contardi et al., "CTLA-4 is constitutively expressed on tumor cells and can trigger apoptosis upon ligand interaction," Int J Cancer, Nov. 20, 2005, 117(4):538-550.
Koenig et al., "Mutational landscape of antibody variable domains reveals a switch modulating the interdomain conformational dynamics and antigen binding," Proc Natl Acad Sci USA, Jan. 24, 2017, 114(4):E486-E495.
Kussie et al., "A Single Engineered Amino Acid Substitution Changes Antibody Fine Specificity," J Immunol, Jan. 1, 1994, 152(1):146-152.
Skolnick et al., "From genes to protein structure and function: novel applications of computational approaches in the genomic era," Trends Biotechnol, Jan. 2000, 18(1):34-39.
USPTO Non-Final Office Action in U.S. Appl. No. 17/848,983, dated Dec. 20, 2023, 20 pages.
USPTO Restriction Requirement in U.S. Appl. No. 18/298,743, dated Jul. 31, 2024, 8 pages.
Diamond et al., "Somatic mutation of the T15 heavy chain gives rise to an antibody with autoantibody specificity," Proc Natl Acad Sci USA, Sep. 1984, 81(18):5841-5844.
Flores et al., "Dominant Expression of the Inhibitory FcγRIIB Prevents Antigen Presentation by Murine Plasmacytoid Dendritic Cells," J Immunol, Dec. 1, 2009, 183(11):7129-7139. doi: 10.4049/jimmunol.0901169.
Gary et al., Chapter 8, "Making Antibodies in Bacteria," Making and Using Antibodies: A Practical Handbook, CRC Press, Taylor & Francis Group, 2006, pp. 157-177.
Kabat et al., "Sequences of Proteins of Immunological Interest," 1991, National Institute of Health Publication No. 91-3242, pp. 103, 310.
King, Chapter 5, "Production of Monoclonal Antibodies," Applications and Engineering of Monoclonal Antibodies, Taylor & Francis, ISBN 0-203-21169-3, 2005, pp. 151-159, 162-164.
Kontermann et al., Chapter 4, "Mouse Immune Libraries for the Generation of ScFv Fragments Directed Against Human Cell Surface Antigens," 1:47-62; and Chapter 27, "Engineering of the Fc Region for Improved PK (FcRn Interaction)," 1:415-427, Antibody Engineering, 2010.
Mendez-Fernandez et al., "The inhibitory FcγRIIb modulates the inflammatory response and influences atherosclerosis in male apoE-/- mice," Atherosclerosis, Jan. 2011, 214(1):73-80. doi: 10.1016/j.atherosclerosis.2010.10.018.
Ohno et al., "Antigen-binding specificities of antibodies are primarily determined by seven residues of $V_H$," Proc Natl Acad Sci USA, May 1985, 82(9):2945-2949.
Singer et al., Chapter 3, "The Logic and Machinery of Gene Expression," Genes & Genomes, Moscow, Mir, 1998, pp. 115-188 (with what are believed to be the corresponding pages from an English version of Genes & Genomes).
Tackenberg et al., "Impaired inhibitory Fcγ receptor IIB expression on B cells in chronic inflammatory demyelinating polyneuropathy," Proc Natl Acad Sci USA, Mar. 24, 2009, 106(12):4788-4792. doi: 10.1073/pnas.0807319106.

\* cited by examiner

```
Kabat     1                                          2
EU index  1-2---------3---------4---------5---------6---------7---------8---------9---------2---------0
          8-0---------0---------0---------0---------0---------0---------0---------0---------0---------0
IgG1      ASTKGPSVFPLAPSSKSTSGTIAALGCLVKDYFPEPVTVSWNSGALTSGVHTFPAVLQSSGLYSLSSVVTVPSSSLGTQTYICNVNHKPSNTKVDKKVEPKSCD-
IgG2      ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK--CC
IgG3      ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRVELKTPLG
IgG4      ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYG--

Kabat     2                                                            7                                 8
EU index  2---------3---------4---------5---------6---------7---------8---------9---------0
          2---------0---------0---------0---------0---------0---------0---------0---------0
IgG1      -KTHTCPP-------------CPAPELLGGPSVFLFPPKPKDTLMISRTPEVTCVVVDVSHEDPEVKFNWYVD
IgG2      -V--E-CPP------------CPAPPVA--GPSVFLFPPKPKDTLMISRTPEVTCVVVDVSHEDPEVQFNWYVD
IgG3      DTTHTCPRCPEPKSCDTPPPCPRCPEPKSCDTPPPCPRCPAPELLGGPSVFLFPPKPKDTLMISRTPEVTCVVVDVSHEDPEVQFKWYVD
IgG4      ---PPCPS-------------CPAPEFLGGPSVFLFPPKPKDTLMISRTPEVTCVVVDVSQEDPEVQFNWYVD Kabat     2                                                                                3
EU index  8---------9---------0---------1---------2---------3---------4---------5---------6---------7---------9
          1---------0---------0---------0---------0---------0---------0---------0---------0---------0---------0
IgG1      GVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNG
IgG2      GVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNG
IgG3      GVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSG
IgG4      GVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNG Kabat     3                  4
EU index  8---------9---------0---------1---------2---------3---------4
          6---------0---------0---------0---------0---------0---------0---------7
IgG1      QPENNYKTTPPVLDSDGSFFLYSKLTVDKSRWQQGNVFSCSVMHEALHNHYTQKSLSLSPGK (SEQ ID NO:11)
IgG2      QPENNYKTTPPMLDSDGSFFLYSKLTVDKSRWQQGNVFSCSVMHEALHNHYTQKSLSLSPGK (SEQ ID NO:12)
IgG3      QPENNYNTTPPMLDSDGSFFLYSKLTVDKSRWQQGNIFSCSVMHEALHNRFTQKSLSLSPGK (SEQ ID NO:13)
IgG4      QPENNYKTTPPVLDSDGSFFLYSRLTVDKSRWQEGNVFSCSVMHEALHNHYTQKSLSLSLGK (SEQ ID NO:14)
```

MODIFIED Fc REGION OF ANTIBODY

CROSS-REFERENCE TO RELATED APPLICATIONS

This application is divisional of U.S. application Ser. No. 14/377,556, filed on Aug. 8, 2014, which is the National Stage of International Application No. PCT/JP2013/053011, filed on Feb. 8, 2013, which claims the benefit of Japanese Application No. 2012-026371, filed on Feb. 9, 2012.

TECHNICAL FIELD

The present invention provides antibody Fc regions in which the amino acid sequence of a naturally-occurring antibody Fc region has been modified, antibodies containing such an Fc region, pharmaceutical compositions containing such an antibody, and methods for producing them.

BACKGROUND ART

Antibodies are drawing attention as pharmaceuticals as they are highly stable in plasma and have few side effects. In particular, a number of IgG-type antibody pharmaceuticals are available on the market and many antibody pharmaceuticals are currently under development (Non-patent Documents 1 and 2).

Recently, active research has been conducted on enhancing antibody functions by introducing artificial amino acid modification into antibody Fc regions. Specifically, Fc regions with improved pharmacokinetics, Fc regions with enhanced ADCC activity, which is an effector function, and Fc regions with reduced ADCC activity in neutralizing antibodies have been studied (Non-Patent Documents 3-6). However, such Fc region modifications are known to cause adverse effects on physical properties of antibodies. For example, a modified Fc region with enhanced ADCC activity has been reported to show a decrease in melting temperature by approximately 20° C. (Non-Patent Document 6). Furthermore, there are reports that modified Fc regions with reduced ADCC activity show a decrease in melting temperature by approximately 5° C., readily undergo digestion by hydrolases, and readily degrade under acidic conditions (Non-Patent Documents 7-9). Furthermore, modified Fc regions with improved retention in blood have been reported to show reduced thermal stability and storage stability (Patent Document 1).

Thus, in most of the modified Fc regions discovered so far, the enhancement of their functions has resulted in loss of their excellent stability, which is one of the advantages of antibodies.

As an effort to improve stability, there is a report of a technique for amino acid modification in the CH2 domain to introduce cysteines (Non-Patent Document 10). It has been reported that formation of new disulfide bonds by introduction of cysteines increases the thermal stability by approximately 10° C. to 20° C. In this report, however, only the CH2 domain was evaluated for thermal stability; therefore, the thermal stability of the IgG form is unknown. Furthermore, the formation of additional disulfide bonds is expected to cause an increase in heterogeneity.

As described above, there has so far been no report on an Fc region that is excellent in both activity and stability.

Prior art documents related to the present invention are shown below:

PRIOR ART DOCUMENTS

Patent Documents

[Patent Document 1] WO2007/092772
[Patent Document 2] WO2010/085682

Non-Patent Documents

[Non-patent Document 1] Monoclonal antibody successes in the clinic, Janice M Reichert, Clark J Rosensweig, Laura B Faden & Matthew C Dewitz, Nature Biotechnology 23, 1073-1078 (2005)
[Non-patent Document 2] Pavlou A K, Belsey M J., The therapeutic antibodies market to 2008, Eur J Pharm Biopharm. 2005 April; 59(3):389-96.
[Non-patent Document 3] Hinton P R, Xiong J M, Johlfs M G Tang M T, Keller S, Tsurushita N., An engineered human IgG1 antibody with longer serum half-life, J Immunol. 2006 Jan. 1; 176(1):346-56
[Non-patent Document 4] Ghetie V, Popov S, Borvak J, Radu C, Matesoi D, Medesan C, Ober R J, Ward E S., Increasing the serum persistence of an IgG fragment by random mutagenesis, Nat Biotechnol. 1997 July; 15(7): 637-40
[Non-patent Document 5] Oganesyan V, Damschroder M M, Leach W, Wu H, Dall'Acqua W F., Structural characterization of a mutated, ADCC-enhanced human Fc fragment, Mol Immunol. 2008 April; 45(7): 1872-82
[Non-patent Document 6] Oganesyan V, Gao C, Shirinian L, Wu H, Dall'Acqua W F., Structural characterization of a human Fc fragment engineered for lack of effector functions, Biol Crystallogr. 2008 June; 64(Pt 6):700-4
[Non-patent Document 7] Liu H, Bulseco G G, Sun J., Effect of posttranslational modifications on the thermal stability of a recombinant monoclonal antibody, Immunol Lett. 2006 August; 106(2): 144-53
[Non-patent Document 8] Gaza-Bulseco G, Liu H., Fragmentation of a recombinant monoclonal antibody at various pH., Pharm Res. 2008 August; 25(8):1881-90
[Non-patent Document 9] Raju T S, Scallon B J., Glycosylation in the Fc domain of IgG increases resistance to proteolytic cleavage by papain, Biochem Biophys Res Commun. 2006 March; 341(3):797-803
[Non-patent Document 10] Gong R, Vu B K, Feng Y, Prieto D A, Dyba M A, Walsh J D, Prabakaran P, Veenstra T D, Tarasov S G, Ishima R, Dimitrov D S., Engineered human antibody constant domains with increased stability, J Biol Chem. 2009 March; 284(21):14203-14210
[Non-patent Document 11] Remmele R L Jr, Callahan W J, Krishnan S, Zhou L, Bondarenko P V, Nichols A C, Kleemann G R, Pipes G D, Park S, Fodor S, Kras E, Brems D N., Active dimer of Epratuzumab provides insight into the complex nature of an antibody aggregate, J Pharm Sci. 2006 January; 95(1):126-45.
[Non-patent Document 12] Rosenberg A S, Effects of Protein Aggregates: An Immunologic Perspective, AAPS J. 2006 August; 8(3); E501-E507

SUMMARY OF THE INVENTION

Problems to be Solved by the Invention

The present invention was achieved in view of the above circumstances. An objective of the present invention is to provide polypeptides whose stability has been improved by modifying amino acids in the antibody Fc region.

Means for Solving the Problems

The present inventors considered that, in the production of modified Fc regions, it would be desirable to enhance their function while maintaining antibody stability, or to recover stability that had been reduced due to functional enhancement.

The present inventors conducted dedicated studies, and as a result succeeded in obtaining polypeptides with an antibody Fc region which have been modified in at least one amino acid in a loop region of the Fc region and which thereby have improved stability as compared to that of a parent polypeptide.

Furthermore, by combining multiple amino acid modifications in the loop region, polypeptides with improved thermal stability and maintained or enhanced FcγR-binding activity, and polypeptides with improved thermal stability and decreased FcγR-binding activity, as compared to those of a parent polypeptide, were successfully obtained. Furthermore, polypeptides not only with improved thermal stability and adjusted FcγR-binding activity but also with decreased aggregate content were successfully obtained.

More specifically, the present invention relates to the following:

[1] a polypeptide comprising an antibody Fc region, wherein at least one amino acid has been modified in a loop region of the Fc region, and the polypeptide has improved stability as compared to that of a parent polypeptide;

[2] the polypeptide of [1], wherein the stability is assessed or determined using melting temperature (Tm) as an index;

[3] the polypeptide of [1] or [2], wherein at least one or more amino acid mutations have been introduced into the loop region of the Fc region at amino acid position(s) selected from the group consisting of position 234 (EU numbering), position 235 (EU numbering), position 236 (EU numbering), position 237 (EU numbering), position 238 (EU numbering), position 239 (EU numbering), position 247 (EU numbering), position 250 (EU numbering), position 265 (EU numbering), position 266 (EU numbering), position 267 (EU numbering), position 268 (EU numbering), position 269 (EU numbering), position 270 (EU numbering), position 271 (EU numbering), position 295 (EU numbering), position 296 (EU numbering), position 298 (EU numbering), position 300 (EU numbering), position 307 (EU numbering), position 309 (EU numbering), position 315 (EU numbering), position 324 (EU numbering), position 325 (EU numbering), position 326 (EU numbering), position 327 (EU numbering), position 329 (EU numbering), position 330 (EU numbering), position 333 (EU numbering), position 335 (EU numbering), position 337 (EU numbering), position 360 (EU numbering), position 385 (EU numbering), position 386 (EU numbering), position 387 (EU numbering), position 389 (EU numbering), position 428 (EU numbering), and position 433 (EU numbering);

[4] the polypeptide of any one of [1] to [3], which further has FcγR-binding activity that is maintained or enhanced as compared to that of a parent polypeptide;

[5] the polypeptide of any one of [1] to [3], which further has FcγR-binding activity that is decreased as compared to that of a parent polypeptide;

[6] the polypeptide of any one of [1] to [5], wherein at least one or more amino acid mutations have been introduced into the loop region of the Fc region at amino acid position(s) selected from the group consisting of position 234 (EU numbering), position 235 (EU numbering), position 239 (EU numbering), position 266 (EU numbering), position 267 (EU numbering), position 268 (EU numbering), position 269 (EU numbering), position 270 (EU numbering), position 295 (EU numbering), position 296 (EU numbering), position 298 (EU numbering), position 300 (EU numbering), position 324 (EU numbering), position 325 (EU numbering), position 326 (EU numbering), and position 330 (EU numbering);

[7] the polypeptide of any one of [1] to [4] and [6], wherein at least one or more amino acid mutations have been introduced into the loop region of the Fc region at amino acid position(s) selected from the group consisting of position 234 (EU numbering), position 266 (EU numbering), position 268 (EU numbering), position 269 (EU numbering), position 270 (EU numbering), position 295 (EU numbering), position 300 (EU numbering), position 324 (EU numbering), position 326 (EU numbering), and position 330 (EU numbering);

[8] the polypeptide of any one of [1] to [4], [6], and [7], wherein the amino acid modifications in the loop region of the Fc region are at least one or more amino acid modifications selected from the group consisting of substitution of the amino acid at position 234 (EU numbering) with Ile, substitution of the amino acid at position 266 (EU numbering) with Ile, substitution of the amino acid at position 268 (EU numbering) with Gln, substitution of the amino acid at position 269 (EU numbering) with Asp, substitution of the amino acid at position 270 (EU numbering) with Glu, substitution of the amino acid at position 295 (EU numbering) with Met or Leu, substitution of the amino acid at position 300 (EU numbering) with Glu, substitution of the amino acid at position 324 (EU numbering) with His, substitution of the amino acid at position 326 (EU numbering) with Ser or Ala, and substitution of the amino acid at position 330 (EU numbering) with His or Tyr;

[9] the polypeptide of any one of [1] to [3], [5] and [6], wherein at least one or more amino acid mutations have been introduced into the loop region of the Fc region at amino acid positions selected from the group consisting of position 234 (EU numbering), position 235 (EU numbering), position 239 (EU numbering), position 267 (EU numbering), position 268 (EU numbering), position 270 (EU numbering), position 295 (EU numbering), position 296 (EU numbering), position 298 (EU numbering), and position 325 (EU numbering);

[10] the polypeptide of any one of [1] to [3], [5], [6], and [9], wherein the amino acid modifications in the loop region of the Fc region are at least one or more amino acid modifications selected from the group consisting of substitution of the amino acid at position 234 (EU numbering) with Lys or Arg, substitution of the amino acid at position 235 (EU numbering) with Lys or Arg, substitution of the amino acid at position 239 (EU numbering) with Lys, substitution of the amino acid at position 267 (EU numbering) with Pro, substitution of the amino acid at position 268 (EU numbering) with Met or Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with Gly, His, or Met;

[11] the polypeptide of any one of [1] to [4], wherein at least one or more amino acid mutations have been introduced into the loop region of the Fc region at amino acid position(s)

selected from the group consisting of position 295 (EU numbering), position 326 (EU numbering), and position 330 (EU numbering);

[12] the polypeptide of any one of [1] to [4] and [11], wherein the amino acid modifications in the loop region of the Fc region are at least one or more amino acid modifications selected from the group consisting of substitution of the amino acid at position 295 (EU numbering) with Met or Leu, substitution of the amino acid at position 326 (EU numbering) with Ser or Ala, and substitution of the amino acid at position 330 (EU numbering) with His or Tyr;

[13] the polypeptide of any one of [1] to [3] and [5], wherein at least one or more amino acid mutations have been introduced into the loop region of the Fc region at amino acid position(s) selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering);

[14] the polypeptide of any one of [1] to [3], [5], and [13], wherein the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys or Ser, substitution of the amino acid at position 268 (EU numbering) with Lys or His, substitution of the amino acid at position 270 (EU numbering) with Phe or Asp, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[15] the polypeptide of any one of [1] to [3] and [5], wherein at least one or more amino acid mutations have been introduced into the loop region of the Fc region at amino acid position(s) selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering);

[16] the polypeptide of any one of [1] to [3], [5], and [15], wherein the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[17] the polypeptide of any one of [1] to [3] and [5], wherein at least one or more amino acid mutations have been introduced into the loop region of the Fc region at amino acid position(s) selected from the group consisting of position 234 (EU numbering), position 235 (EU numbering), position 239 (EU numbering), position 295 (EU numbering), position 296 (EU numbering), position 298 (EU numbering), and position 325 (EU numbering);

[18] the polypeptide of any one of [1] to [3], [5], and [17], wherein the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys and Arg, substitution of the amino acid at position 239 (EU numbering) with Lys, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[19] the polypeptide of any one of [1] to [3] and [5], wherein at least one or more amino acid mutations have been introduced into the loop region of the Fc region at amino acid position(s) selected from the group consisting of position 234 (EU numbering), position 235 (EU numbering), position 268 (EU numbering), position 270 (EU numbering), position 295 (EU numbering), position 296 (EU numbering), position 298 (EU numbering), and position 325 (EU numbering);

[20] the polypeptide of any one of [1] to [3], [5], and [19], wherein the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[21] the polypeptide of any one of [1] to [3] and [5], wherein at least one or more amino acid mutations have been introduced into the loop region of the Fc region at amino acid position(s) selected from the group consisting of position 234 (EU numbering), position 235 (EU numbering), position 295 (EU numbering), position 296 (EU numbering), position 298 (EU numbering), and position 325 (EU numbering);

[22] the polypeptide of any one of [1] to [3], [5], and [21], wherein the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[23] the polypeptide of any one of [1] to [4], wherein at least one or more amino acid mutations have been introduced into the loop region of the Fc region at amino acid position(s) selected from the group consisting of position 247 (EU numbering), position 250 (EU numbering), position 307 (EU numbering), position 309 (EU numbering), position 315 (EU numbering), position 360 (EU numbering), position 385 (EU numbering), position 386 (EU numbering), position 387 (EU numbering), position 389 (EU numbering), position 428 (EU numbering), and position 433 (EU numbering);

[24] the polypeptide of any one of [1] to [4], and [23], wherein the amino acid modifications in the loop region of the Fc region are at least one or more amino acid modifications selected from the group consisting of substitution of the amino acid at position 247 (EU numbering) with Val, substitution of the amino acid at position 250 (EU numbering) with Phe, Ile, Met, Val, Trp, or Tyr, substitution of the amino acid at position 307 (EU numbering) with Ala, Gln, or Pro, substitution of the amino acid at position 309 (EU numbering) with Ala, Arg, or Pro, substitution of the amino acid at position 315 (EU numbering) with Ala, substitution of the amino acid at position 360 (EU numbering) with His, substitution of the amino acid at position 385 (EU numbering) with Asp, substitution of the amino acid at position 386 (EU numbering) with Pro, substitution of the amino acid at position 387 (EU numbering) with Glu, substitution of the amino acid at position 389 (EU numbering) with Ser, substitution of the amino acid at position 428 (EU numbering) with His, Trp, Tyr, or Phe, and substitution of the amino acid at position 433 (EU numbering) with Lys;

[25] the polypeptide of any one of [1] to [3] and [5], wherein at least one or more amino acid mutations have been introduced into the loop region of the Fc region at amino acid position 298 (EU numbering) or position 309 (EU numbering);

[26] the polypeptide of any one of [1] to [3], [5], and [25], wherein the amino acid modifications in the loop region of the Fc region are at least one or more amino acid modifications selected from the group consisting of substitution of the amino acid at position 298 (EU numbering) with Gly and substitution of the amino acid at position 309 (EU numbering) with Asp;

[27] a method for improving stability of a polypeptide comprising an antibody Fc region as compared to that of a parent polypeptide by introducing at least one amino acid modification to a loop region of the Fc region;

[28] the method of [27], wherein the stability is assessed or determined using melting temperature (Tm) as an index;

[29] a method for producing a polypeptide comprising an antibody Fc region, which has at least one amino acid modification in a loop region of the Fc region, and has improved stability as compared to that of a parent polypeptide, wherein the method comprises the steps of:
(a) introducing at least one amino acid modification to a polypeptide comprising an antibody Fc region at a loop region of the Fc region;
(b) determining the stability of the polypeptide modified in step (a); and
(c) selecting a polypeptide with improved stability as compared to that of the parent polypeptide;

[30] a method for producing a polypeptide comprising an antibody Fc region, which has at least one amino acid modification in a loop region of the Fc region, and has improved stability as compared to that of a parent polypeptide, wherein the method comprises the steps of:
(a) modifying a nucleic acid encoding the polypeptide so as to improve its stability as compared to that of the parent polypeptide;
(b) introducing the modified nucleic acid into a host cell and culturing the cell to induce expression of the nucleic acid; and
(c) collecting the polypeptide from the host cell culture;

[31] the method of any one of [27] to [30], wherein at least one or more amino acid mutations are introduced into the loop region of the Fc region at amino acid position(s) selected from the group consisting of position 234 (EU numbering), position 235 (EU numbering), position 236 (EU numbering), position 237 (EU numbering), position 238 (EU numbering), position 239 (EU numbering), position 247 (EU numbering), position 250 (EU numbering), position 265 (EU numbering), position 266 (EU numbering), position 267 (EU numbering), position 268 (EU numbering), position 269 (EU numbering), position 270 (EU numbering), position 271 (EU numbering), position 295 (EU numbering), position 296 (EU numbering), position 298 (EU numbering), position 300 (EU numbering), position 307 (EU numbering), position 309 (EU numbering), position 315 (EU numbering), position 324 (EU numbering), position 325 (EU numbering), position 326 (EU numbering), position 327 (EU numbering), position 329 (EU numbering), position 330 (EU numbering), position 333 (EU numbering), position 335 (EU numbering), position 337 (EU numbering), position 360 (EU numbering), position 385 (EU numbering), position 386 (EU numbering), position 387 (EU numbering), position 389 (EU numbering), position 428 (EU numbering), and position 433 (EU numbering);

[32] the method of any one of [27] to [31], which further comprises the step of introducing a modification to maintain or enhance FcγR-binding activity as compared to that of the parent polypeptide;

[33] the method of any one of [27] to [31], which further comprises the step of introducing a modification to reduce FcγR-binding activity as compared to that of the parent polypeptide;

[34] the method of any one of [27] to [33], wherein at least one or more amino acid mutations are introduced into the loop region of the Fc region at amino acid position(s) selected from the group consisting of position 234 (EU numbering), position 235 (EU numbering), position 239 (EU numbering), position 266 (EU numbering), position 267 (EU numbering), position 268 (EU numbering), position 269 (EU numbering), position 270 (EU numbering), position 295 (EU numbering), position 296 (EU numbering), position 298 (EU numbering), position 300 (EU numbering), position 324 (EU numbering), position 325 (EU numbering), position 326 (EU numbering), and position 330 (EU numbering);

[35] the method of any one of [27] to [32] and [34], wherein at least one or more amino acid mutations are introduced into the loop region of the Fc region at amino acid position(s) selected from the group consisting of position 234 (EU numbering), position 266 (EU numbering), position 268 (EU numbering), position 269 (EU numbering), position 270 (EU numbering), position 295 (EU numbering), position 300 (EU numbering), position 324 (EU numbering), position 326 (EU numbering), and position 330 (EU numbering);

[36] the method of any one of [27] to [32], [34], and [35], wherein the amino acid modification in the loop region of the Fc region is at least one or more amino acid modifications selected from the group consisting of substitution of the amino acid at position 234 (EU numbering) with Ile, substitution of the amino acid at position 266 (EU numbering) with Ile, substitution of the amino acid at position 268 (EU numbering) with Gln, substitution of the amino acid at position 269 (EU numbering) with Asp, substitution of the amino acid at position 270 (EU numbering) with Glu, substitution of the amino acid at position 295 (EU numbering) with Met or Leu, substitution of the amino acid at position 300 (EU numbering) with Glu, substitution of the amino acid at position 324 (EU numbering) with His, substitution of the amino acid at position 326 (EU numbering) with Ser or Ala, and substitution of the amino acid at position 330 (EU numbering) with His or Tyr;

[37] the method of any one of [27] to [31], [33], and [34], wherein at least one or more amino acid mutations are introduced into the loop region of the Fc region at amino acid position(s) selected from the group consisting of position 234 (EU numbering), position 235 (EU numbering), position 239 (EU numbering), position 267 (EU numbering), position 268 (EU numbering), position 270 (EU numbering), position 295 (EU numbering), position 296 (EU numbering), position 298 (EU numbering), and position 325 (EU numbering);

[38] the method of any one of [27] to [31], [33], [34], and [37], wherein the amino acid modification in the loop region of the Fc region is at least one or more amino acid modifications selected from the group consisting of substitution of the amino acid at position 234 (EU numbering) with Lys or Arg, substitution of the amino acid at position 235 (EU numbering) with Lys or Arg, substitution of the amino acid at position 239 (EU numbering) with Lys, substitution of the amino acid at position 267 (EU numbering) with Pro, substitution of the amino acid at position 268 (EU numbering) with Met or Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with Gly, His, or Met;

[39] the method of any one of [27] to [32], wherein at least one or more amino acid mutations are introduced into the loop region of the Fc region at amino acid position(s) selected from the group consisting of position 295 (EU numbering), position 326 (EU numbering), and position 330 (EU numbering);

[40] the method of any one of [27] to [32] and [39], wherein the amino acid modification in the loop region of the Fc region is at least one or more amino acid modifications selected from the group consisting of substitution of the amino acid at position 295 (EU numbering) with Met or Leu, substitution of the amino acid at position 326 (EU numbering) with Ser or Ala, and substitution of the amino acid at position 330 (EU numbering) with His or Tyr;

[41] the method of any one of [27] to [31] and [33], wherein at least one or more amino acid mutations are introduced into the loop region of the Fc region at amino acid position(s) selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering);

[42] the method of any one of [27] to [31], [33], and [41], wherein the amino acid modification in the loop region of the Fc region is at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys or Ser, substitution of the amino acid at position 268 (EU numbering) with Lys or His, substitution of the amino acid at position 270 (EU numbering) with Phe or Asp, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[43] the method of any one of [27] to [31] and [33], wherein at least one or more amino acid mutations are introduced into the loop region of the Fc region at amino acid position(s) selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering);

[44] the method of any one of [27] to [31], [33], and [43], wherein the amino acid modification in the loop region of the Fc region is at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[45] the method of any one of [27] to [31] and [33], wherein at least one or more amino acid mutations are introduced into the loop region of the Fc region at amino acid position(s) selected from the group consisting of position 234 (EU numbering), position 235 (EU numbering), position 239 (EU numbering), position 295 (EU numbering), position 296 (EU numbering), position 298 (EU numbering), and position 325 (EU numbering);

[46] the method of any one of [27] to [31], [33], and [45], wherein the amino acid modification in the loop region of the Fc region is at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[47] the method of any one of [27] to [31] and [33], wherein at least one or more amino acid mutations are introduced into the loop region of the Fc region at amino acid position(s) selected from the group consisting of position 234 (EU numbering), position 235 (EU numbering), position 268 (EU numbering), position 270 (EU numbering), position 295 (EU numbering), position 296 (EU numbering), position 298 (EU numbering), and position 325 (EU numbering);

[48] the method of any one of [27] to [31], [33], and [47], wherein the amino acid modification in the loop region of the Fc region is at least one or more amino acid modifications selected from the group consisting of substitution of the amino acid at position 234 (EU numbering) with Lys, substitution of the amino acid at position 235 (EU numbering) with Lys or Arg, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[49] the method of any one of [27] to [31] and [33], wherein at least one or more amino acid mutations are introduced into the loop region of the Fc region at amino acid position(s) selected from the group consisting of position 234 (EU numbering), position 235 (EU numbering), position 295 (EU numbering), position 296 (EU numbering), position 298 (EU numbering), and position 325 (EU numbering);

[50] the method of any one of [27] to [31], [33], and [49], wherein the amino acid modification in the loop region of the Fc region is at least one or more amino acid modifications selected from the group consisting of substitution of the amino acid at position 234 (EU numbering) with Lys, substitution of the amino acid at position 235 (EU numbering) with Lys or Arg, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly;

[51] the method of any one of [27] to [32], wherein at least one or more amino acid mutations are introduced into the loop region of the Fc region at amino acid position(s) selected from the group consisting of position 247 (EU numbering), position 250 (EU numbering), position 307 (EU numbering), position 309 (EU numbering), position 315 (EU numbering), position 360 (EU numbering), position 385 (EU numbering), position 386 (EU numbering), position 387 (EU numbering), position 389 (EU numbering), position 428 (EU numbering), and position 433 (EU numbering);

[52] the method of any one of [27] to [32] and [51], wherein the amino acid modification in the loop region of the Fc region is at least one or more amino acid modifications selected from the group consisting of substitution of the amino acid at position 247 (EU numbering) with Val, substitution of the amino acid at position 250 (EU numbering) with Phe, Ile, Met, Val, Trp, or Tyr, substitution of the amino acid at position 307 (EU numbering) with Ala, Gln, or Pro, substitution of the amino acid at position 309 (EU numbering) with Ala, Arg, or Pro, substitution of the amino acid at position 315 (EU numbering) with Ala, substitution of the amino acid at position 360 (EU numbering) with His, substitution of the amino acid at position 385 (EU numbering) with Asp, substitution of the amino acid at position 386 (EU numbering) with Pro, substitution of the amino acid at position 387 (EU numbering) with Glu, substitution of the amino acid at position 389 (EU numbering) with Ser, substitution of the amino acid at position 428 (EU numbering) with His, Trp, Tyr, or Phe, and substitution of the amino acid at position 433 (EU numbering) with Lys;

[53] the method of any one of [27] to [31] and [33], wherein at least one or more amino acid mutations are introduced into the loop region of the Fc region at amino acid position 298 (EU numbering) or position 309 (EU numbering);

[54] the method of any one of [27] to [31], [33], and [53], wherein the amino acid modification in the loop region of the Fc region is at least one or more amino acid modifications selected from the group consisting of substitution of the amino acid at position 298 with Gly and substitution of the amino acid at position 309 with Asp;

[55] the method of any one of [27] to [54], wherein the modification is modification in a polypeptide comprising an Fc region of human IgG;

[56] a nucleic acid encoding a polypeptide comprising an antibody Fc region, which has at least one amino acid modification in a loop region of the Fc region, and has improved stability as compared to that of a parent polypeptide;

[57] a vector comprising the nucleic acid of [56];

[58] a host cell transformed with the vector of [57];

[59] a pharmaceutical composition comprising the polypeptide of any one of [1] to [26], or a polypeptide produced by the method of any one of [27] to [55];

[60] an agent for treating or preventing an immune-inflammatory disease or cancer, which comprises the pharmaceutical composition of [59];

[61] the agent of [60], wherein the immune-inflammatory disease is rheumatoid arthritis, autoimmune hepatitis, autoimmune thyroiditis, autoimmune bullous dermatosis, autoimmune adrenocortical inflammation, autoimmune hemolytic anemia, autoimmune thrombocytopenic purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial pulmonary fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow's disease, juvenile diabetes, Addison's disease, myasthenia gravis, lenticular uveitis, systemic lupus erythematosus, allergic rhinitis, allergic dermatitis, ulcerative colitis, hypersensitivity, asthma, myodegeneration, cachexia, systemic scleroderma, localized scleroderma, Sjogren's syndrome, Behcet's disease, Reiter's syndrome, type I and type II diabetes, bone resorption disease, graft versus host reaction, ischemia reperfusion injury, atherosclerosis, brain trauma, multiple sclerosis, cerebral malaria, sepsis, septic shock, toxic shock syndrome, fever, malgias due to staining, aplastic anemia, hemolytic anemia, sudden thrombocytopenia, Goodpasture's syndrome, Guillain-Barre syndrome, Hashimoto's disease, pemphigus, IgA nephropathy, pollinosis, antiphospholipid antibody syndrome, polymyositis, Wegener's sarcoma, arteritis *nodosa*, mixed connective tissue disease, or fibromyalgia;

[62] the agent of [60], wherein the cancer is pancreatic cancer, prostate cancer, breast cancer, skin cancer, gastrointestinal cancer, lung cancer, hepatoma, cervical cancer, endometrial cancer, ovarian cancer, fallopian tube cancer, vaginal cancer, liver cancer, cholangioma, bladder cancer, ureteral cancer, thyroid cancer, adrenal carcinoma, renal cancer, other glandular tissue cancers, liposarcoma, leiomyosarcoma, rhabdomyosarcoma, synovial sarcoma, angiosarcoma, fibrosarcoma, malignant peripheral nerve tumor, gastrointestinal stromal tumor, desmoid tumor, Ewing's sarcoma, osteosarcoma, chondrosarcoma, leukemia, lymphoma, myeloma, or other solid organ tumors;

[63] a method for treating or preventing an immune-inflammatory disease or cancer, comprising administering to a subject the polypeptide of any one of [1] to [26], or a polypeptide produced by the method of any one of [27] to [55];

[64] the polypeptide of any one of [1] to [26] or a polypeptide produced by the method of any one of [27] to [55], for use in treatment or prevention of an immune-inflammatory disease or cancer;

[65] use of the polypeptide of any one of [1] to [26] or a polypeptide produced by the method of any one of [27] to [55] in the preparation of an agent for treating or preventing an immune-inflammatory disease or cancer; and

[66] a method for producing an agent for treating or preventing an immune-inflammatory disease or cancer, comprising the step of using the polypeptide of any one of [1] to [26] or a polypeptide produced by the method of any one of [27] to [55].

BRIEF DESCRIPTION OF THE DRAWINGS

FIG. 2-1 shows the chromatograms for aggregate content determination of TS20 to TS27 in which multiple modifications were combined.

FIG. 2-2 shows the chromatograms for aggregate content determination of TS28 to TS39 in which multiple modifications have been combined.

FIG. 2-3 shows the chromatograms for aggregate content determination of TS40 to TS43 in which multiple modifications have been combined.

FIG. 3 shows the relationship between the amino acid residues constituting the Fc region of IgG1, IgG2, IgG3, and IgG4 and Kabat EU numbering (which is herein also referred to as EU index).

FIG. 4 shows the sites of amino acid modification (L234-S239, D265-P271, Q295, Y296, S298, Y300, S324-S337; the shaded portions) in the loop region of the CH2 domain of Fc region B3 (SEQ ID NO: 16).

MODE FOR CARRYING OUT THE INVENTION

The present invention provides polypeptides having an antibody Fc region whose stability has been improved as compared to that of a parent polypeptide by introducing amino acid substitutions into a loop region of the Fc region.

Furthermore, the present invention provides methods for improving stability of a polypeptide having an antibody Fc region as compared to that of a parent polypeptide by introducing amino acid substitutions to a loop region of the antibody Fc region. Furthermore, the present invention provides methods for producing a polypeptide having an antibody Fc region whose stability has been improved as compared to that of a parent polypeptide by introducing amino acid substitutions to a loop region of the Fc region.

In the present invention, polypeptides generally refer to peptides or proteins of about ten or more amino acids in length. In addition, they are typically polypeptides of biological origin, but are not particularly limited. For example, they may be polypeptides composed of artificially designed sequences. They may also be any of naturally-occurring polypeptides, synthetic polypeptides, recombinant polypeptides, and such. Moreover, polypeptides may be antibodies. Preferred examples of polypeptides of the present invention include human IgG. When an antibody used is a human IgG, the type of its constant region is not limited, and human IgG isotypes (subclasses) such as IgG1, IgG2, IgG3, or IgG4 may be used.

Herein, "parent polypeptide" refers to a polypeptide which serves as a basis or reference in the production of polypeptides having an antibody Fc region of the present invention. More specifically, it can be a polypeptide having an antibody Fc region which has not yet been modified in at least one of the amino acids of the Fc region. The parent polypeptide in the present invention may be, for example, a polypeptide having an Fc region of a naturally-occurring IgG, or may be a polypeptide having an Fc region of IgG in which a modification other than the amino acid modifications of the present invention has been made to a naturally-occurring IgG.

Naturally-occurring IgGs refer to polypeptides that include an amino acid sequence identical to those of IgGs found in nature, and belong to a class of antibodies virtually encoded by immunoglobulin gamma genes. For example, naturally-occurring human IgG refers to naturally-occurring human IgG1, naturally-occurring human IgG2, naturally-occurring human IgG3, naturally-occurring human IgG4, and such. Naturally-occurring IgGs also include mutants and such that naturally occur from them.

Figures 1, 2:
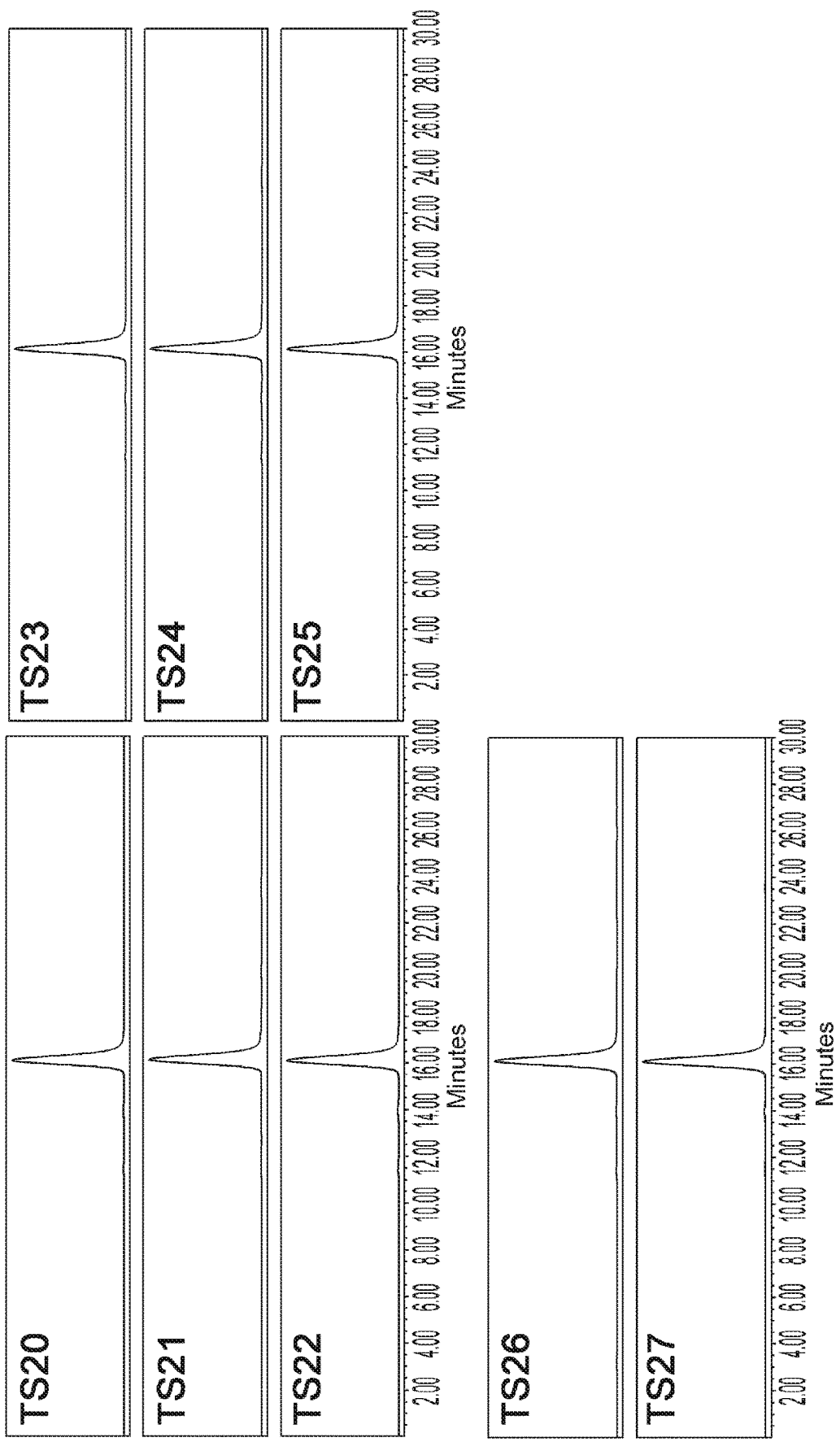
Figure 2:
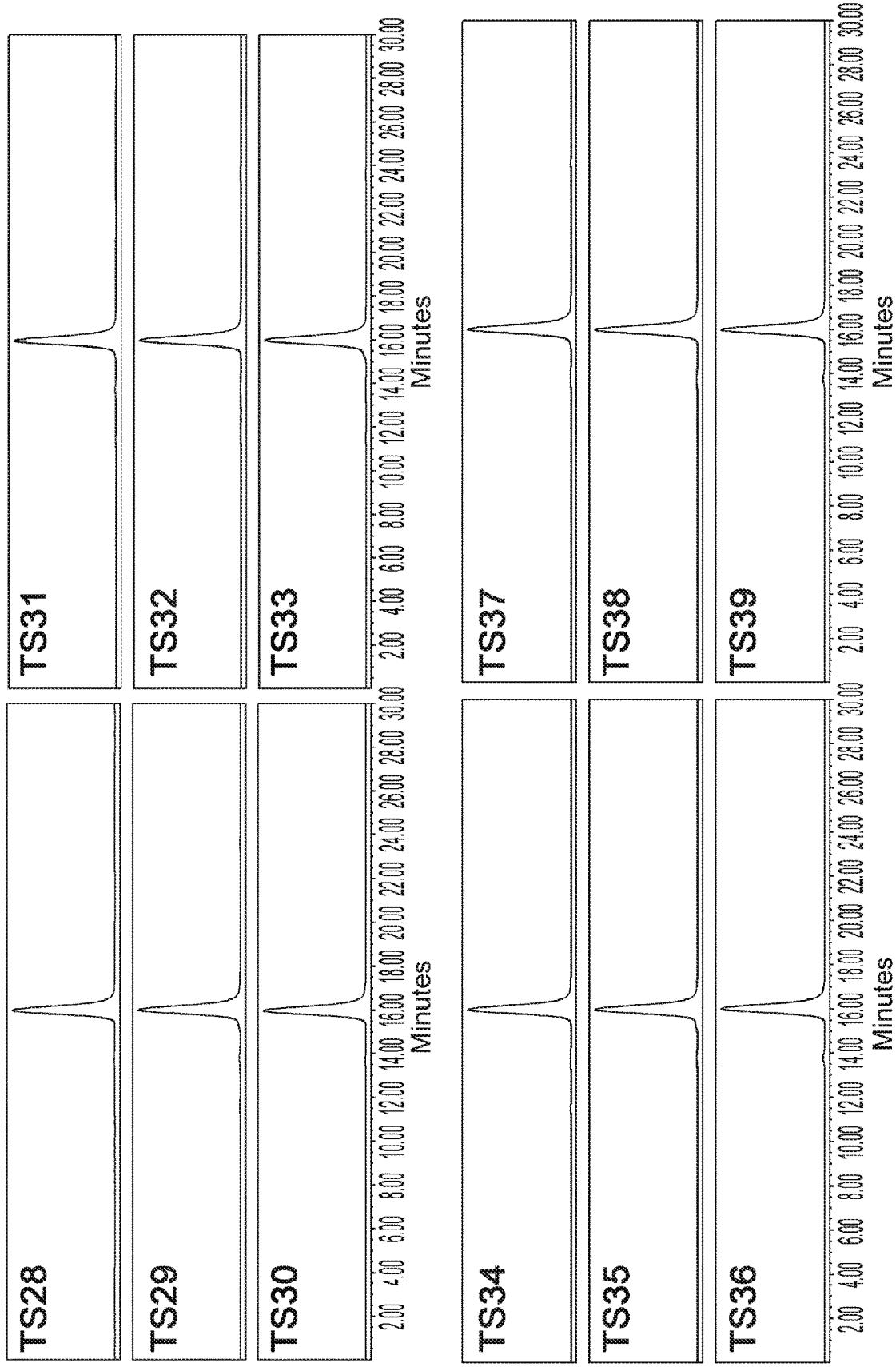
Figures 2, 3:
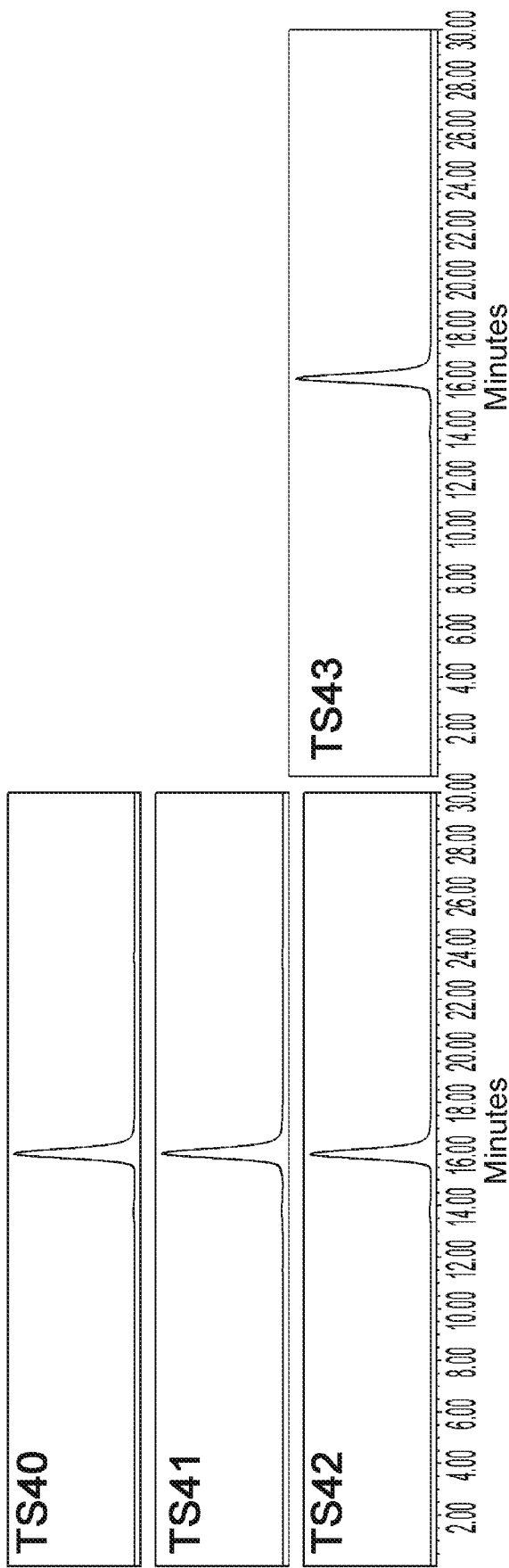

The Fc region of a naturally-occurring IgG refers to an Fc region containing an amino acid sequence identical to that of the Fc region derived from an IgG found in nature. The Fc regions of naturally-occurring IgGs are shown in FIG. 3 (SEQ ID NOs: 11 to 14), and refer to, for example, an Fc region derived from naturally-occurring human IgG1, an Fc region derived from naturally-occurring human IgG2, an Fc region derived from naturally-occurring human IgG3, an Fc region derived from naturally-occurring human IgG4, and such. The Fc regions of naturally-occurring IgGs also include mutants and such that naturally occur from them.

In the present invention, amino acid positions are defined according to Kabat (Sequences of Proteins of Immunological Interest (National Institute of Health, Bethesda, Md., 1987 and 1991). Herein, the sites of amino acid modifications in the antibody Fc region are shown according to EU numbering based on Kabat's amino acid positions.

In the present invention, portions linking α helices and β sheets are called loops, and there are no rules on their length or structure. In the present invention, a portion linking two β sheets in the CH2 domain is referred to as a loop, a loop region, a loop portion, or a loop structure. Specific amino acid positions of the loop region subjected to modification in the present invention are selected from the group consisting of position 234 (EU numbering), position 235 (EU numbering), position 236 (EU numbering), position 237 (EU numbering), position 238 (EU numbering), position 239 (EU numbering), position 247 (EU numbering), position 250 (EU numbering), position 265 (EU numbering), position 266 (EU numbering), position 267 (EU numbering), position 268 (EU numbering), position 269 (EU numbering), position 270 (EU numbering), position 271 (EU numbering), position 295 (EU numbering), position 296 (EU numbering), position 298 (EU numbering), position 300 (EU numbering), position 307 (EU numbering), position 309 (EU numbering), position 315 (EU numbering), position 324 (EU numbering), position 325 (EU numbering), position 326 (EU numbering), position 327 (EU numbering), position 329 (EU numbering), position 330 (EU numbering), position 333 (EU numbering), position 335 (EU numbering), position 337 (EU numbering), position 360 (EU numbering), position 385 (EU numbering), position 386 (EU numbering), position 387 (EU numbering), position 389 (EU numbering), position 428 (EU numbering), and position 433 (EU numbering).

"Fc region" refers to a region containing a fragment composed of a hinge portion or a part thereof, and CH2 and CH3 domains of an antibody molecule. An Fc region of IgG class means, for example, from cysteine at position 226 to the C terminus or from proline at position 230 to the C terminus according to Kabat's EU numbering (herein also referred to as EU index) (see FIG. 3), but is not limited thereto.

An Fc region may be obtained preferably by partially digesting IgG1, IgG2, IgG3, IgG4 monoclonal antibodies or such using a protease such as pepsin and then re-eluting a fraction adsorbed onto protein A column. The protease is not particularly limited as long as it can digest a full-length antibody so that Fab and F(ab')2 will be produced in a restrictive manner by appropriately setting the enzyme reaction conditions such as pH, and examples include pepsin and papain.

The polypeptides of the present invention include, for example, polypeptides having an Fc region with improved stability as compared to a parent polypeptide. Preferred embodiments of the polypeptides having an Fc region with improved stability as compared to a parent polypeptide include, for example, polypeptides in which at least one amino acid has been modified in a loop region of the Fc region.

The present invention provides antibody Fc regions containing an Fc region in which at least one or more amino acids have been modified in a loop region of the Fc region of an antibody (for example, human IgG (IgG1, IgG2, IgG3, and IgG4)) at amino acid positions selected from the group consisting of position 234 (EU numbering), position 235 (EU numbering), position 236 (EU numbering), position 237 (EU numbering), position 238 (EU numbering), position 239 (EU numbering), position 247 (EU numbering), position 250 (EU numbering), position 265 (EU numbering), position 266 (EU numbering), position 267 (EU numbering), position 268 (EU numbering), position 269 (EU numbering), position 270 (EU numbering), position 271 (EU numbering), position 295 (EU numbering), position 296 (EU numbering), position 298 (EU numbering), position 300 (EU numbering), position 307 (EU numbering), position 309 (EU numbering), position 315 (EU numbering), position 324 (EU numbering), position 325 (EU numbering), position 326 (EU numbering), position 327 (EU numbering), position 329 (EU numbering), position 330 (EU numbering), position 333 (EU numbering), position 335 (EU numbering), position 337 (EU numbering), position 360 (EU numbering), position 385 (EU numbering), position 386 (EU numbering), position 387 (EU numbering), position 389 (EU numbering), position 428 (EU numbering), and position 433(EU numbering) of the IgG. For example, a polypeptide with improved stability as compared to a parent polypeptide can be provided by introducing the above-mentioned modifications to human IgG.

The present invention also provides antibody Fc regions containing an Fc region in which at least one or more amino acid mutations have been introduced into a loop region of the Fc region of an antibody (for example, human IgG (IgG1, IgG2, IgG3, and IgG4)) at amino acid positions selected from the group consisting of position 234 (EU numbering), position 235 (EU numbering), position 239 (EU numbering), position 266 (EU numbering), position 267 (EU numbering), position 268 (EU numbering), position 269 (EU numbering), position 270 (EU numbering), position 295 (EU numbering), position 296 (EU numbering), position 298 (EU numbering), position 300 (EU numbering), position 324 (EU numbering), position 325 (EU numbering), position 326 (EU numbering), and position 330 (EU numbering) of the IgG.

Herein, "stability" means, for example, thermodynamic stability of a polypeptide, but is not limited thereto. Thermodynamic stability of a polypeptide can be assessed or determined, for example, by using the melting temperature (Tm) of a CH2 domain as an index. Thus, polypeptides of the present invention are preferably assessed or judged using melting temperature (Tm) as an index. Tm can be measured by CD (circular dichroism), DSC (differential scanning calorimetry), and DSF (differential scanning fluorimetry).

The above-mentioned methods used for evaluating thermal stability can evaluate the thermal stability of the CH2, CH3, and Fab domains individually, when a sample in the form of IgG is measured. When CH2 and CH3 of the Fc region are compared, CH2 has lower thermal stability; therefore, improving the thermal stability of CH2 may lead to improvement of thermal stability of the Fc region.

Furthermore, an IgG keeps a highly-controlled conformation, and the conformation and physical stability of the respective domains affect each other. That is, a modification introduced into a certain domain may have an effect on a different domain, resulting in changes in the conformation and physical stability of the entire IgG. Therefore, when evaluating effects of introduced modifications, a sample is desirably evaluated in the form of IgG. For the above-mentioned reasons, evaluation of thermal stability of the CH2 domain in the present specification has been carried out using modified antibodies produced in the form of IgG.

When CD is used, Tm is determined by observing the mean residue molar ellipticity ($\theta$) changing with rising temperature. Devices for measuring CD include, for example, a circular dichroism dispersion meter (JASCO Corporation). When CD spectra are monitored at a suitable wavelength (for example, 208 nm or 222 nm) while increasing the temperature, $\theta$ increases at a certain temperature, and becomes constant at temperatures thereafter. The temperature corresponding to the midpoint between the $\theta$ at low temperatures and the $\theta$ at high temperatures is determined as Tm. For the measurement, for example, protein solutions prepared using citric acid, Tris, phosphate solution, and such may be used, and such solutions can be used at a concentration of several hundred µg/mL.

When DSC is used, Tm is determined by observing the amount of heat changing with rising temperature. Measurement devices for DSC include MicroCal VP-DSC and Micro Cal Capillary DSC (both from GE Healthcare). When a protein solution and a buffer are enclosed in measurement cells, and temperature differences between the cells are measured while raising the temperature, the reaction becomes endothermic at a certain temperature. This temperature is determined as Tm. For the measurement, for example, protein solutions prepared using citrate buffer, TBS, PBS, histidine buffer, and such may be used, and such solutions can be used at a concentration of several ten µg/mL to several hundred µg/mL.

When DSF is used, Tm is determined by observing exposure of hydrophobic residues due to rising temperature, using a fluorescent reagent (for example, SYPRO Orange) that specifically binds to hydrophobic residues. A protein solution and a fluorescence reagent are mixed at an appropriate ratio. When fluorescence intensity is measured while raising the temperature using an RT-PCR instrument, an increase in the fluorescence intensity is observed at a certain temperature. This temperature is determined as Tm. Measurement devices for DSF include Rotor-Gene Q (QIAGEN), and CFX96 real-time PCR analysis system (Bio-Rad). For the measurements, for example, protein solutions prepared using PBS, histidine buffer, and such may be used, and such solutions can be used at a concentration of several ten µg/mL to several hundred µg/mL.

Herein, "the stability of a polypeptide is improved" means that, for example, as compared to the Tm of the CH2 domain in the Fc region of a parent polypeptide used as a control determined according to the above-mentioned methods, the Tm of the CH2 domain in the Fc region of a test polypeptide is improved by 0.1 degrees or more, preferably 0.2 degrees or more, 0.3 degrees or more, 0.4 degrees or more, 0.5 degrees or more, 1 degree or more, 2 degrees or more, 3 degrees or more, 4 degrees or more, 5 degrees or more, 10 degrees or more, or 20 degrees or more.

Furthermore, the polypeptides of the present invention may also be polypeptides having an Fc region with not only improved stability as compared to that of a parent polypeptide but also maintained or enhanced binding activity to an Fcγ receptor (which may also be herein referred to as FcγR) as compared to that of the parent polypeptide. In the present invention, examples of the polypeptides having an Fc region with not only improved stability compared to that of a parent polypeptide but also maintained or enhanced FcγR-binding activity as compared to that of the parent polypeptide include polypeptides having the amino acid positions described in any of TS1-TS8, TS20-TS27, TS44-TS50, TS52-TS55, or TS57-TS67 as shown below in the Examples.

TS1-TS8

Examples of the polypeptide with maintained or enhanced FcγR-binding activity as compared to that of its parent polypeptide include polypeptides in which at least one or more amino acid mutations have been introduced into the loop region of the Fc region at amino acid positions selected from the group consisting of position 234 (EU numbering), position 266 (EU numbering), position 268 (EU numbering), position 269 (EU numbering), position 270 (EU numbering), position 295 (EU numbering), position 300 (EU numbering), position 324 (EU numbering), position 326 (EU numbering), and position 330 (EU numbering).

Preferred polypeptides in this embodiment include polypeptides in which the positions of amino acid modification in the loop region of the Fc region are position 234 (EU numbering), position 266 (EU numbering), position 268 (EU numbering), position 269 (EU numbering), position 270 (EU numbering), position 295 (EU numbering), position 300 (EU numbering), position 324 (EU numbering), position 326 (EU numbering), and position 330 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Ile, substitution of the amino acid at position 266 (EU numbering) with Ile, substitution of the amino acid at position 268 (EU numbering) with Gln, substitution of the amino acid at position 269 (EU numbering) with Asp, substitution of the amino acid at position 270 (EU numbering) with Glu, substitution of the amino acid at position 295 (EU numbering) with Met or Leu, substitution of the amino acid at position 300 (EU numbering) with Glu, substitution of the amino acid at position 324 (EU numbering) with His, substitution of the amino acid at position 326 (EU numbering) with Ser or Ala, and substitution of the amino acid at position 330 (EU numbering) with His or Tyr.

Even more preferred polypeptides in this embodiment include polypeptides in which the amino acid modifications in the loop region of the Fc region are substitution of the amino acid at position 234 (EU numbering) with Ile, substitution of the amino acid at position 266 (EU numbering) with Ile, substitution of the amino acid at position 268 (EU numbering) with Gln, substitution of the amino acid at position 269 (EU numbering) with Asp, substitution of the amino acid at position 270 (EU numbering) with Glu, substitution of the amino acid at position 295 (EU numbering) with Met or Leu, substitution of the amino acid at position 300 (EU numbering) with Glu, substitution of the amino acid at position 324 (EU numbering) with His, substitution of the amino acid at position 326 (EU numbering) with Ser or Ala, and substitution of the amino acid at position 330 (EU numbering) with His or Tyr.

TS20-TS27

Examples of the polypeptide with maintained or enhanced FcγR-binding activity compared to that of its parent polypeptide include polypeptides in which at least one or more amino acid mutations have been introduced to the loop region of the Fc region at amino acid positions selected from the group consisting of position 295 (EU numbering), position 326 (EU numbering), and position 330 (EU numbering).

Preferred polypeptides in this embodiment are polypeptides in which the positions of amino acid modification in the loop region of the Fc region are position 295 (EU numbering), position 326 (EU numbering), and position 330 (EU numbering).

More preferred polypeptides in this embodiment include polypeptides in which the amino acid modifications in the loop region of the Fc region are at least one or more amino acid modifications selected from the group consisting of substitution of the amino acid at position 295 (EU numbering) with Met or Leu, substitution of the amino acid at position 326 (EU numbering) with Ser or Ala, and substitution of the amino acid at position 330 (EU numbering) with His or Tyr.

Even more preferred polypeptides in this embodiment include polypeptides in which the amino acid modifications in the loop region of the Fc region are substitution of the amino acid at position 295 (EU numbering) with Met or Leu, substitution of the amino acid at position 326 (EU numbering) with Ser or Ala, and substitution of the amino acid at position 330 (EU numbering) with His or Tyr.

TS44-TS50, TS52-TS55, TS57-TS67

Examples of the polypeptide with maintained or enhanced FcγR-binding activity compared to that of its parent polypeptide include polypeptides in which at least one or more amino acid mutations have been introduced to the loop region of the Fc region at amino acid positions selected from the group consisting of position 247 (EU numbering), position 250 (EU numbering), position 307 (EU numbering), position 309 (EU numbering), position 315 (EU numbering), position 360 (EU numbering), position 385 (EU numbering), position 386 (EU numbering), position 387 (EU numbering), position 389 (EU numbering), position 428 (EU numbering), and position 433(EU numbering).

Preferred polypeptides in this embodiment are polypeptides in which the positions of amino acid modification in the loop region of the Fc region are position 247 (EU numbering), position 250 (EU numbering), position 307 (EU numbering), position 309 (EU numbering), position 315 (EU numbering), position 360 (EU numbering), position 385 (EU numbering), position 386 (EU numbering), position 387 (EU numbering), position 389 (EU numbering), position 428 (EU numbering), and position 433(EU numbering).

More preferred polypeptides in this embodiment include polypeptides in which the amino acid modifications in the loop region of the Fc region are at least one or more amino acid modifications selected from the group consisting of substitution of the amino acid at position 247 (EU numbering) with Val, substitution of the amino acid at position 250 (EU numbering) with Phe, Ile, Met, Val, Trp, or Tyr, substitution of the amino acid at position 307 (EU numbering) with Ala, Gln, or Pro, substitution of the amino acid at position 309 (EU numbering) with Ala, Arg, or Pro, substitution of the amino acid at position 315 (EU numbering) with Ala, substitution of the amino acid at position 360 (EU numbering) with His, substitution of the amino acid at position 385 (EU numbering) with Asp, substitution of the amino acid at position 386 (EU numbering) with Pro, substitution of the amino acid at position 387 (EU numbering) with Glu, substitution of the amino acid at position 389 (EU numbering) with Ser, substitution of the amino acid at position 428 (EU numbering) with His, Trp, Tyr, or Phe, and substitution of the amino acid at position 433 (EU numbering) with Lys.

Even more preferred polypeptides in this embodiment include polypeptides in which the amino acid modifications in the loop region of the Fc region are substitution of the amino acid at position 247 (EU numbering) with Val, substitution of the amino acid at position 250 (EU numbering) with Phe, Ile, Met, Val, Trp, or Tyr, substitution of the amino acid at position 307 (EU numbering) with Ala, Gln, or Pro, substitution of the amino acid at position 309 (EU numbering) with Ala, Arg, or Pro, substitution of the amino acid at position 315 (EU numbering) with Ala, substitution of the amino acid at position 360 (EU numbering) with His, substitution of the amino acid at position 385 (EU numbering) with Asp, substitution of the amino acid at position 386 (EU numbering) with Pro, substitution of the amino acid at position 387 (EU numbering) with Glu, substitution of the amino acid at position 389 (EU numbering) with Ser, substitution of the amino acid at position 428 (EU numbering) with His, Trp, Tyr, or Phe, and substitution of the amino acid at position 433 (EU numbering) with Lys.

For example, when the polypeptide is an antibody, it may preferably be used as a cancer antibody, for which its effector functions are important.

Furthermore, a polypeptide of the present invention may also be a polypeptide having an Fc region with not only improved stability compared to that of its parent polypeptide but also decreased binding activity to an Fcγ receptor as compared to that of the parent polypeptide. In the present invention, examples of the polypeptide having an Fc region with not only improved stability compared to that of its parent polypeptide but also decreased FcγR-binding activity as compared to that of the parent polypeptide include polypeptides having the amino acid modification region of TS9-TS19, TS28-TS43, TS51, or TS56 as shown below in the Examples.

TS9-TS19

Examples of the polypeptide with decreased FcγR-binding activity as compared to that of its parent polypeptide include polypeptides in which at least one or more amino acid mutations have been introduced to the loop region of the Fc region at amino acid positions selected from the group consisting of position 234 (EU numbering), position 235 (EU numbering), position 239 (EU numbering), position 267 (EU numbering), position 268 (EU numbering), position 270 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 239 (EU numbering), position 267 (EU numbering), position 268 (EU numbering), position 270 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys or Arg, substitution of the amino acid at position 235 (EU numbering) with Lys or Arg, substitution of the amino acid at position 239 (EU numbering) with Lys, substitution of the amino acid at position 267 (EU numbering) with Pro, substitution of the amino acid at position 268 (EU numbering) with Met or Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with Gly, His, or Met.

Even more preferred polypeptides in this embodiment include polypeptides in which the amino acid modifications in the loop region of the Fc region are substitution of the amino acid at position 234 (EU numbering) with Lys or Arg, substitution of the amino acid at position 235 (EU numbering) with Lys or Arg, substitution of the amino acid at position 239 (EU numbering) with Lys, substitution of the amino acid at position 267 (EU numbering) with Pro, substitution of the amino acid at position 268 (EU numbering) with Met or Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with Gly, His, or Met.

TS28-TS34

Examples of the polypeptide with decreased FcγR-binding activity compared to that of its parent polypeptide include polypeptides in which at least one or more amino acid mutations have been introduced to the loop region of the Fc region at amino acid positions selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys or Ser, substitution of the amino acid at position 268 (EU numbering) with Lys or His, substitution of the amino acid at position 270 (EU numbering) with Phe or Asp, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

Even more preferred polypeptides in this embodiment are polypeptides in which the amino acid modifications in the loop region of the Fc region are substitution of the amino acid at position 234 (EU numbering) with Lys, substitution of the amino acid at position 235 (EU numbering) with Lys or Arg, substitution of the amino acid at position 239 (EU numbering) with Lys or Ser, substitution of the amino acid at position 268 (EU numbering) with Lys or His, substitution of the amino acid at position 270 (EU numbering) with Phe or Asp, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

TS28, TS29, TS36, TS37

Examples of the polypeptide with decreased FcγR-binding activity as compared to that of its parent polypeptide include polypeptides in which at least one or more amino acid mutations have been introduced to the loop region of the Fc region at amino acid positions selected from the group consisting of position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 239 (EU numbering), position 268 (EU numbering), position 270 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

Even more preferred polypeptides in this embodiment are polypeptides in which the amino acid modifications in the loop region of the Fc region are substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

TS30, TS31, TS38, TS39

Examples of the polypeptide with decreased FcγR-binding activity compared with that of a parent polypeptide include polypeptides in which at least one or more amino acid mutations have been introduced to the loop region of the Fc region at amino acid positions selected from the group consisting of position 234 (EU numbering), position 235 (EU numbering), position 239 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 239 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

Even more preferred polypeptides in this embodiment are polypeptides in which the amino acid modifications in the loop region of the Fc region are substitution of the amino acid at position 234 (EU numbering) with Lys, substitution of the amino acid at position 235 (EU numbering) with Lys or Arg, substitution of the amino acid at position 239 (EU numbering) with Lys, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

TS32, TS33, TS40, TS41

Examples of the polypeptide with decreased FcγR-binding activity as compared to that of its parent polypeptide include polypeptides in which at least one or more amino acid mutations have been introduced to the loop region of the Fc region at amino acid positions selected from the group consisting of position 234 (EU numbering), position 235 (EU numbering), position 268 (EU numbering), position 270 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 268 (EU numbering), position 270 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

Even more preferred polypeptides in this embodiment are polypeptides in which the amino acid modifications in the loop region of the Fc region are substitution of the amino acid at position 234 (EU numbering) with Lys, substitution of the amino acid at position 235 (EU numbering) with Lys or Arg, substitution of the amino acid at position 268 (EU numbering) with Lys, substitution of the amino acid at position 270 (EU numbering) with Phe, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

TS34, TS35, TS42, TS43

Examples of the polypeptide with decreased FcγR-binding activity compared to that of its parent polypeptide include polypeptides in which at least one or more amino acid mutations have been introduced to the loop region of the Fc region at amino acid positions selected from the group consisting of position 234 (EU numbering), position 235 (EU numbering), position 295 (EU numbering), position 296 (EU numbering), position 298 (EU numbering), and position 325 (EU numbering).

Preferred polypeptides in this embodiment are polypeptides in which the positions of amino acid modification in the loop region of the Fc region are position 234 (EU numbering), position 235 (EU numbering), position 295 (EU numbering), position 296 (EU numbering), position 298 (EU numbering), and position 325 (EU numbering).

More preferred polypeptides in this embodiment include polypeptides in which the amino acid modifications in the loop region of the Fc region are at least one or more amino acid modifications selected from the group consisting of substitution of the amino acid at position 234 (EU numbering) with Lys, substitution of the amino acid at position 235 (EU numbering) with Lys or Arg, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

Even more preferred polypeptides in this embodiment are polypeptides in which the amino acid modifications in the loop region of the Fc region are substitution of the amino acid at position 234 (EU numbering) with Lys, substitution of the amino acid at position 235 (EU numbering) with Lys or Arg, substitution of the amino acid at position 295 (EU numbering) with Met, substitution of the amino acid at position 296 (EU numbering) with Gly, substitution of the amino acid at position 298 (EU numbering) with Gly, and substitution of the amino acid at position 325 (EU numbering) with His or Gly.

TS51, TS56

Examples of the polypeptide with decreased FcγR-binding activity compared to that of its parent polypeptide include polypeptides in which at least one or more amino acid mutations have been introduced to the loop region of the Fc region at amino acid position 298 (EU numbering) and position 309 (EU numbering).

Preferred polypeptides in this embodiment include polypeptides in which the positions of amino acid modification in the loop region of the Fc region are position 298 (EU numbering) and position 309 (EU numbering).

More preferred polypeptides in this embodiment include polypeptides in which the amino acid modifications in the loop region of the Fc region are at least one or more amino acid modifications selected from the group consisting of substitution of the amino acid at position 298 (EU numbering) with Gly and substitution of the amino acid at position 309 with Asp.

Even more preferred polypeptides in this embodiment include polypeptides in which the amino acid modifications in the loop region of the Fc region are substitution of the amino acid at position 298 (EU numbering) with Gly and substitution of the amino acid at position 309 with Asp.

For example, when the polypeptide is an antibody, it may preferably be used as a neutralizing antibody.

"Fcγ receptors" refers to receptors that may bind to the Fc region of IgG1, IgG2, IgG3, and IgG4 monoclonal antibodies, and practically means any member of the family of proteins encoded by the Fcγ receptor genes. In humans, this family includes FcγRI (CD64) including isoforms FcγRIa, FcγRIb, and FcγRIc; FcγRII (CD32) including isoforms FcγRIIa (including allotypes H131 (type H) and R131 (type R)), FcγRIIb (including FcγRIIb-1 and FcγRIIb-2), and FcγRIIc; and FcγRIII (CD16) including isoforms FcγRIIIa (including allotypes V158 and F158), and FcγRIIIb (including allotypes FcγRIIIb-NA1 and FcγRIIIb-NA2), and any human FcγRs, FcγR isoforms or allotypes yet to be discovered, but is not limited thereto. The FcγR in the present invention includes not only human-derived FcγRs, but also mouse, rat, rabbit, and monkey-derived FcγRs but is not limited thereto, and may be derived from any organism. Mouse FcγRs include FcγRI (CD64), FcγRII (CD32), FcγRIII (CD16), and FcγRIII-2 (CD16-2), and any mouse FcγRs, or FcγR isoforms or allotypes yet to be discovered, but are not limited thereto. Preferred examples of Fcγ receptors in the present invention include human FcγI (CD64), FcγIIA (CD32), FcγIIB (CD32), FcγIIIA (CD16), and/or FcγIIIB (CD16).

The polynucleotide sequence and amino acid sequence of FcγI are set forth in SEQ ID NOs: 1 (NM_000566.3) and 2 (NP_000557.1), respectively;

the polynucleotide sequence and amino acid sequence of FcγIIA are set forth in SEQ ID NOs: 3 (BC020823.1) and 4 (AAH20823.1), respectively;
the polynucleotide sequence and amino acid sequence of FcγIIB are set forth in SEQ ID NOs: 5 (BC146678.1) and 6 (AAI46679.1), respectively;
the polynucleotide sequence and amino acid sequence of FcγIIIA are set forth in SEQ ID NOs: 7 (BC033678.1) and 8 (AAH33678.1), respectively; and
the polynucleotide sequence and amino acid sequence of FcγIIIB are set forth in SEQ ID NOs 9 (BC128562.1) and 10 (AAI28563.1), respectively (the RefSeq Registration number is indicated inside the parentheses).

In FcγRIIa, there are two allotypes: one where the amino acid at position 131 of FcγRIIa is histidine (type H) and the other where this amino acid is substituted with arginine (type R) (J. Exp. Med, 172: 19-25, 1990).

In the present invention, whether or not the binding activity of a polypeptide or an Fc region of the present invention towards each type of FcγR is decreased, or maintained or enhanced can be determined, for example, as shown in the present Examples. Specifically, it can be determined by using BIACORE, which is a device for interaction analysis based on the surface plasmon resonance (SPR) phenomenon, and observing whether there is a decrease or an increase in the dissociation constant (KD) value obtained by allowing each type of FcγR to flow as an analyte over a sensor chip onto which a polypeptide (antibody) has been immobilized or captured with Protein A, antigen peptide or such, or whether there is an increase or a decrease in the amount of change in the sensorgram value before and after allowing each type of FcγR to flow as an analyte over a sensor chip onto which a polypeptide (antibody) has been immobilized or captured with Protein A, antigen peptide or such.

Specifically, the binding activity of an Fc region towards an Fcγ receptor can be measured by the Amplified Luminescent Proximity Homogeneous Assay (ALPHA) Screen, the BIACORE method which utilizes the surface plasmon resonance (SPR) phenomena, or such, in addition to ELISA or fluorescence activated cell sorting (FACS) (Proc. Natl. Acad. Sci. USA (2006) 103 (11): 4005-4010).

ALPHA Screen is performed by ALPHA technology which uses two beads, a donor and an acceptor, based on the following principles. Luminescent signals are detected only when molecules bound to donor beads physically interact with molecules bound to the acceptor beads, and the two beads are in close proximity to each other. Laser-excited photosensitizer in the donor beads converts ambient oxygen to excited-state singlet oxygen. Singlet oxygen is dispersed around the donor beads, and when it reaches the adjacent acceptor beads, chemiluminescent reaction is induced in the beads, and light is ultimately emitted. When the molecules bound to the donor beads do not interact with the molecules bound to the acceptor beads, the chemiluminescent reaction does not take place because singlet oxygen produced by the donor beads does not reach the acceptor beads.

For example, a biotinylated polypeptide complex is bound to the donor beads, and Fcγ receptor tagged with glutathione S transferase (GST) is linked to the acceptor beads. In the absence of a competing polypeptide complex having a mutant Fc region, the polypeptide complex having a wild-type Fc region interacts with the Fcγ receptor and produces 520-620 nm signals. The polypeptide complex having an untagged mutant Fc region competes with the polypeptide complex having a wild-type Fc region for interaction with the Fcγ receptor. Relative binding affinity can be determined by quantifying the decrease in fluorescence observed as a result of the competition.

Biotinylation of polypeptide complexes such as antibodies using Sulfo-NHS-biotin and such is well known. The method of expressing the Fcγ receptor and GST in a cell carrying a fusion gene produced by fusing a polynucleotide encoding the Fcγ receptor in frame with a polynucleotide encoding GST in an expressible vector, and performing purification using a glutathione column is appropriately adopted as a method for tagging an Fcγ receptor with GST. The obtained signals are preferably analyzed, for example, by fitting them to a one-site competition model which uses a non-linear regression analysis using software such as GRAPHPAD PRISM (GraphPad, San Diego).

One of the substances (the ligand) in observation of an interaction is immobilized onto a gold thin film on a sensor chip, and by shining light from the reverse side of the sensor chip so that total reflection takes place at the interface between the gold thin film and glass, a portion of reduced reflection intensity is formed in part of the reflected light (SPR signal). When the other one of the substances (the analyte) in observation of an interaction is made to flow on the sensor chip surface and the ligand binds to the analyte, the mass of the immobilized ligand molecule increases and the refractive index of the solvent on the sensor chip surface changes. The position of the SPR signal shifts as a result of this change in refractive index (on the other hand, the signal position returns when this binding dissociates). The Biacore system indicates the amount of shift mentioned above, or more specifically the time variable of mass by plotting the change in mass on the sensor chip surface on the ordinate as the measurement data (sensorgram). The amount of analyte bound to the ligand trapped on the sensor chip surface is determined from the sensorgram. Kinetic parameters such as association rate constants (ka) and dissociation rate constants (kd) are determined from the curves of the sensorgram, and the dissociation constants (KD) are determined from the ratio of these constants. In the BIACORE method, a method for measuring inhibition is preferably used. An example of the method for measuring inhibition is described in Proc. Natl. Acad. Sci USA (2006) 103 (11): 4005-4010.

In the present invention, a polypeptide with decreased FcγR-binding activity (a polypeptide whose binding activity to FcγR is decreased) refers to a polypeptide having at least one amino acid modification in the Fc region of a parent polypeptide (also called a polypeptide variant) which, when assayed in substantially the same amount as the parent polypeptide, binds to at least one type of FcγR with a substantially lower binding affinity than the parent polypeptide.

For example, when the amount of the parent polypeptide bound to each FcγR, as measured by the aforementioned method, is taken as 100, the amount of the polypeptide variant bound to each FcγR (hereinafter referred to as "binding amount ratio") is preferably decreased to 80 or less, preferably 50 or less, 40 or less, 30 or less, 20 or less, or particularly preferably 10 or less, 5 or less, 4 or less, 3 or less, 2 or less, 1 or less, or 0.1 or less.

In the present invention, a polypeptide with enhanced FcγR-binding activity (a polypeptide whose binding activity to FcγR is enhanced) refers to a polypeptide variant which, when assayed in substantially the same amount as the parent polypeptide, binds to at least one type of FcγR with a substantially higher binding affinity than the parent polypeptide.

For example, when the amount of the parent polypeptide bound to each FcγR, as measured by the aforementioned method, is taken as 100, the amount of the polypeptide variant bound to each FcγR (hereinafter referred to as "binding amount ratio") is preferably increased to 120 or more, 150 or more, 200 or more, or 300 or more.

A polypeptide with unchanged (maintained) FcγR-binding activity (a polypeptide whose binding activity to FcγR is unchanged (maintained)) refers to a polypeptide having at least one amino acid modification in the Fc region of a parent polypeptide (also called a polypeptide variant) which, when assayed in substantially the same amount as the parent polypeptide, binds to FcγR with a binding affinity substantially unchanged from or equivalent to that of the parent polypeptide.

For example, when the amount of the parent polypeptide bound to each FcγR, as measured by the aforementioned method, is taken as 100, the amount of the polypeptide variant bound to each FcγR (hereinafter referred to as "binding amount ratio") is preferably 80 or more and 120 or less.

In the present invention, polypeptides (for example, human IgG) containing the above-mentioned modifications of the present invention may be further modified in other parts of the Fc region.

For example, such modifications to other parts of the Fc region include substituting Pro at position 238 (EU numbering) with Asp and/or substituting Leu at position 328 (EU numbering) with Glu in human IgG (IgG1, IgG2, IgG3, and IgG4). Polypeptides with maintained or decreased binding activities towards FcγRI, FcγRIIIa, and both R and H allotypes of FcγRIIa, as well as enhanced FcγRIIb-binding activity in comparison with a parent polypeptide can be provided by introducing alteration of substituting Pro at position 238 (EU numbering) with Asp or substituting Leu at position 328 (EU numbering) with Glu in human IgG.

Further alterations of the Fc region can be added to human IgG containing alterations by which Pro at position 238 (EU numbering) has been substituted with Asp and/or Leu at position 328 (EU numbering) has been substituted with Glu. Here, alteration refers to any one of, or a combination of amino acid substitutions, deletions, additions, and insertions. Additional alterations can be further included in addition to these alterations. An additional alteration can be selected from any one of, or combinations of amino acid substitutions, deletions, or modifications. For example, alterations that further decrease binding activity towards FcγRI, FcγRIIa (type H), FcγRIIa (type R), or FcγRIIIa can be added.

Preferred alterations among them are those that only reduce the binding activity towards FcγRI, FcγRIIa (type H), FcγRIIa (type R), or FcγRIIIa without reducing the binding activity toward FcγRIIb. Preferred examples of such alterations include the following amino acid substitutions:

substitution of Gly at position 237 (EU numbering) with Trp,
substitution of Gly at position 237 (EU numbering) with Phe,
substitution of Pro at position 238 (EU numbering) with Phe,
substitution of Asn at position 325 (EU numbering) with Met,
substitution of Ser at position 267 (EU numbering) with Ile,
substitution of Leu at position 328 (EU numbering) with Asp,
substitution of Ser at position 267 (EU numbering) with Val,
substitution of Leu at position 328 (EU numbering) with Trp,
substitution of Ser at position 267 (EU numbering) with Gln,
substitution of Ser at position 267 (EU numbering) with Met,
substitution of Gly at position 236 (EU numbering) with Asp,
substitution of Ala at position 327 (EU numbering) with Asn,
substitution of Asn at position 325 (EU numbering) with Ser,
substitution of Leu at position 235 (EU numbering) with Tyr,
substitution of Val at position 266 (EU numbering) with Met,
substitution of Leu at position 328 (EU numbering) with Tyr,
substitution of Leu at position 235 (EU numbering) with Trp,
substitution of Leu at position 235 (EU numbering) with Phe,
substitution of Ser at position 239 (EU numbering) with Gly,
substitution of Ala at position 327 (EU numbering) with Glu,
substitution of Ala at position 327 (EU numbering) with Gly,
substitution of Pro at position 238 (EU numbering) with Leu,
substitution of Ser at position 239 (EU numbering) with Leu,
substitution of Leu at position 328 (EU numbering) with Thr,
substitution of Leu at position 328 (EU numbering) with Ser,
substitution of Leu at position 328 (EU numbering) with Met,
substitution of Pro at position 331 (EU numbering) with Trp,
substitution of Pro at position 331 (EU numbering) with Tyr,
substitution of Pro at position 331 (EU numbering) with Phe,
substitution of Ala at position 327 (EU numbering) with Asp,
substitution of Leu at position 328 (EU numbering) with Phe,
substitution of Pro at position 271 (EU numbering) with Leu,
substitution of Ser at position 267 (EU numbering) with Glu,
substitution of Leu at position 328 (EU numbering) with Ala,
substitution of Leu at position 328 (EU numbering) with Ile,
substitution of Leu at position 328 (EU numbering) with Gln,
substitution of Leu at position 328 (EU numbering) with Val,
substitution of Lys at position 326 (EU numbering) with Trp,
substitution of Lys at position 334 (EU numbering) with Arg, substitution of His at position 268 (EU numbering) with Gly,
substitution of His at position 268 (EU numbering) with Asn,
substitution of Ser at position 324 (EU numbering) with Val,
substitution of Val at position 266 (EU numbering) with Leu,
substitution of Pro at position 271 (EU numbering) with Gly,
substitution of Ile at position 332 (EU numbering) with Phe,
substitution of Ser at position 324 (EU numbering) with Ile,
substitution of Glu at position 333 (EU numbering) with Pro,
substitution of Tyr at position 300 (EU numbering) with Asp,
substitution of Ser at position 337 (EU numbering) with Asp,
substitution of Tyr at position 300 (EU numbering) with Gln,
substitution of Thr at position 335 (EU numbering) with Asp,
substitution of Ser at position 239 (EU numbering) with Asn,
substitution of Lys at position 326 (EU numbering) with Leu,
substitution of Lys at position 326 (EU numbering) with Ile,
substitution of Ser at position 239 (EU numbering) with Glu,
substitution of Lys at position 326 (EU numbering) with Phe,
substitution of Lys at position 326 (EU numbering) with Val,
substitution of Lys at position 326 (EU numbering) with Tyr,
substitution of Ser at position 267 (EU numbering) with Asp,
substitution of Lys at position 326 (EU numbering) with Pro,
substitution of Lys at position 326 (EU numbering) with His,
substitution of Lys at position 334 (EU numbering) with Ala,
substitution of Lys at position 334 (EU numbering) with Trp,
substitution of His at position 268 (EU numbering) with Gln,
substitution of Lys at position 326 (EU numbering) with Gln,
substitution of Lys at position 326 (EU numbering) with Glu,
substitution of Lys at position 326 (EU numbering) with Met,
substitution of Val at position 266 (EU numbering) with Ile,
substitution of Lys at position 334 (EU numbering) with Glu,
substitution of Tyr at position 300 (EU numbering) with Glu,
substitution of Lys at position 334 (EU numbering) with Met,
substitution of Lys at position 334 (EU numbering) with Val,
substitution of Lys at position 334 (EU numbering) with Thr,
substitution of Lys at position 334 (EU numbering) with Ser,
substitution of Lys at position 334 (EU numbering) with His,
substitution of Lys at position 334 (EU numbering) with Phe,
substitution of Lys at position 334 (EU numbering) with Gln,
substitution of Lys at position 334 (EU numbering) with Pro,
substitution of Lys at position 334 (EU numbering) with Tyr,
substitution of Lys at position 334 (EU numbering) with Ile,
substitution of Gln at position 295 (EU numbering) with Leu,
substitution of Lys at position 334 (EU numbering) with Leu,
substitution of Lys at position 334 (EU numbering) with Asn,
substitution of His at position 268 (EU numbering) with Ala,
substitution of Ser at position 239 (EU numbering) with Asp, and
substitution of Ser at position 267 (EU numbering) with Ala.

Furthermore, preferred alterations among these alterations are those that reduce the binding activity towards FcγRIIa (type R) without reducing the binding activity towards FcγRIIb. Preferred examples of such alterations include the following amino acid substitutions:

substitution of Gly at position 237 (EU numbering) with Trp,
substitution of Leu at position 328 (EU numbering) with Asp,
substitution of Gly at position 236 (EU numbering) with Asp,
substitution of Ala at position 327 (EU numbering) with Asn,
substitution of Ala at position 327 (EU numbering) with Gly,
substitution of Ser at position 239 (EU numbering) with Leu,
substitution of Pro at position 331 (EU numbering) with Trp,
substitution of Pro at position 331 (EU numbering) with Tyr,
substitution of Pro at position 331 (EU numbering) with Phe,
substitution of Pro at position 271 (EU numbering) with Leu,
substitution of Leu at position 328 (EU numbering) with Gln,
substitution of Tyr at position 300 (EU numbering) with Asp, and
substitution of Ser at position 239 (EU numbering) with Asn.

Furthermore, it is also possible to add alterations enhancing the binding activity towards FcγRIIb by adding other alterations of the Fc region to human IgG containing substitution of Pro at position 238 (EU numbering) with Asp and/or substitution of Leu at position 328 (EU numbering) with Glu. Preferred alterations among such alterations are those that enhance only the binding activity towards FcγRIIb without enhancing the binding activity towards FcγRI, FcγRIIa (type H), FcγRIIa (type R), or FcγRIIIa. Preferred examples of such alterations include the following amino acid substitutions:

substitution of Gly at position 237 (EU numbering) with Trp,
substitution of Gly at position 237 (EU numbering) with Phe,
substitution of Pro at position 238 (EU numbering) with Phe,
substitution of Asn at position 325 (EU numbering) with Met,
substitution of Ser at position 267 (EU numbering) with Ile,
substitution of Leu at position 328 (EU numbering) with Asp,
substitution of Ser at position 267 (EU numbering) with Val,
substitution of Leu at position 328 (EU numbering) with Trp,
substitution of Ser at position 267 (EU numbering) with Gln,
substitution of Ser at position 267 (EU numbering) with Met,
substitution of Gly at position 236 (EU numbering) with Asp,
substitution of Ala at position 327 (EU numbering) with Asn,
substitution of Asn at position 325 (EU numbering) with Ser,
substitution of Leu at position 235 (EU numbering) with Tyr,
substitution of Val at position 266 (EU numbering) with Met,
substitution of Leu at position 328 (EU numbering) with Tyr,
substitution of Leu at position 235 (EU numbering) with Trp,
substitution of Leu at position 235 (EU numbering) with Phe,
substitution of Ser at position 239 (EU numbering) with Gly,
substitution of Ala at position 327 (EU numbering) with Glu,
substitution of Ala at position 327 (EU numbering) with Gly,
substitution of Pro at position 238 (EU numbering) with Leu,
substitution of Ser at position 239 (EU numbering) with Leu,
substitution of Leu at position 328 (EU numbering) with Thr,
substitution of Leu at position 328 (EU numbering) with Ser,
substitution of Leu at position 328 (EU numbering) with Met,
substitution of Pro at position 331 (EU numbering) with Trp,
substitution of Pro at position 331 (EU numbering) with Tyr,
substitution of Pro at position 331 (EU numbering) with Phe,
substitution of Ala at position 327 (EU numbering) with Asp,
substitution of Leu at position 328 (EU numbering) with Phe,
substitution of Pro at position 271 (EU numbering) with Leu,
substitution of Ser at position 267 (EU numbering) with Glu,
substitution of Leu at position 328 (EU numbering) with Ala,
substitution of Leu at position 328 (EU numbering) with Ile,
substitution of Leu at position 328 (EU numbering) with Gln,
substitution of Leu at position 328 (EU numbering) with Val,
substitution of Lys at position 326 (EU numbering) with Trp,
substitution of Lys at position 334 (EU numbering) with Arg,
substitution of His at position 268 (EU numbering) with Gly,
substitution of His at position 268 (EU numbering) with Asn,
substitution of Ser at position 324 (EU numbering) with Val,
substitution of Val at position 266 (EU numbering) with Leu,
substitution of Pro at position 271 (EU numbering) with Gly,
substitution of Ile at position 332 (EU numbering) with Phe,
substitution of Ser at position 324 (EU numbering) with Ile,
substitution of Glu at position 333 (EU numbering) with Pro,
substitution of Tyr at position 300 (EU numbering) with Asp,
substitution of Ser at position 337 (EU numbering) with Asp,
substitution of Tyr at position 300 (EU numbering) with Gln,
substitution of Thr at position 335 (EU numbering) with Asp,
substitution of Ser at position 239 (EU numbering) with Asn,
substitution of Lys at position 326 (EU numbering) with Leu,
substitution of Lys at position 326 (EU numbering) with Ile,
substitution of Ser at position 239 (EU numbering) with Glu,
substitution of Lys at position 326 (EU numbering) with Phe,
substitution of Lys at position 326 (EU numbering) with Val,
substitution of Lys at position 326 (EU numbering) with Tyr,
substitution of Ser at position 267 (EU numbering) with Asp,
substitution of Lys at position 326 (EU numbering) with Pro,
substitution of Lys at position 326 (EU numbering) with His,
substitution of Lys at position 334 (EU numbering) with Ala,
substitution of Lys at position 334 (EU numbering) with Trp,
substitution of His at position 268 (EU numbering) with Gln,
substitution of Lys at position 326 (EU numbering) with Gln, substitution of Lys at position 326 (EU numbering) with Glu,
substitution of Lys at position 326 (EU numbering) with Met,
substitution of Val at position 266 (EU numbering) with Ile,
substitution of Lys at position 334 (EU numbering) with Glu,
substitution of Tyr at position 300 (EU numbering) with Glu,
substitution of Lys at position 334 (EU numbering) with Met,
substitution of Lys at position 334 (EU numbering) with Val,
substitution of Lys at position 334 (EU numbering) with Thr,
substitution of Lys at position 334 (EU numbering) with Ser,
substitution of Lys at position 334 (EU numbering) with His,
substitution of Lys at position 334 (EU numbering) with Phe,
substitution of Lys at position 334 (EU numbering) with Gln,
substitution of Lys at position 334 (EU numbering) with Pro,
substitution of Lys at position 334 (EU numbering) with Tyr,
substitution of Lys at position 334 (EU numbering) with Ile,
substitution of Gln at position 295 (EU numbering) with Leu,
substitution of Lys at position 334 (EU numbering) with Leu,
substitution of Lys at position 334 (EU numbering) with Asn,
substitution of His at position 268 (EU numbering) with Ala,
substitution of Ser at position 239 (EU numbering) with Asp, and
substitution of Ser at position 267 (EU numbering) with Ala.

Furthermore, preferred alterations among these alterations are those that reduce the binding activity towards FcγRIIa (type R) without reducing the binding activity towards FcγRIIb. Preferred examples of such alterations include the following amino acid substitutions:

substitution of Gly at position 237 (EU numbering) with Trp,
substitution of Leu at position 328 (EU numbering) with Asp,
substitution of Gly at position 236 (EU numbering) with Asp,
substitution of Ala at position 327 (EU numbering) with Asn,
substitution of Ala at position 327 (EU numbering) with Gly,
substitution of Ser at position 239 (EU numbering) with Leu,
substitution of Pro at position 331 (EU numbering) with Trp,
substitution of Pro at position 331 (EU numbering) with Tyr,
substitution of Pro at position 331 (EU numbering) with Phe,
substitution of Pro at position 271 (EU numbering) with Leu,
substitution of Leu at position 328 (EU numbering) with Gln,
substitution of Tyr at position 300 (EU numbering) with Asp, and
substitution of Ser at position 239 (EU numbering) with Asn.

Furthermore, for example, amino acid substitutions that improve FcRn-binding activity (J. Immunol. 2006 Jan. 1; 176(1): 346-56; J Biol Chem. 2006 Aug. 18; 281(33): 23514-24; Int. Immunol. 2006 December; 18(12): 1759-69; Nat Biotechnol. 2010 February; 28(2): 157-9; WO 2006/019447; WO 2006/053301; and WO 2009/086320), and amino acid substitutions for improving antibody heterogeneity or stability (WO 2009/041613) may be introduced into the Fc region of an antibody.

In addition to the amino acid modifications of the present invention, the following modifications can be added as necessary.

In order to regulate the plasma retention property of antibodies, it is possible to combine the amino acid modifications of the present invention with amino acid modifications for altering the antibody isoelectric point value (pI value). Modifications of the constant regions include, for example, amino acid modifications at positions 250 and 428 (EU numbering) and such described in known publications (for example, J. Immunol. 2006, 176 (1):346-356; and Nat. Biotechnol. 1997 15 (7):637-640). Modifications of the variable regions include the amino acid modifications described in WO2007/114319 and WO2009/041643. Amino acids to be modified are preferably exposed on the surface of a polypeptide having an antigen-binding activity. When a polypeptide of the present invention has a heavy chain constant region, the modifications include, for example, amino acid substitution at position 196 (EU numbering) in the amino acid sequence of the heavy chain constant region. When the heavy chain constant region is that of IgG4, the plasma retention can be enhanced, for example, by substituting lysine at position 196 with glutamine and thereby reducing the pI value. Furthermore, the plasma retention can be regulated by altering the FcRn-binding ability. Amino acid modifications that alter the FcRn-binding ability include, for example, the amino acid substitutions in the antibody heavy chain constant region described in known publications (The Journal of Biological Chemistry vol. 276, No. 9 6591-6604, 2001; and Molecular Cell, Vol. 7, 867-877, 2001).

Modifications for Improving the Stability Under Acidic Conditions

When a polypeptide of the present invention has a heavy chain constant region of IgG4, the stable four-chain structure (H2L2 structure) is preferably maintained by suppressing the dissociation of IgG4 into half-molecules under acidic conditions. Thus, arginine at amino acid position 409 (EU numbering), which plays an important role in the maintenance of the four-chain structure (Immunology 2002, 105, 9-19), is preferably substituted with lysine, the residue of the IgG1 type, which maintains the stable four-chain structure even under acidic conditions. Such modifications can be used in combination with the amino acid modifications of the present invention.

Modifications for Reducing Heterogeneity

The amino acid modifications of the present invention may be combined with the methods described in WO2009/

041613. Specifically, for example, when a polypeptide of the present invention has a heavy chain constant region of IgG1, it is possible to combine the modification for deleting the C-terminal two amino acids of the IgG1 heavy chain constant region, that is, glycine and lysine at positions 446 and 447 (EU numbering), with the amino acid modifications described in the present Examples so that the heterogeneity can be reduced.

Modifications for Suppressing Deamidation Reaction

The amino acid modifications of the present invention may be combined with amino acid modifications for suppressing deamidation reaction. It has been reported that deamidation reaction tends to occur particularly at a site where asparagine (N) and glycine (G) are adjacent to each other (-NG-) (Geiger et al., J. Bio. Chem. 1987; 262:785-794). When a polypeptide of the present invention has a site where asparagine and glycine are adjacent to each other, deamidation reaction can be suppressed by modifying this amino acid sequence. Specifically, for example, either or both of asparagine and glycine are substituted with other amino acids. More specifically, for example, asparagine is substituted with aspartic acid.

Preferred examples of polypeptides of the present invention include IgG antibodies. When an IgG antibody is used as the antibody, the type of constant region is not limited, and an IgG isotypes (subclasses) such as IgG1, IgG2, IgG3, and IgG4 can be used. IgG antibodies of the present invention are preferably human IgG, and more preferably human IgG1 or human IgG4. The amino acid sequences of the heavy-chain Fc regions of human IgG1 and human IgG4 are known. A plurality of allotype sequences due to genetic polymorphisms have been described in Sequences of Proteins of Immunological Interest, NIH Publication No. 91-3242 for the human IgG1 Fc region, and any of the sequences may be used in the present invention.

Substitutionc

For example, for the purpose of modifying (a)-(c) listed below, amino acid residues can be substituted with other amino acid residues:
(a) polypeptide backbone structure in the sheet-structure or helical-structure region;
(b) electric charge or hydrophobicity at the target site; or
(c) size of the side chain.

Amino acid residues are classified into the following groups based on their general side chain properties:
(1) hydrophobic: norleucine, met, ala, val, leu, and ile;
(2) neutral hydrophilic: cys, ser, thr, asn, and gln;
(3) acidic: asp and glu;
(4) basic: his, lys, and arg;
(5) residues that affect the chain orientation: gly and pro; and
(6) aromatic: trp, tyr, and phe.

Substitution between amino acid residues within each of these amino acid groups is referred to as conservative substitution, and amino acid residue substitution between different groups is referred to as non-conservative substitution. Substitutions in the present invention may be conservative substitutions or non-conservative substitutions, or a combination of conservative substitutions and non-conservative substitutions.

Amino acid sequence alterations are produced by various methods known to those skilled in the art. Such methods include the site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152: 271-275; Zoller, M J, and Smith, M. (1983) Oligonucleotide-directed mutagenesis of DNA fragments cloned into M13 vectors. Methods Enzymol. 100: 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12: 9441-9456; Kramer W, and Fritz H J (1987) Oligonucleotide-directed construction of mutations via gapped duplex DNA Methods. Enzymol. 154, 350-367; and Kunkel, T A (1985) Rapid and efficient site-specific mutagenesis without phenotypic selection. Proc Natl Acad Sci USA. 82: 488-492), the PCR mutation method, and the cassette mutation method, but are not limited thereto.

Amino acid modification of the present invention includes post-translational modification. A specific post-translational modification may be addition or deletion of a sugar chain. For example, in the IgG1 Fc region consisting of the amino acid sequence of SEQ ID NO: 11, the amino acid residue at position 297 (EU numbering) may be sugar chain-modified. The sugar-chain structure for the modification is not limited. Generally, antibodies expressed in eukaryotic cells comprise glycosylation in the Fc region. Therefore, antibodies expressed in cells such as those below are normally modified by some type of sugar chain:
  antibody-producing cells of mammals
  eukaryotic cells transformed with an expression vector comprising a DNA encoding an antibody Eukaryotic cells shown here include yeast and animal cells. For example, CHO cells and HEK293H cells are representative animal cells used in transformation with an expression vector comprising an antibody-encoding DNA. On the other hand, the Fc regions of the present invention include those without glycosylation at this site. Antibodies whose Fc region is not glycosylated can be obtained by expressing an antibody-encoding gene in prokaryotic cells such as *Escherichia coli*.

Specifically, for example, sialic acid may be added to the sugar chain of an Fc region (MAbs. 2010 September-October; 2(5): 519-27).

Antibody

Furthermore, the present invention provides antibodies with an Fc region in which any of the above-mentioned amino acid sequences is altered.

The term "antibody/antibodies" in the present invention is used in the broadest sense, and as long as the desired biological activity is shown, it encompasses any antibodies such as monoclonal antibodies (including full-length monoclonal antibodies), polyclonal antibodies, antibody variants, antibody fragments, multispecific antibodies (for example, bispecific antibodies (which may be referred to as diabodies)), chimeric antibodies, and humanized antibodies.

The antibodies of the present invention are not limited in terms of the antigen type and origin, and may be any types of antibodies. The origin of the antibodies is not particularly limited, but examples include human antibodies, mouse antibodies, rat antibodies, and rabbit antibodies.

Methods for producing the antibodies are well known to those skilled in the art, and for example, monoclonal antibodies may be produced by the hybridoma method (Kohler and Milstein, Nature 256: 495 (1975)), or the recombination method (U.S. Pat. No. 4,816,567). Alternatively, they may be isolated from a phage antibody library (Clackson et al., Nature 352: 624-628 (1991); Marks et al., J. Mol. Biol. 222: 581-597 (1991)). In the present invention, monoclonal antibodies include humanized antibodies and chimeric antibodies.

In addition to the above methods, B cell cloning (use for identification and cloning of the coding sequence of each antibody, isolation thereof, and construction of expression vectors for producing each antibody (particularly IgG1, IgG2, IgG3, or IgG4) etc.) as described in Bernasconi et al. (Science (2002) 298, 2199-2202) or WO2008/081008 is appropriately used as a method for obtaining antibody genes.

Moreover, the antibodies of the present invention may have an altered sugar chain. Examples of antibodies whose sugar chain has been altered include, for example, antibodies with modified glycosylation (WO99/54342 and such), antibodies deficient in fucose attached to a sugar chain (WO00/61739, WO02/31140, WO2006/067847, WO2006/067913, and such), and antibodies having a sugar chain with bisecting GlcNAc (WO02/79255 and such).

A humanized antibody is also called a reshaped human antibody. Specifically, humanized antibodies prepared by grafting the CDRs of a non-human animal antibody such as a mouse antibody to a human antibody and such are known. Common genetic engineering techniques for obtaining humanized antibodies are also known. Specifically, for example, overlap extension PCR is known as a method for grafting mouse antibody CDRs to human FRs. Furthermore, it is also possible to design an amino acid sequence in which mouse CDRs have been grafted on human FRs, and then synthesize a gene of this amino acid sequence. Gene synthesis services are provided by, for example, Life Technologies, GenScript, and other companies.

A vector for expressing a humanized antibody can be produced by inserting a DNA encoding an antibody variable region in which three CDRs and four FRs are ligated and a DNA encoding a human antibody Fc region into an expression vector so that these DNAs are fused in frame. After this integration vector is transfected into a host to establish recombinant cells, these cells are cultured, and the DNA encoding the humanized antibody is expressed to produce the humanized antibody in the culture of the cells (see, European Patent Publication No. EP 239,400, and International Patent Publication No. WO 1996/002576).

As necessary, an amino acid residue in an FR may be substituted so that the CDRs of a reshaped human antibody form an appropriate antigen-binding site. For example, a mutation can be introduced into the amino acid sequence of an FR by applying the PCR method used for grafting mouse CDRs to human FRs.

A desired human antibody can be obtained by DNA immunization using a transgenic animal having the complete repertoire of human antibody genes (see International Publication Nos. WO 1993/012227, WO 1992/003918, WO 1994/002602, WO 1994/025585, WO 1996/034096, and WO 1996/033735) as an animal for immunization.

Furthermore, technologies for obtaining a human antibody by panning using a human antibody library are known. For example, a human antibody V region is expressed on the surface of a phage as a single-chain antibody (scFv) by the phage display method. The scFv-expressing phage that binds to the antigen can be selected. The DNA sequence that encodes the V region of the antigen-bound human antibody can be determined by analyzing the genes of the selected phage. After determining the DNA sequence of the scFv that binds to the antigen, an expression vector can be prepared by fusing the V-region sequence in-frame with the sequence of a desired human antibody C region, and then inserting this into a suitable expression vector. The expression vector is introduced into suitable expression cells such as those described above, and the human antibody can be obtained by expressing the human antibody-encoding gene. These methods are already known (see, International Publication Nos. WO 1992/001047, WO 1992/020791, WO 1993/006213, WO 1993/011236, WO 1993/019172, WO 1995/001438, and WO 1995/15388).

Herein, there is no particular limitation on the antigen, and it may be any antigens. Examples of such antigens preferably include ligands (cytokines, chemokines, and such), receptors, cancer antigens, MHC antigens, differentiation antigens, immunoglobulins, and immune complexes partly containing immunoglobulins.

Examples of cytokines include interleukins 1 to 18, colony stimulating factors (G-CSF, M-CSF, GM-CSF, etc.), interferons (IFN-$\alpha$, IFN-$\beta$, IFN-$\gamma$, etc.), growth factors (EGF, FGF, IGF, NGF, PDGF, TGF, HGF, etc.), tumor necrosis factors (TNF-$\alpha$ and TNF-$\beta$), lymphotoxin, erythropoietin, leptin, SCF, TPO, MCAF, and BMP.

Examples of chemokines include CC chemokines such as CCL1 to CCL28, CXC chemokines such as CXCL1 to CXCL17, C chemokines such as XCL1 and XCL2, and CX3C chemokines such as CX3CL1.

Examples of receptors include receptors belonging to receptor families such as the hematopoietic growth factor receptor family, cytokine receptor family, tyrosine kinase-type receptor family, serine/threonine kinase-type receptor family, TNF receptor family, G protein-coupled receptor family, GPI anchor-type receptor family, tyrosine phosphatase-type receptor family, adhesion factor family, and hormone receptor family. The receptors belonging to these receptor families and their characteristics have been described in many documents such as Cooke B A., King R J B., van der Molen H J. ed. New Comprehesive Biochemistry Vol. 18B "Hormones and their Actions Part II" pp. 1-46 (1988) Elsevier Science Publishers BV; Patthy (Cell (1990) 61 (1): 13-14); Ullrich et al. (Cell (1990) 61 (2): 203-212); Massagué (Cell (1992) 69 (6): 1067-1070); Miyajima et al. (Annu. Rev. Immunol. (1992) 10: 295-331); Taga et al. (FASEB J. (1992) 6, 3387-3396); Fantl et al. (Annu. Rev. Biochem. (1993), 62: 453-481); Smith et al. (Cell (1994) 76 (6): 959-962); and Flower D R. (Biochim. Biophys. Acta (1999) 1422 (3): 207-234).

Examples of specific receptors belonging to the above-mentioned receptor families preferably include human or mouse erythropoietin (EPO) receptors (Blood (1990) 76 (1): 31-35; and Cell (1989) 57 (2): 277-285), human or mouse granulocyte-colony stimulating factor (G-CSF) receptors (Proc. Natl. Acad. Sci. USA. (1990) 87 (22): 8702-8706, mG-CSFR; Cell (1990) 61 (2): 341-350), human or mouse thrombopoietin (TPO) receptors (Proc Natl Acad Sci USA. (1992) 89 (12): 5640-5644; EMBO J. (1993) 12(7): 2645-53), human or mouse insulin receptors (Nature (1985) 313 (6005): 756-761), human or mouse Flt-3 ligand receptors (Proc. Natl. Acad. Sci. USA. (1994) 91 (2): 459-463), human or mouse platelet-derived growth factor (PDGF) receptors (Proc. Natl. Acad. Sci. USA. (1988) 85 (10): 3435-3439), human or mouse interferon (IFN)-$\alpha$ and $\beta$ receptors (Cell (1990) 60 (2): 225-234; and Cell (1994) 77 (3): 391-400), human or mouse leptin receptors, human or mouse growth hormone (GH) receptors, human or mouse interleukin (IL)-10 receptors, human or mouse insulin-like growth factor (IGF)-I receptors, human or mouse leukemia inhibitory factor (LIF) receptors, and human or mouse ciliary neurotrophic factor (CNTF) receptors.

Cancer antigens are antigens that are expressed as cells become malignant, and they are also called tumor-specific antigens. Abnormal sugar chains that appear on cell surfaces or protein molecules when cells become cancerous are also cancer antigens, and they are also called sugar-chain cancer antigens. Examples of cancer antigens preferably include GPC3 which is a receptor belonging to the GPI anchor-type receptor family mentioned above, and is also expressed in several cancers including liver cancer (Int J Cancer. (2003) 103 (4): 455-65), as well as EpCAM which is expressed in several cancers including lung cancer (Proc Natl Acad Sci USA. (1989) 86 (1): 27-31), CA19-9, CA15-3, and sialyl SSEA-1 (SLX). MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens may include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Immunoglobulins include IgA, IgM, IgD, IgG and IgE. Immunocomplexes at least contain any component of an immunoglobulin.

Variable regions that constitute the antibodies of the present invention may be variable regions that recognize any antigen. One or more amino acid residue alterations are allowed in the amino acid sequences constituting the antibody variable regions as long as their antigen-binding activities are maintained. When altering a variable region amino acid sequence, there is no particularly limitation on the site of alteration and number of amino acids altered. For example, amino acids present in CDR and/or FR can be altered appropriately. When altering amino acids in a variable region, the binding activity is preferably maintained without particular limitation; and for example, as compared to before alteration, the binding activity is 50% or more, preferably 80% or more, and more preferably 100% or more. Furthermore, the binding activity may be increased by amino acid alterations. For example, the binding activity may be 2-, 5-, 10-times higher or such than that before alteration.

When the antigen is a soluble antigen, KD (dissociation constant) can be used as a value representing the antigen-binding activity of an antibody of the present invention. When the antigen is a membrane antigen, apparent KD (apparent dissociation constant) can be used. KD (dissociation constant) and apparent KD (apparent dissociation constant) can be determined by methods known to those skilled in the art, such as Biacore (GE Healthcare), Scatchard plot, and flow cytometer.

As another index for comparing the antigen-binding activity of the antibodies of the present invention, for example, $k_d$ (dissociation rate constant) can be used when the antigen is a soluble antigen, whilst apparent $k_d$ (apparent dissociation rate constant) can be used when the antigen is a membrane antigen. $k_d$ (dissociation rate constant) and apparent $k_d$ (apparent dissociation rate constant) can be determined by methods known to those skilled in the art, such as Biacore (GE Healthcare) and flow cytometer.

In the antibodies of the present invention, alteration of amino acid sequence may be at least one of amino acid residue substitution, addition, deletion, and modification. There is no particular limitation on positions to be altered and the number of amino acids to be altered. Generally, 50 amino acids or less, preferably 30 amino acids or less, more preferably 10 amino acids or less (for example, 5 amino acids or less, or 3 amino acids or less) may be altered. Alternatively, for example, alteration of 20% or less amino acid residues, or specifically 10% or less amino acid residues (for example, 10%, 9%, 8%, 7%, 6%, 5%, 4%, 3%, 2%, or 1% or less) in the whole amino acid sequence is acceptable. In other words, antibodies containing an amino acid sequence sharing a homology (identity) of preferably 80% or higher, more preferably 90% or higher (for example, 90%, 91%, 92%, 93%, 94%, 95%, 96%, 97%, 98%, or 99% or higher) with the original amino acid sequence are also included in the antibodies of the present invention.

For example, the modification of the N-terminal glutamine of a variable region into pyroglutamic acid by pyroglutamylation is a modification well known to those skilled in the art. Thus, when the heavy-chain N terminus is glutamine, the antibodies of the present invention also include the variable regions in which the glutamine is modified to pyroglutamic acid.

Antibody variable regions of the present invention may have any sequences, and they may be antibody variable regions of any origin, such as mouse antibodies, rat antibodies, rabbit antibodies, goat antibodies, camel antibodies, humanized antibodies produced by humanizing these non-human antibodies, and human antibodies. "Humanized antibodies", also referred to as "reshaped human antibodies", are antibodies in which the complementarity determining regions (CDRs) of an antibody derived from a non-human mammal, for example, a mouse antibody, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). Their common genetic recombination techniques are also known (see, European Patent Application Publication No. EP 125023 and WO 96/02576). Furthermore, these antibodies may have various amino acid substitutions introduced into their variable regions to improve their antigen binding, pharmacokinetics, stability, and antigenicity. Variable regions of the antibodies of the present invention may be able to bind antigens repeatedly due to their pH dependability in antigen binding (WO 2009/125825).

There are κ chain and λ chain types in antibody light-chain constant regions, but any light chain constant regions may be used. Furthermore, light-chain constant regions of the present invention may be light-chain constant regions with amino acid alterations such as substitutions, deletions, additions, and/or insertions.

For the heavy chain Fc regions of an antibody of the present invention, for example, heavy chain Fc regions of human IgG antibodies may be used. Preferred heavy chain Fc regions are those of human IgG1 antibodies and human IgG4 antibodies.

Furthermore, polypeptides of the present invention may be made into Fc fusion protein molecules by linking to other proteins, physiologically active peptides, and such.

Examples of the other proteins and biologically active peptides include receptors, adhesion molecules, ligands, and enzymes, but are not limited thereto.

Preferred examples of Fc fusion protein molecules of the present invention include proteins with Fc region fused to a receptor protein that binds to a target, and such examples include TNFR-Fc fusion protein, IL1R-Fc fusion protein, VEGFR-Fc fusion protein, and CTLA4-Fc fusion protein (Nat Med. 2003 January; 9(1): 47-52; BioDrugs. 2006; 20(3): 151-60). Furthermore, a protein to be fused to a polypeptide of the present invention may be any molecule as long as it binds to a target molecule, and examples include scFv molecules (WO 2005/037989), single-domain antibody molecules (WO 2004/058821; WO 2003/002609), antibody-like molecules (Current Opinion in Biotechnology 2006, 17: 653-658; Current Opinion in Biotechnology 2007, 18: 1-10; Current Opinion in Structural Biology 1997, 7: 463-469; and Protein Science 2006, 15: 14-27) such as DARPins (WO 2002/020565), Affibody (WO 1995/001937), Avimer (WO 2004/044011; WO 2005/040229), and Adnectin (WO 2002/032925). Furthermore, antibodies and Fc fusion protein molecules may be multispecific antibodies that bind to multiple types of target molecules or epitopes.

Furthermore, the antibodies of the present invention include antibody modification products. Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in different molecules.

The polypeptides of the present invention can be prepared by the methods known to those skilled in the art. For example, the antibodies can be prepared by the methods described below, but the methods are not limited thereto A DNA encoding an antibody heavy chain in which one or more amino acid residues in the Fc region have been substituted with other amino acids of interest and DNA encoding an antibody light chain, are expressed. A DNA encoding a heavy chain in which one or more amino acid residues in the Fc region are substituted with other amino acids of interest can be prepared, for example, by obtaining a DNA encoding the Fc region of a natural heavy chain, and introducing an appropriate substitution so that a codon encoding a particular amino acid in the Fc region encodes another amino acid of interest.

Alternatively, a DNA encoding a heavy chain in which one or more amino acid residues in the Fc region are substituted with other amino acids of interest can also be prepared by designing and then chemically synthesizing a DNA encoding a protein in which one or more amino acid residues in the Fc region of the natural heavy chain are substituted with other amino acids of interest. The position and type of amino acid substitution are not particularly limited. Furthermore, alteration is not limited to substitution, and alteration may be any of deletion, addition, or insertion, or combination thereof.

Alternatively, a DNA encoding a heavy chain in which one or more amino acid residues in the Fc region are substituted with other amino acids of interest can be prepared as a combination of partial DNAs. Such combinations of partial DNAs include, for example, the combination of a DNA encoding a variable region and a DNA encoding an Fc region, and the combination of a DNA encoding an Fab region and a DNA encoding an Fc region, but are not limited thereto. Furthermore, a DNA encoding a light chain can similarly be prepared as a combination of partial DNAs.

Methods for expressing the above-described DNAs include the methods described below. For example, a heavy chain expression vector is constructed by inserting a DNA encoding a heavy chain variable region into an expression vector along with a DNA encoding a heavy chain Fc region. Likewise, a light chain expression vector is constructed by inserting a DNA encoding a light chain variable region into an expression vector along with a DNA encoding a light chain Fc region. Alternatively, these heavy and light chain genes may be inserted into a single vector.

When inserting a DNA encoding the antibody of interest into an expression vector, the DNA is inserted so that the antibody is expressed under the control of an expression-regulating region such as an enhancer or promoter. Next, host cells are transformed with this expression vector to express the antibody. In such cases, an appropriate combination of host and expression vector may be used.

Examples of the vectors include M13 vectors, pUC vectors, pBR322, pBluescript, and pCR-Script. Alternatively, when aiming to subclone and excise cDNA, in addition to the vectors described above, pGEM-T, pDIRECT, pT7, and such can be used.

Expression vectors are particularly useful when using vectors for producing the polypeptides of the present invention. For example, when a host cell is *E. coli* such as JM109, DH5α, HB101, and XL1-Blue, the expression vectors must carry a promoter that allows efficient expression in *E. coli*, for example, lacZ promoter (Ward et al., Nature (1989) 341: 544-546; FASEB J. (1992) 6: 2422-2427; its entirety are incorporated herein by reference), araB promoter (Better et al., Science (1988) 240: 1041-1043; its entirety are incorporated herein by reference), T7 promoter, or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for polypeptide secretion. As a signal sequence for polypeptide secretion, a pelB signal sequence (Lei, S. P. et al J. Bacteriol. (1987) 169: 4379; its entirety are incorporated herein by reference) may be used when a polypeptide is secreted into the *E. coli* periplasm. The vector can be introduced into host cells by lipofectin method, calcium phosphate method, and DEAE-Dextran method, for example.

In addition to *E. coli* expression vectors, the vectors for producing the polypeptides of the present invention include mammalian expression vectors (for example, pcDNA3 (Invitrogen), pEGF-BOS (Nucleic Acids. Res. 1990, 18(17): p5322; its entirety are incorporated herein by reference), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277: 108; its entirety are incorporated herein by reference), MMTV-LTR promoter, EF1α promoter (Mizushima et al., Nucleic Acids Res. (1990) 18: 5322; its entirety are incorporated herein by reference), CAG promoter (Gene. (1990) 18: 5322; its entirety are incorporated herein by reference), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene copy number amplification in cells: CHO cells deficient in a nucleic acid synthesis pathway are introduced with a vector that carries a DHFR gene which compensates for the deficiency (for example, pCHOI), and the vector is amplified using methotrexate (MTX). Alternatively, the following method can be used for transient gene expression: COS cells with a gene expressing SV40 T antigen on their chromosome are transformed with a vector with an SV40 replication origin (pcD and such). Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, E. coli xanthine-guanine phosphoribosyltransferase (Ecogpt) gene, and dihydrofolate reductase (dhfr) gene.

Antibodies can be collected, for example, by culturing transformed cells, and then separating the antibodies from the inside of the transformed cells or from the culture media. Antibodies can be separated and purified using an appropriate combination of methods such as centrifugation, ammonium sulfate fractionation, salting out, ultrafiltration, 1q, FcRn, protein A, protein G column, affinity chromatography, ion exchange chromatography, and gel filtration chromatography.

Furthermore, the present invention provides methods for altering a polypeptide to produce a polypeptide with improved stability as compared to the parent polypeptide. Thus, the present invention relates to methods for improving the stability of a polypeptide having an antibody Fc region as compared to the parent polypeptide by introducing at least one amino acid alteration in a loop region of the Fc region. In the present methods, melting temperature (Tm) is preferably used as an index for evaluating or judging the stability.

In addition, the present invention provides methods for producing a polypeptide with improved stability as compared to a parent polypeptide.

As an embodiment of the production methods of the present invention, for example, a method for producing a polypeptide which has an antibody Fc region, at least one of whose amino acids in a loop region of the Fc region is altered, and which has improved stability as compared to the parent antibody, is provided.

For example, such methods include methods including the following steps:
  (a) adding at least one amino acid alteration to the Fc region of a polypeptide having an antibody Fc region;
  (b) measuring the stability of the polypeptide altered in step (a); and
  (c) selecting a polypeptide with improved stability as compared to the parent polypeptide.

Preferred embodiments include a method for producing a polypeptide which has antibody Fc region, at least one of whose amino acids in a loop region of the Fc region is altered, and which has improved stability as compared to the parent polypeptide, wherein the method includes the following steps:
  (a) altering a nucleic acid encoding the polypeptide so that its stability is improved as compared to the parent peptide;
  (b) introducing the nucleic acid into host cells and culturing them to induce expression; and
  (c) collecting the polypeptide from the host cell culture.

Furthermore, polypeptides (antibodies) and Fc fusion protein molecules produced by this production method are also included in the present invention.

In preferred embodiments of the above-mentioned methods, for example, a nucleic acid encoding a polypeptide having an Fc region of antibody (such as human IgG) such that at least one or more amino acids are altered at amino acid position(s) of the loop region of the Fc region selected from the group consisting of: position 234 (EU numbering), position 235 (EU numbering), position 236 (EU numbering), position 237 (EU numbering), position 238 (EU numbering), position 239 (EU numbering), position 247 (EU numbering), position 250 (EU numbering), position 265 (EU numbering), position 266 (EU numbering), position 267 (EU numbering), position 268 (EU numbering), position 269 (EU numbering), position 270 (EU numbering), position 271 (EU numbering), position 295 (EU numbering), position 296 (EU numbering), position 298 (EU numbering), position 300 (EU numbering), position 307 (EU numbering), position 309 (EU numbering), position 315 (EU numbering), position 324 (EU numbering), position 325 (EU numbering), position 326 (EU numbering), position 327 (EU numbering), position 329 (EU numbering), position 330 (EU numbering), position 333 (EU numbering), position 335 (EU numbering), position 337 (EU numbering), position 360 (EU numbering), position 385 (EU numbering), position 386 (EU numbering), position 387 (EU numbering), position 389 (EU numbering), position 428 (EU numbering), and position 433 (EU numbering).

In the above-mentioned methods or production methods (which may be simply referred to as "methods"), it is preferred to further reduce the binding activity towards FcγR. In order to make modifications to maintain or enhance the binding activity towards FcγR as compared to the parent polypeptide, for example, the steps of altering the amino acid alteration sites of TS1-TS8, TS20-TS27, TS44-TS50, TS52-TS55, and TS57-TS67 as shown in the Examples described below, may be included.

Alternatively, it is preferred to further maintain or enhance the binding activity towards FcγR in the above-mentioned methods. In order to make modifications to reduce the binding activity towards FcγR as compared to the parent polypeptide, for example, the steps of altering the amino acid alteration sites of TS9-19, TS28-43, TS51, and TS56 as shown in the Examples described below, may be included.

The alteration sites of TS1-TS67 are as mentioned above.

In the above-mentioned methods, for example, it is preferred to alter amino acids in a polypeptide that has an Fc region of antibody (such as human IgG).

Furthermore, the present invention provides nucleic acids encoding a polypeptide which has an antibody Fc region, at least one of whose amino acids in a loop region of the Fc region is altered, and which has improved stability as compared to the parent polypeptide. The nucleic acids of the present invention may be in any form such as DNA and RNA.

The present invention also provides vectors carrying the above-described nucleic acids of the present invention. The type of vector can be appropriately selected by those skilled in the art depending on the host cells to be introduced with the vector. The vectors include, for example, those described above.

Furthermore, the present invention relates to host cells transformed with the above-described vectors of the present invention. Appropriate host cells can be selected by those skilled in the art. The host cells include, for example, those described above.

<Pharmaceutical Compositions>

The present invention provides pharmaceutical compositions comprising a polypeptide or Fc fusion protein molecule of the present invention.

The pharmaceutical compositions of the present invention can be formulated, in addition to a polypeptide or Fc-fusion protein molecule of the present invention described above, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies or Fc-fusion protein molecules with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dosage of the pharmaceutical composition containing an antibody or a polynucleotide encoding an antibody can be selected, for example, from the range of 0.0001 to 1,000 mg per kg of body weight. Alternatively, the dosage may be, for example, in the range of 0.001 to 100,000 mg/patient. However, the dosage is not limited to these values. The dosage and method of administration vary depending on the patient's body weight, age, and symptoms, and can be appropriately selected by those skilled in the art.

In the present invention, pharmaceutical compositions containing a polypeptide of the present invention mentioned above are useful as an active ingredient of therapeutic agents or preventive agents for immunological inflammatory diseases, cancer, and such. Without being limited thereto, the term "immunological inflammatory diseases" includes rheumatoid arthritis, autoimmune hepatitis, autoimmune thyroiditis, autoimmune blistering diseases, autoimmune adrenocortical disease, autoimmune hemolytic anemia, autoimmune thrombocytopenic purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial pulmonary fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow's disease, juvenile diabetes, Addison's disease, myasthenia gravis, lens-induced uveitis, systemic lupus erythematosus, allergic rhinitis, allergic dermatitis, ulcerative colitis, hypersensitivity, asthma, muscle degeneration, cachexia, systemic scleroderma, localized scleroderma, Sjogren's syndrome, Behcbet's disease, Reiter's syndrome, type I and type II diabetes, bone resorption disorder, graft-versus-host reaction, ischemia-reperfusion injury, atherosclerosis, brain trauma, multiple sclerosis, cerebral malaria, sepsis, septic shock, toxic shock syndrome, fever, malgias due to staining, aplastic anemia, hemolytic anemia, idiopathic thrombocytopenia, Goodpasture's syndrome, Guillain-Barre syndrome, Hashimoto's thyroiditis, pemphigus, IgA nephropathy, pollinosis, antiphospholipid antibody syndrome, polymyositis, Wegener's granulomatosis, arteritis nodosa, mixed connective tissue disease, and fibromyalgia.

In the present invention, "cancer" means a physiological state in mammals that is typically characterized by uncontrolled cell growth, or refers to such a physiological state. In the present invention, the type of cancer is not particularly limited, but includes the following. Carcinoma (epithelial cancer) includes pancreatic cancer, prostate cancer, breast cancer, skin cancer, gastrointestinal cancer, lung cancer, hepatoma, cervical cancer, endometrial cancer, ovarian cancer, fallopian tube cancer, vaginal cancer, liver cancer, cholangioma, bladder cancer, ureteral cancer, thyroid cancer, adrenal cancer, renal cancer, and other glandular tissue cancers. Sarcoma (non-epithelial cancer) includes liposarcoma, leiomyosarcoma, rhabdomyosarcoma, synovial sarcoma, angiosarcoma, fibrosarcoma, malignant peripheral nerve tumor, gastrointestinal stromal tumor, desmoid tumor, Ewing's sarcoma, osteosarcoma, chondrosarcoma, leukemia, lymphoma, myeloma, and other solid organ tumors such as melanoma and brain tumor.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Herein below, the present invention will be specifically described with reference to the Examples, but it is not to be construed as being limited thereto. In the present Examples, the sites of amino acids modified in the Fc region were numbered according to the EU numbering system (see, Sequences of proteins of immunological interest, NIH Publication No. 91-3242).

[Example 1] Improvement of Thermal Stability Through Modification of the CH2 Domain Loop Region Generally, β sheet structure is known to readily undergo structural changes and reduction in thermal stability by amino acid mutations (Biochemistry 1994; 33:5510-5517; and Nature 1994; 367:660-663). Therefore, in the present invention, the loop regions of the Fc region were selected for mutagenesis to improve the thermal stability.

Figure 4:
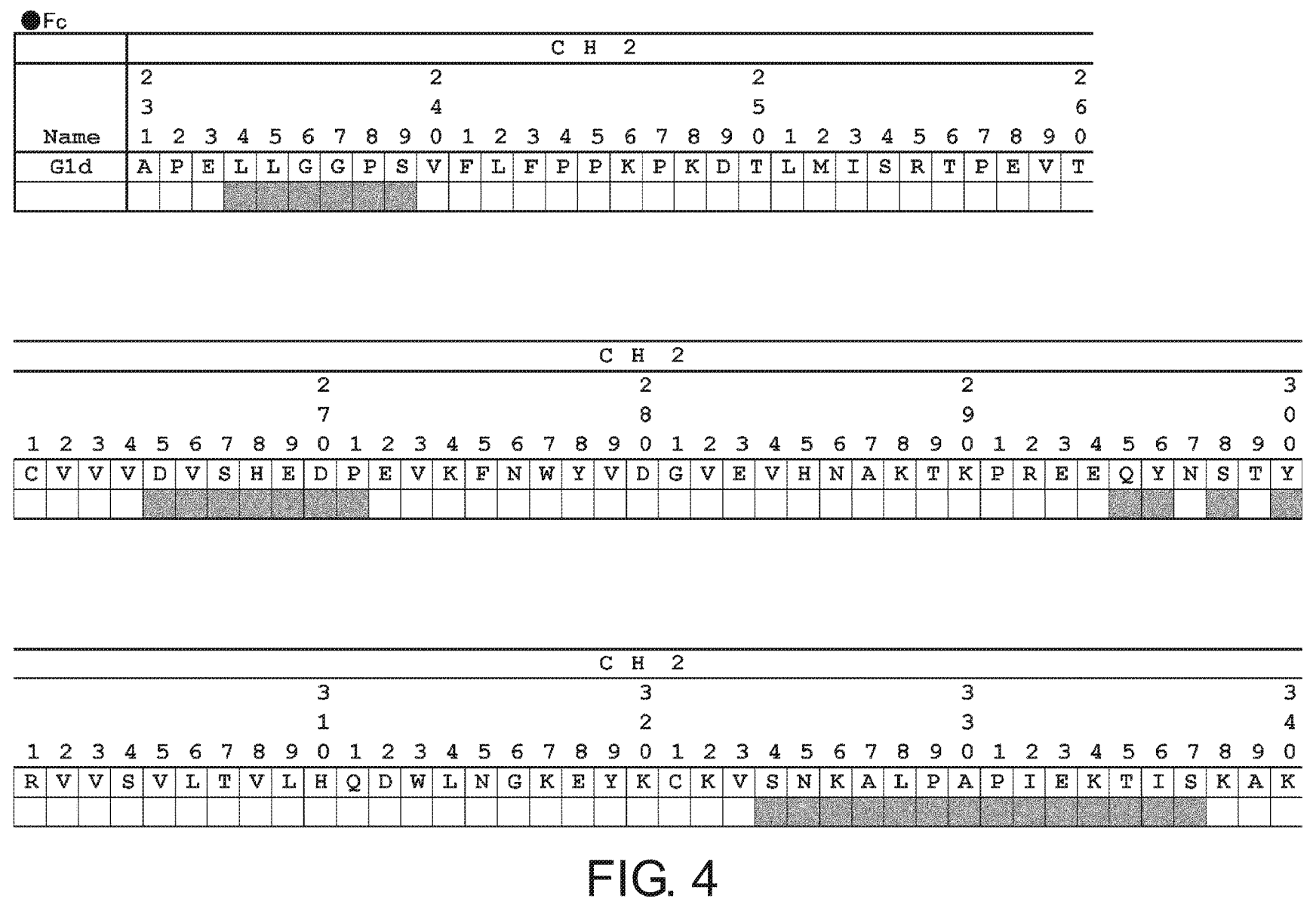

The amino acids of L234-S239, D265-P271, Q295, Y296, S298, Y300, S324-S337 in the loop region of the CH2 domain of Fc region B3 (SEQ ID NO: 16) were substituted with each of 18 amino acids not including the original amino acid and cysteine, to produce Fc mutants (FIG. 4). These are called Fc variants. Anti-GPC3 antibodies were produced using these Fc variants. Antibodies composed of an H chain which consists of variable region GpH7 (SEQ ID NO: 17) and an Fc variant as the Fc region and an L chain which consists of variable region GpL16 (SEQ ID NO: 18) and constant region k0 (SEQ ID NO: 19) (hereinafter denoted as GpH7-Fc variant/GpL16-k0) were produced according to the method of Reference Example 1.

Figure 1:
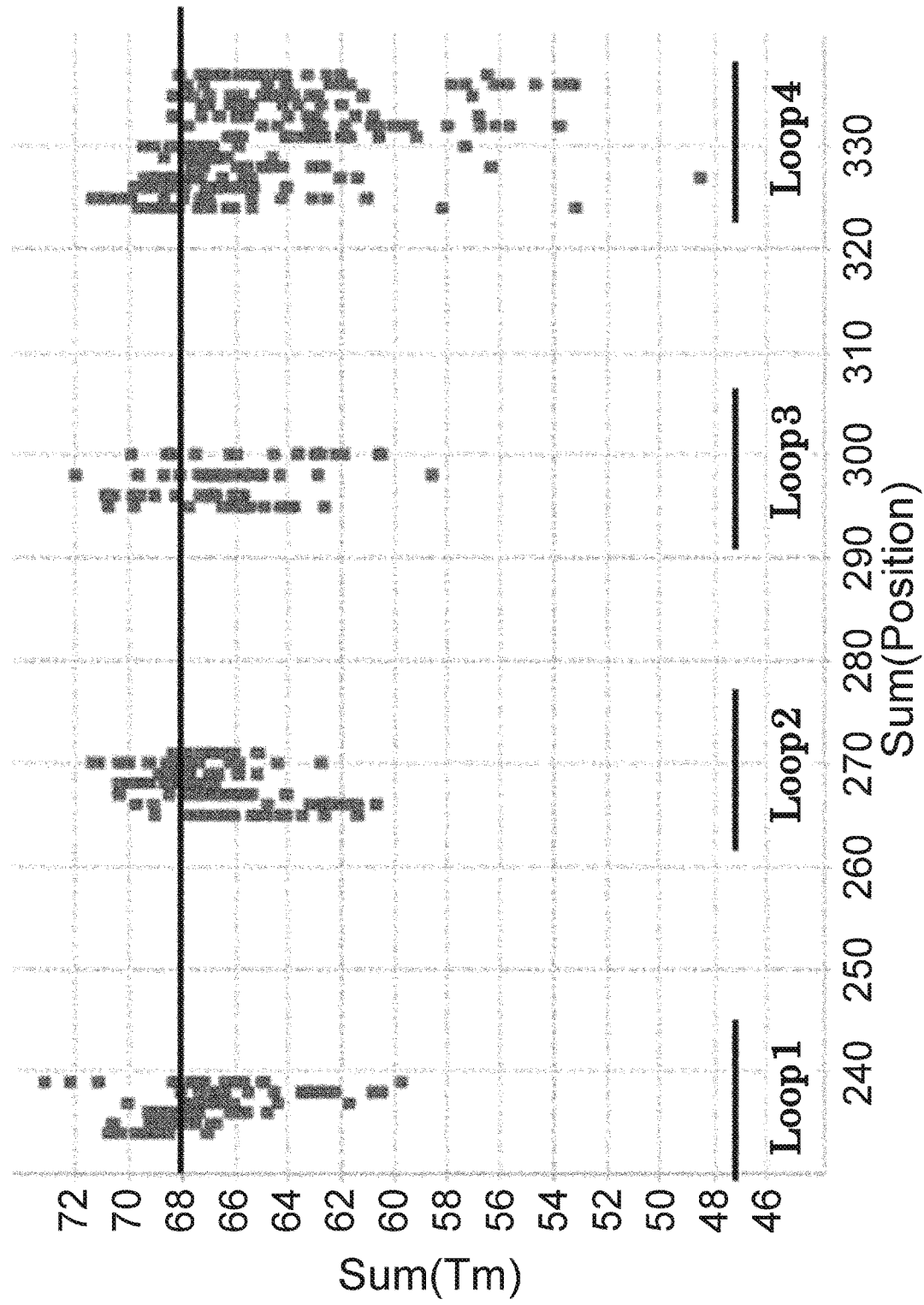
FIG. 1 shows the melting temperatures (Tm) of the produced antibodies.

The melting temperature (Tm) of the produced antibodies was evaluated according to the method of Reference Example 2. In the following, unless otherwise noted, "Tm" refers to the Tm of the CH2 domain when a sample in the form of IgG was subjected to measurement. The obtained Tm data are shown in FIG. 1.

The Tm of B3, which did not contain mutations (GpH7-B3/GpL16-k0: GpH7(SEQ ID NO: 17), B3 (SEQ ID NO: 16), GpL16(SEQ ID NO: 18), k0(SEQ ID NO: 19)), was approximately 68° C., and mutants showing a higher Tm than this value are shown in Tables 1-1 and 1-2.

TABLE 1-1

| Mutated residue | Amino acid after mutation | Tm (° C.) |
|---|---|---|
| L234 | G | 69.5 |
| | A | 68.8 |
| | V | 69.7 |
| | F | 68.5 |
| | P | 68.9 |
| | M | 68.9 |
| | I | 69.1 |
| | K | 70.8 |
| | R | 70.3 |
| | S | 69.3 |
| | T | 69.2 |
| | Y | 69.0 |
| | H | 69.0 |
| | N | 69.1 |
| | Q | 69.4 |
| | W | 68.9 |
| L235 | G | 69.0 |
| | A | 68.8 |
| | V | 69.2 |
| | F | 68.9 |
| | P | 68.9 |
| | M | 69.0 |
| | I | 69.1 |
| | K | 70.7 |
| | R | 70.6 |
| | S | 68.9 |
| | T | 68.4 |
| | Y | 68.8 |
| | N | 68.1 |
| G236 | A | 68.4 |
| | P | 68.9 |
| | L | 68.4 |
| | K | 69.3 |
| | R | 68.6 |
| | T | 68.9 |
| | H | 68.2 |
| | N | 68.1 |
| G237 | R | 70.1 |
| P238 | I | 68.1 |
| S239 | M | 68.4 |
| | K | 73.2 |
| | R | 72.2 |
| | T | 68.2 |
| | H | 68.2 |
| | Q | 71.2 |
| D265 | G | 69.0 |
| V266 | I | 69.1 |
| | L | 69.7 |
| S267 | P | 70.4 |
| | K | 68.5 |
| H268 | A | 68.5 |
| | V | 68.1 |
| | F | 69.6 |
| | P | 69.9 |
| | M | 70.0 |
| | I | 69.6 |
| | L | 69.9 |
| | K | 70.4 |
| | R | 69.2 |
| | T | 68.1 |
| | Y | 68.5 |
| | Q | 68.7 |
| | W | 68.5 |
| E269 | A | 68.6 |
| | V | 68.2 |
| | D | 68.6 |
| | K | 68.3 |
| | R | 68.9 |
| | S | 68.7 |
| | T | 68.1 |
| | H | 68.6 |

Table 1-2 is a continuation of Table 1-1.

TABLE 1-2

| Mutated residue | Amino acid after mutation | Tm (° C.) | Mutated residue | Amino acid after mutation | Tm (° C.) |
|---|---|---|---|---|---|
| D270 | A | 70.0 | N325 | G | 71.4 |
|  | F | 71.4 |  | A | 69.9 |
|  | M | 69.2 |  | V | 70.1 |
|  | E | 69.3 |  | F | 68.7 |
|  | T | 68.6 |  | M | 71.2 |
|  | Y | 71.2 |  | I | 70.3 |
|  | H | 71.4 |  | L | 70.4 |
|  | N | 70.2 |  | S | 71 |
|  | Q | 68.4 |  | T | 70.9 |
|  | W | 70.4 |  | H | 71.3 |
| P271 | D | 68.4 | K326 | G | 69.6 |
| Q295 | M | 70.8 |  | A | 69.2 |
|  | L | 69.8 |  | P | 68.4 |
| Y296 | G | 70.9 |  | R | 68.8 |
|  | F | 69 |  | S | 69.8 |
|  | D | 69.6 |  | N | 68.9 |
|  | E | 69 | A327 | F | 68.6 |
|  | S | 70.6 |  | M | 69 |
|  | T | 68.3 |  | L | 69.4 |
|  | N | 69.9 |  | K | 68.4 |
|  | Q | 70.8 |  | R | 69.1 |
| S298 | G | 72 |  | N | 68.2 |
|  | A | 68.1 | P329 | A | 68.7 |
|  | F | 68.7 | A330 | V | 68.5 |
|  | M | 69.7 |  | M | 68.2 |
| Y300 | G | 68.5 |  | I | 68.2 |
|  | P | 69.9 |  | K | 68.2 |
|  | D | 68.4 |  | Y | 69 |
|  | E | 68.6 |  | H | 69.5 |
| S324 | F | 69 |  | N | 68.2 |
|  | I | 68.4 | E333 | V | 68.4 |
|  | K | 68.2 |  | Q | 68.4 |
|  | R | 68.8 | T335 | V | 68.4 |
|  | Y | 68.6 | S337 | R | 68.1 |
|  | H | 69.3 |  |  |  |
|  | N | 69.7 |  |  |  |

[Example 2] Preparation and Evaluation of IgG1 with Novel Fc Regions that Improve Thermal Stability Based on the data from Example 1 and structural information (Nature 2000; 406: 267-273), several mutations presumed to be particularly effective for improving thermal stability were selected. One or more of the selected mutations were introduced into the H chains of the anti-GPC3 antibody (GpH7-G1d/GpL16-k0: GpH7 (SEQ ID NO: 17), G1d (SEQ ID NO: 15), GpL16 (SEQ ID NO: 18), k0 (SEQ ID NO: 19)) and the anti-IL6R antibody (MHO-G1d/MLO-k0: GpH7 (SEQ ID NO: 17), G1d (SEQ ID NO: 15), MLO (SEQ ID NO: 21), k0 (SEQ ID NO: 19)) to produce TS1 to TS19 (SEQ ID NOs: 26-44) shown in Table 2. At the same time, to evaluate effects on improvement of thermal stability by introduction of disulfide bond(s) in IgG form, the mutations of m01 and m02 reported in a prior document (J Biol. Chem. 2009; 284: 14203-14210) were introduced to the H chain of anti-IL6R to produce the TSm01 and TSm02 variants (SEQ ID NOs: 24 and 25). Each antibody was expressed and purified by the method of Reference Example 1.

TABLE 2

| Variant name | Alteration sites | SEQ ID NO: |
|---|---|---|
| G1d | WT | 15 |
| TS01 | L234I | 26 |
| TS02 | V266I/H268Q/E269D/D270E | 27 |
| TS03 | Q295M | 28 |
| TS04 | Q295M/Y300E | 29 |
| TS05 | Q295L | 30 |
| TS06 | K326S/A330H | 31 |
| TS07 | K326S/S324H/A330H | 32 |
| TS08 | K326A/A330Y | 33 |
| TS09 | L234K/L235K | 34 |
| TS10 | L234K/L235R | 35 |
| TS11 | L234R/L235K | 36 |
| TS12 | L234R/L235R | 37 |
| TS13 | S267P/H268M/D270F | 38 |
| TS14 | H268M/D270F | 39 |
| TS15 | H268K/D270F | 40 |
| TS16 | Q295M/Y296G/S298G | 41 |
| TS17 | S239K/N325G | 42 |
| TS18 | S239K/N325M | 43 |
| TS19 | S239K/N325H | 44 |
| TSm01 | L242C/K334C | 24 |
| TSm02 | V240C/K334C | 25 |

Using the prepared antibodies, Tm values were compared by the method described in Reference Example 2. The results of Tm measurements are shown in Table 3.

TABLE 3

| Constant region name | Tm (° C.) anti-GPC3 | Tm (° C.) anti-IL6R |
|---|---|---|
| TS1 | 69.5 | 70.5 |
| TS2 | 69.8 | 70.7 |
| TS3 | 71.1 | 72.4 |
| TS4 | 62.8 | 63.1 |
| TS5 | 70.1 | 71.4 |
| TS6 | 70.4 | 71.6 |
| TS7 | 69.8 | 70.8 |
| TS8 | 70.0 | 71.0 |
| TS9 | n.t. | 73.4 |
| TS10 | 71.6 | 73.8 |
| TS11 | 71.8 | 73.7 |
| TS12 | 71.9 | 73.9 |
| TS13 | 73.7 | 78.4 |
| TS14 | 72.3 | 74.2 |
| TS15 | 72.5 | 75.3 |
| TS16 | 73.5 | 80.0 |
| TS17 | 74.2 | 78.9 |
| TS18 | 73.6 | 77.9 |
| TS19 | 73.7 | 78.6 |
| B3 | 69.1 | n.t. |
| TSm01 | n.t. | n.d. |
| TSm02 | n.t. | 74.5 |
| G1 | 69.4 | 70.4 |

In the results, the samples that were not evaluated are indicated as "n.t." (not tested), and the samples for which Tm was difficult to detect are indicated as "n.d." (not detected).

From the variants of TS1-TS19, the variants of TS1-3 and TS5-19 showed improvement of Tm when both the H chain sequence of anti-GPC3 and that of anti-IL6R were used. On the other hand, TS4 showed a decrease in Tm for both H chain sequences. The alteration of Q295M, which was introduced into TS4, improved Tm by approximately 2° C. by itself alone (TS3), but was found to result in decreased Tm when the Y300E alteration was simultaneously introduced. According to the structural information, Q295 and Y300 are located opposite to each other on the same loop. The Q295M substitution may enhance the amino acid side chain interaction with Y300. However, it is speculated that simultaneous introduction of the Q295M and Y300E substitutions eliminated the interaction between the amino acid side chains.

As shown above, it was demonstrated that a combination of mutations improving Tm further improves Tm except for mutations having bad influence on structure. As such, in addition to TS1-3 and TS5-19 disclosed herein, it is possible to produce more combinations of Tm-improving alterations based on structural information.

With regard to TSm01 and TSm02, which were evaluated at the same time, the prior document (J Biol. Chem. 2009; 284:14203-14210) demonstrated that they increased Tm about 10° C. to 20° C. when the CH2 domain alone was expressed and evaluated for Tm. However, in the present examination where they were evaluated for Tm in the IgG form, multiple denaturation points were detected for TSm01, and it was difficult to clearly determine the thermal denaturation of the CH2 domain. This suggests a high possibility that TSm01 is structurally heterogeneous.

Furthermore, the Tm of TSm02 increased only by approximately 4° C. as compared to that of IgG1. This demonstrates that the introduction of disulfide bonds is less effective in improving Tm in the IgG form, and the mutations found by the present inventors are more effective for improving Tm.

Tm of Fab of the anti-GPC3 antibody used in this examination is 74.7° C. Therefore, with regard to TS13 to TS19, in which mutations have been introduced into the H chain of anti-GPC3, it was presumed that the fluorescence transition curves of CH2 and Fab would overlap, making accurate calculation of Tm difficult. Accordingly, as it was considered inappropriate to use the H chain of anti-GPC3 to test combinations effect on Tm, subsequent examinations were carried out using the H chain of anti-IL6R.

[Example 3] Assessment of Binding of Novel Fc Regions to Human Fcγ Receptors

Regarding modification of antibody Fc regions, there are reports of Fc regions with enhanced or reduced effector functions such as ADCC activity (reference: current opinion, 2009, 20, 685-691). Antibodies with enhanced effector functions may be useful mainly as antibodies for cancer therapy, and antibodies with reduced effector functions may be useful as, for example, neutralizing antibodies or receptor-Fc fusions such as Enbrel and Orencis. It is important that they are used appropriately depending on their respective purposes.

The CH2 domain, which was modified in this examination, is known to be involved in interaction with several human Fcγ receptors (hereinafter denoted as hFcgRs) which affect effector functions. Therefore, the binding of TS1 and TS19 prepared by using the H chain of anti-IL6R produced in Example 2 to hFcgRs was measured, according to the method described in Reference Example 3. The measurement results are summarized in Table 4, where the binding of each antibody to each hFcgR relative to the binding of G1 to each hFcgR, which was taken as 100, was calculated.

TABLE 4

| Variant name | hFcgRIa | hFcgRIIa (R) | hFcgRIIa (H) | hFcgRIIb | hFcgRIIIa (F) | hFcgRIIIa (V) |
| --- | --- | --- | --- | --- | --- | --- |
| TS1 | 96.5 | 67.0 | 76.8 | 61.5 | 62.4 | 83.5 |
| TS2 | 98.3 | 67.3 | 123.0 | 61.6 | 159.0 | 130.0 |
| TS3 | 97.5 | 89.6 | 115.3 | 84.2 | 63.8 | 90.1 |
| TS4 | 99.3 | 148.4 | 105.9 | 219.9 | 73.9 | 99.2 |
| TS5 | 97.3 | 128.8 | 142.1 | 157.5 | 86.6 | 106.1 |
| TS6 | 100.8 | 122.7 | 120.3 | 142.2 | 103.0 | 90.6 |
| TS7 | 99.8 | 116.6 | 118.1 | 125.9 | 98.8 | 86.2 |
| TS8 | 102.3 | 119.9 | 100.6 | 132.3 | 164.6 | 124.4 |
| TS9 | −1.9 | 1.3 | 0.5 | 1.4 | 1.1 | 0.5 |
| TS10 | 0.2 | 1.4 | 0.7 | 3.0 | 2.2 | 1.1 |
| TS11 | −0.2 | 1.5 | 1.3 | 3.4 | 2.6 | 1.4 |
| TS12 | −1.0 | 0.6 | 0.9 | 2.8 | 1.6 | 1.1 |
| TS13 | 63.0 | 1.2 | 1.2 | 3.4 | 1.8 | 1.4 |
| TS14 | 87.1 | 3.4 | 29.4 | 7.1 | 5.5 | 10.1 |
| TS15 | 80.8 | 4.5 | 30.6 | 9.1 | 5.9 | 10.1 |
| TS16 | 96.8 | 25.3 | 15.9 | 21.7 | 13.8 | 28.9 |
| TS17 | 9.0 | 2.7 | 1.0 | 6.0 | 4.4 | 1.9 |
| TS18 | 11.5 | 7.9 | 2.3 | 10.9 | 3.9 | 1.8 |
| TS19 | 10.7 | 3.5 | 2.3 | 8.1 | 3.8 | 4.2 |

The results showed that while the binding of TS1 to TS8 to hFcgRs was equivalent to that of G1, the binding of TS9-19 to hFcgRs was weaker than that of G1.

[Example 4] Production and Evaluation of Novel Fc Regions with Combined Mutations that Maintain Binding Ability to hFcgRs When mutations with improving stability are introduced, it is important that antibodies for cancer therapy, whose effector functions are important, retain binding ability to hFcgRs. The mutations of TS1 to TS8, which were found to maintain binding ability to hFcgRs in Example 3, were combined to produce new variants TS20 to TS27 as shown in Table 5 (SEQ ID NOs: 45 to 52). Each antibody was expressed and purified by the method described in Reference Example 1. The prepared antibodies were subjected to Tm assessment by the method of Reference Example 2, and the results are shown in Table 6.

TABLE 5

| Variant name | Alteration sites | SEQ ID NO: |
| --- | --- | --- |
| TS20 | Q295M/K326S/A330H | 45 |
| TS21 | Q295M/K326A/A330Y | 46 |
| TS22 | Q295L/K326S/A330H | 47 |
| TS23 | Q295L/K326A/A330Y | 48 |

TABLE 5-continued

| Variant name | Alteration sites | SEQ ID NO: |
| --- | --- | --- |
| TS24 | Q295M/K326S/A330Y | 49 |
| TS25 | Q295M/K326A/A330H | 50 |
| TS26 | Q295L/K326S/A330Y | 51 |
| TS27 | Q295L/K326A/A330H | 52 |

TABLE 6

| Variant name | Tm (° C.) |
| --- | --- |
| TS20 | 73.4 |
| TS21 | 72.8 |
| TS22 | 72.3 |
| TS23 | 71.7 |
| TS24 | 73.4 |
| TS25 | 72.8 |
| TS26 | 72.2 |
| TS27 | 71.7 |
| G1 | 70.4 |

Furthermore, binding ability to hFcgRs was measured by the method described in Reference Example 3. Binding of each antibody to each hFcgR was calculated relative to the binding of G1 to each hFcgR, which was taken as 100, and the results are shown in Table 7.

TABLE 7

| Variant name | hFcgRIa | hFcgRIIa (R) | hFcgRIIa (H) | hFcgRIIb | hFcgRIIIa (F) | hFcgRIIIa (V) |
| --- | --- | --- | --- | --- | --- | --- |
| TS20 | 105.8 | 116.5 | 132.1 | 130.9 | 105.0 | 91.2 |
| TS21 | 107.2 | 113.1 | 114.0 | 121.2 | 164.2 | 124.3 |
| TS22 | 107.7 | 152.7 | 157.2 | 231.9 | 138.2 | 107.4 |
| TS23 | 109.0 | 152.9 | 144.7 | 226.2 | 219.6 | 136.7 |
| TS24 | 106.9 | 106.9 | 122.3 | 113.5 | 155.1 | 121.4 |
| TS25 | 104.8 | 122.9 | 124.7 | 137.0 | 113.5 | 92.8 |
| TS26 | 106.8 | 145.3 | 151.5 | 208.4 | 204.4 | 134.0 |
| TS27 | 106.3 | 157.8 | 151.1 | 241.5 | 147.6 | 108.7 |

For all variants of TS20 to TS27, combining the mutations resulted in improved Tm while maintaining the binding ability to hFcgRs. The variants which were the most effective to improve Tm were TS20 and TS24, and they increase Tm approximately 3° C. as compared to G1.

[Example 5] Production and Evaluation of Novel Fc Regions with Combined Mutations that Reduce Binding Ability to hFcgRs When mutations for improving stability are introduced into neutralizing antibodies, it is preferred to have as low effector functions as possible. The mutations of TS9 to TS19, which were found out to reduce binding affinity to hFcgRs in Example 3, were combined to produce new variants TS28 to TS43 as shown in Table 8 (SEQ ID NOs: 53 to 68). Each antibody was expressed and purified by the method described in Reference Example 1. The prepared antibodies were subjected to Tm assessment by the method of Reference Example 2, and the results are shown in Table 9.

TABLE 8

| Variant name | Alteration sites | SEQ ID NO: |
| --- | --- | --- |
| TS28 | L234K/L235K/S239K/H268K/D270F/Q295M/Y296G/S298G/N325G | 53 |
| TS29 | L234K/L235K/S239K/H268K/D270F/Q295M/Y296G/S298G/N325H | 54 |
| TS30 | L234K/L235K/S239K/Q295M/Y296G/S298G/N325G | 55 |
| TS31 | L234K/L235K/S239K/Q295M/Y296G/S298G/N325H | 56 |

TABLE 8-continued

| Variant name | Alteration sites | SEQ ID NO: |
|---|---|---|
| TS32 | L234K/L235K/H268K/D270F/Q295M/Y296G/S298G/N325G | 57 |
| TS33 | L234K/L235K/H268K/D270F/Q295M/Y296G/S298G/N325H | 58 |
| TS34 | L234K/L235K/Q295M/Y296G/S298G/N325G | 59 |
| TS35 | L234K/L235K/Q295M/Y296G/S298G/N325H | 60 |
| TS36 | L234K/L235R/S239K/H268K/D270F/Q295M/Y296G/S298G/N325G | 61 |
| TS37 | L234K/L235R/S239K/H268K/D270F/Q295M/Y296G/S298G/N325H | 62 |
| TS38 | L234K/L235R/S239K/Q295M/Y296G/S298G/N325G | 63 |
| TS39 | L234K/L235R/S239K/Q295M/Y296G/S298G/N325H | 64 |
| TS40 | L234K/L235R/H268K/D270F/Q295M/Y296G/S298G/N325G | 65 |
| TS41 | L234K/L235R/H268K/D270F/Q295M/Y296G/S298G/N325H | 66 |
| TS42 | L234K/L235R/Q295M/Y296G/S298G/N325G | 67 |
| TS43 | L234K/L235R/Q295M/Y296G/S298G/N325H | 68 |

TABLE 9

| Variant name | Tm (° C.) |
|---|---|
| TS28 | 85.8 |
| TS29 | 84.6 |
| TS30 | 86.6 |
| TS31 | 86.2 |
| TS32 | 84.9 |
| TS33 | 83.5 |
| TS34 | 85.3 |
| TS35 | 84.8 |
| TS36 | 86.0 |
| TS37 | 85.0 |
| TS38 | 86.6 |
| TS39 | 85.9 |
| TS40 | 85.1 |
| TS41 | 83.8 |
| TS42 | 85.4 |
| TS43 | 84.9 |
| G1 | 70.4 |

Furthermore, binding ability to hFcgRs was measured by the method described in Reference Example 3. Binding of each antibody to each hFcgR was calculated relative to the binding of G1 to each hFcgR, which was taken as 100, and the results are shown in Table 10.

TABLE 10

| Variant name | hFcgRIa | hFcgRIIa (R) | hFcgRIIa (H) | hFcgRIIb | hFcgRIIIa (F) | hFcgRIIIa (V) |
|---|---|---|---|---|---|---|
| TS28 | 5.8 | 1.9 | 1.7 | 7.2 | 3.8 | 1.7 |
| TS29 | 5.1 | 2.1 | 0.7 | 7.2 | 4.2 | 1.6 |
| TS30 | 0.1 | 1.2 | 0.2 | 3.8 | 0.7 | 1.1 |
| TS31 | 0.2 | 1.3 | −0.5 | 3.6 | 1.9 | 1.2 |
| TS32 | −0.5 | 0.9 | 1.0 | 1.5 | 0.8 | 0.9 |
| TS33 | −0.9 | 1.2 | 0.7 | 4.6 | 0.7 | 1.0 |
| TS34 | −0.9 | 0.9 | 1.4 | 4.2 | 1.8 | 1.5 |
| TS35 | 0.5 | 1.1 | 1.7 | 6.2 | 2.0 | 1.5 |
| TS36 | −0.4 | 1.0 | 0.7 | 4.1 | 0.7 | 1.1 |
| TS37 | 0.6 | 0.9 | 0.7 | 4.5 | 1.4 | 0.6 |
| TS38 | 0.3 | 2.3 | 1.7 | 5.8 | 2.9 | 0.9 |
| TS39 | 0.0 | 1.5 | 1.0 | 2.5 | 2.4 | 0.8 |
| TS40 | −1.8 | 1.2 | 0.7 | 0.3 | 0.5 | 1.0 |
| TS41 | 0.2 | 1.2 | 1.4 | 4.2 | 2.4 | 1.0 |
| TS42 | −0.2 | 1.3 | 1.6 | 6.9 | 2.5 | 1.3 |
| TS43 | −0.9 | 1.7 | −0.1 | 6.2 | 2.7 | 1.1 |

For all the variants of TS28 to TS43, combining the mutations increased Tm by 13° C. or more. Furthermore, combining the mutations greatly reduced the binding ability to FcgRs.

[Example 6] Assessment of Aggregate Content of IgG1 with Novel Fc Regions Having Improved Thermal Stability Since aggregates affect storage stability and immunogenicity, it is preferred that mutations for improving thermal stability should not increase the content of aggregate. Accordingly, TS20 to TS43, which combine multiple mutations, and TSm01, and TSm02 were assessed for aggregate content by the method of Reference Example 4. The chromatograms for the measurement are shown in FIG. 2, and the aggregate contents are shown in Table 11.

TABLE 11

| Variant name | Aggregate content (%) |
| --- | --- |
| TS20 | 1.73 |
| TS21 | 1.70 |
| TS22 | 1.84 |
| TS23 | 1.71 |
| TS24 | 1.66 |
| TS25 | 1.45 |
| TS26 | 1.82 |
| TS27 | 1.96 |
| TS28 | 2.00 |
| TS29 | 3.03 |
| TS30 | 2.72 |
| TS31 | 2.67 |
| TS32 | 2.08 |
| TS33 | 3.77 |
| TS34 | 2.31 |
| TS35 | 2.90 |
| TS36 | 1.86 |
| TS37 | 1.69 |
| TS38 | 2.22 |
| TS39 | 2.19 |
| TS40 | 1.53 |
| TS41 | 2.49 |
| TS42 | 2.04 |
| TS43 | 1.95 |
| TSm01 | 7.44 |
| TSm02 | 4.11 |
| G1 | 1.49 |

TS20 to TS27, which maintain the binding ability to hFcgRs, showed comparable aggregation content to G1, demonstrating that these thermal stability-improving mutations were found not to have a large effect on aggregate content. On the other hand, for TS28 to TS43, which greatly reduced the binding ability to hFcgRs, while the amount of aggregates was slightly increased in TS29, 33, and 35, the other variants showed almost the same aggregate amount as that of G1. In contrast, the disulfide bond-introduced variants TSm01 and TSm02 showed a significant increase in the aggregate content, that is, about 5 times and 3 times that of G1, respectively.

The above-mentioned results demonstrate that the mutations discovered in this examination by the present inventors are first-ever mutations that improved the thermal stability while maintaining the physicochemical properties.

[Example 7] Production and Evaluation of IgG1 with Novel Fc Regions that Improve Thermal Stability The above-mentioned result showed that introducing mutations to the CH2 domain improves the Tm. Therefore, regions that had not been examined for introduction of mutations in Example 1 were examined for whether there were any mutations to improve the Tm, and new variants TS44 to TS67 as shown in Table 12 were produced (SEQ ID NOs: 69-92). Each antibody was expressed and purified by the method described in Reference Example 1 and the results are shown in Table 13. Furthermore, binding ability to hFcgRs was measured by the method described in Reference Example 3. Binding of each antibody to each hFcgR was calculated relative to the binding of G1 to each hFcgR, which was taken as 100, and the results are shown in Table 14.

TABLE 12

| Variant name | Alteration sites | SEQ ID NO: |
| --- | --- | --- |
| TS44 | P247V | 69 |
| TS45 | T250F | 70 |
| TS46 | T250I | 71 |
| TS47 | T250M | 72 |
| TS48 | T250V | 73 |
| TS49 | T250W | 74 |
| TS50 | T250Y | 75 |
| TS51 | S298G | 76 |
| TS52 | T307A | 77 |
| TS53 | T307Q | 78 |
| TS54 | T307P | 79 |
| TS55 | L309A | 80 |
| TS56 | L309D | 81 |
| TS57 | L309R | 82 |
| TS58 | L309P | 83 |
| TS59 | N315A | 84 |
| TS60 | K360H | 85 |
| TS61 | G385D/Q386P/N389S | 86 |
| TS62 | P387E | 87 |
| TS63 | M428H | 88 |
| TS64 | M428W | 89 |
| TS65 | M428Y | 90 |
| TS66 | M428F | 91 |
| TS67 | H433K | 92 |

TABLE 13

| Variant name | Tm (° C.) |
| --- | --- |
| TS44 | 72.0 |
| TS45 | 74.1 |
| TS46 | 73.9 |
| TS47 | 69.3 |
| TS48 | 75.5 |
| TS49 | 71.5 |
| TS50 | 75.1 |
| TS51 | 73.5 |
| TS52 | 70.8 |
| TS53 | 71.2 |
| TS54 | 74.1 |
| TS55 | 71.4 |
| TS56 | 72.5 |
| TS57 | 72.6 |
| TS58 | 68.3 |
| TS59 | 71.8 |
| TS60 | 70.2 |
| TS61 | 70.1 |
| TS62 | 72.0 |
| TS63 | 69.3 |
| TS64 | 74.7 |
| TS65 | 73.3 |
| TS66 | 72.8 |
| TS67 | 70.3 |
| G1 | 70.4 |

TABLE 14

| Variant name | hFcgRIa | hFcgRIIa (R) | hFcgRIIa (H) | hFcgRIIb | hFcgRIIIa (F) | hFcgRIIIa (V) |
|---|---|---|---|---|---|---|
| TS44 | 101.3 | 103.4 | 110.2 | 112.6 | 92.0 | 102.9 |
| TS45 | 104.9 | 125.1 | 119.3 | 150.2 | 62.8 | 84.7 |
| TS46 | 99.2 | 102.3 | 104.6 | 104.6 | 66.1 | 89.6 |
| TS47 | 100.7 | 126.6 | 114.4 | 162.9 | 49.8 | 72.0 |
| TS48 | 101.5 | 111.3 | 108.4 | 113.2 | 66.0 | 89.4 |
| TS49 | 99.6 | 123.7 | 126.6 | 148.3 | 82.0 | 96.9 |
| TS50 | 101.5 | 136.6 | 129.3 | 169.4 | 83.5 | 98.9 |
| TS51 | 99.2 | 55.8 | 27.4 | 40.8 | 36.0 | 58.9 |
| TS52 | 98.8 | 98.3 | 101.8 | 97.2 | 64.6 | 89.0 |
| TS53 | 101.2 | 99.0 | 102.8 | 95.9 | 66.4 | 90.8 |
| TS54 | 102.7 | 103.3 | 103.5 | 102.3 | 66.8 | 90.6 |
| TS55 | 99.2 | 101.4 | 104.1 | 106.4 | 70.2 | 90.5 |
| TS56 | 67.0 | 76.7 | 79.2 | 74.3 | 47.2 | 69.1 |
| TS57 | 101.1 | 97.0 | 98.1 | 97.8 | 61.4 | 86.2 |
| TS58 | 96.4 | 68.7 | 82.2 | 70.4 | 41.5 | 61.2 |
| TS59 | 101.8 | 99.1 | 100.0 | 99.0 | 73.4 | 96.1 |
| TS60 | 104.7 | 102.7 | 104.8 | 99.7 | 70.3 | 94.2 |
| TS61 | 100.9 | 106.2 | 106.4 | 112.4 | 73.4 | 96.6 |
| TS62 | 101.3 | 99.7 | 101.8 | 95.6 | 68.9 | 91.7 |
| TS63 | 98.6 | 102.1 | 102.2 | 108.5 | 71.7 | 90.3 |
| TS64 | 99.4 | 114.9 | 110.8 | 124.4 | 89.2 | 104.7 |
| TS65 | 100.8 | 108.9 | 110.8 | 111.4 | 76.3 | 96.8 |
| TS66 | 103.2 | 111.5 | 112.9 | 114.6 | 78.8 | 99.2 |
| TS67 | 99.0 | 99.7 | 103.1 | 97.7 | 66.0 | 91.7 |

The variant with the highest Tm in this examination was TS48, and increased Tm approximately 5° C. The other variants also showed improvement in the Tm. The binding ability of TS51 and TS56 to hFcgRs was slightly decreased, and the others maintained their hFcgRs-binding ability.

[Reference Example 1] Production of Antibody Expression Vectors and Expression and Purification of Antibodies Amino acid substitutions were introduced by methods known to those skilled in the art using the QuikChange Site-Directed Mutagenesis Kit (Stratagene), PCR, and such, or the In fusion Advantage PCR cloning kit (TAKARA), and then expression vectors were constructed. The nucleotide sequences of the obtained expression vectors were determined by methods known to those skilled in the art. The produced plasmids were transiently introduced into human embryonic kidney cancer-derived cell line HEK293H (Invitrogen) or FreeStyle293 (Invitrogen) to express antibodies. From the resulting culture supernatant, antibodies were purified by methods known to those skilled in the art using the rProtein A Sepharose™ Fast Flow (GE Healthcare). The concentrations of the purified antibodies were determined by measuring absorbance at 280 nm using a spectrophotometer, and calculating from the measured values using an extinction coefficient determined by the PACE method (Protein Science 1995; 4: 2411-2423).

[Reference Example 2] Assessment of Melting Temperature (Tm) of the Modified Antibodies by Differential Scanning Fluorimetry In this examination, thermal stability was assessed by measuring the melting temperature (Tm) of antibodies by differential scanning fluorimetry using Rotor-Gene Q (QIAGEN). It has been reported that this method shows a good correlation with Tm assessment that uses differential scanning calorimetry, which is a widely known method for evaluating thermal stability of antibodies (Journal of Pharmaceutical Science 2010; 4: 1707-1720).

The 5000 times concentrated SYPRO orange (Molecular Probes) was diluted with PBS (Sigma), and then added to the antibody solutions to prepare measurement samples. A 20 μL aliquot of each sample was placed into a measurement tube, and the temperature was increased from 30° C. to 99° C. at 0.4° C. increments with an equilibration time of approximately six seconds before measurement of fluorescence intensity at 470 nm (excitation wavelength)/555 nm (fluorescence wavelength).

The data were analyzed using Rotor-Gene Q Series Software (QIAGEN) to calculate the temperature at which fluorescence transition was observed, and this temperature was defined as Tm.

[Reference Example 3] Assessment of Binding Ability to hFcgRs

Interactions between antibodies and hFcgRs (hFcgRIa, hFcgRIIa(R), hFcgRIIa(H), hFcgRIIb, hFcgRIIIa(F), and hFcgRIIIa(V)) were analyzed using Biacore T100 (GE Healthcare). HBS-EP+(GE Healthcare) was used for the running buffer, and the measurement temperature was set at 25° C. Protein A (Invitrogen) was immobilized by the amino coupling method, and an antibody of interest was captured thereon. Then, hFcγR solutions diluted using the running buffer were injected to allow interaction with the captured antibody at a flow rate of 30 μL/min for five minutes for hFcγRIa, and at a flow rate of 5 μL/min for one minute for the other hFcγRs. The level of binding ability to the antibody was determined, and the results were compared among the antibodies. Since the hFcγR binding level depends on the amount of captured antibodies, the FcgR-binding levels were corrected so that the capture level of each antibody would be 200 RU (resonance unit) for hFcgRIa and 1000 RU (resonance unit) for the other hFcgRs. The captured antibodies were washed by allowing 10 mM glycine-HCl (pH 1.5) to react for 30 seconds at a flow rate of 30 μL/min to recycle the chip for reuse.

[Reference Example 4] Evaluation of Aggregate Content

The aggregate content in the purified antibody was evaluated by SEC analysis using the Alliance system (Waters). The mobile phase was 50 mM phosphate buffer containing 300 mM sodium chloride (pH7.0, Isekyu), the analytical column was G3000SW$_{XL}$ (TOSOH), and measurements were taken at a wavelength of 215 nm. The data were analyzed using Empower2 (Waters). Components that eluted as higher molecular weight species than the monomer were collectively taken as aggregates, and their content was calculated.

INDUSTRIAL APPLICABILITY

In the reported antibody Fc region variants, the stability of the Fc region is reduced in most cases. In addition, it is important that an antibody Fc region has effector functions, that is, binds to FcγRs. By the present invention, it is possible to provide highly stable Fc region variants maintaining FcγR-binding, or highly stable Fc region variants with reduced FcγR-binding.

The invention claimed is:

1. A method of producing an antibody comprising a modified human IgG1 Fc region, the method comprising producing the antibody by expression of nucleic acid encoding the antibody, wherein the amino acid sequence of the modified human IgG1 Fc region comprises one of the following sets of amino acid substitutions at the indicated EU numbering positions:
L234K/L235K/S239K/H268K/D270F/Q295M/Y296G/S298G/N325G,
L234K/L235K/S239K/H268K/D270F/Q295M/Y296G/S298G/N325H,
L234K/L235K/S239K/Q295M/Y296G/S298G/N325G,
L234K/L235K/S239K/Q295M/Y296G/S298G/N325H,
L234K/L235K/H268K/D270F/Q295M/Y296G/S298G/N325G,
L234K/L235K/H268K/D270F/Q295M/Y296G/S298G/N325H,
L234K/L235K/Q295M/Y296G/S298G/N325G,
L234K/L235K/Q295M/Y296G/S298G/N325H,
L234K/L235R/S239K/H268K/D270F/Q295M/Y296G/S298G/N325G,
L234K/L235R/S239K/H268K/D270F/Q295M/Y296G/S298G/N325H,
L234K/L235R/S239K/Q295M/Y296G/S298G/N325G,
L234K/L235R/S239K/Q295M/Y296G/S298G/N325H,
L234K/L235R/H268K/D270F/Q295M/Y296G/S298G/N325G,
L234K/L235R/H268K/D270F/Q295M/Y296G/S298G/N325H,
L234K/L235R/Q295M/Y296G/S298G/N325G,
L234K/L235R/Q295M/Y296G/S298G/N325H.

2. The method of claim 1, wherein the thermal stability of the antibody, as determined by measuring the melting temperature (Tm) of the antibody, is greater than the thermal stability of a control protein comprising a human IgG1 Fc region with no substitutions.

3. The method of claim 2, wherein the antibody binds to a human FcγR receptor with a binding activity that is lower than the binding activity of the control protein for the human FcγR receptor.

4. The method of claim 1, the method further comprising determining the thermal stability of the antibody.

5. The method of claim 4, wherein the thermal stability of the antibody is determined by measuring the Tm of the antibody.

6. The method of claim 2, the method further comprising conducting an assay to confirm that the thermal stability of the antibody is greater than the thermal stability of the control protein.

7. A method of producing an antibody comprising a modified human IgG1 Fc region, the method comprising:
(a) selecting an antibody comprising the amino acid sequence of a modified human IgG1 Fc region, wherein
(i) the amino acid sequence of the modified antibody-human IgG1 Fc region comprises one of the following sets of amino acid substitutions at the indicated EU numbering positions:
L234K/L235K/S239K/H268K/D270F/Q295M/Y296G/S298G/N325G,
L234K/L235K/S239K/H268K/D270F/Q295M/Y296G/S298G/N325H,
L234K/L235K/S239K/Q295M/Y296G/S298G/N325G,
L234K/L235K/S239K/Q295M/Y296G/S298G/N325H,
L234K/L235K/H268K/D270F/Q295M/Y296G/S298G/N325G,
L234K/L235K/H268K/D270F/Q295M/Y296G/S298G/N325H,
L234K/L235K/Q295M/Y296G/S298G/N325G,
L234K/L235K/Q295M/Y296G/S298G/N325H,
L234K/L235R/S239K/H268K/D270F/Q295M/Y296G/S298G/N325G,
L234K/L235R/S239K/H268K/D270F/Q295M/Y296G/S298G/N325H,
L234K/L235R/S239K/Q295M/Y296G/S298G/N325G,
L234K/L235R/S239K/Q295M/Y296G/S298G/N325H,
L234K/L235R/H268K/D270F/Q295M/Y296G/S298G/N325G,
L234K/L235R/H268K/D270F/Q295M/Y296G/S298G/N325H,
L234K/L235R/Q295M/Y296G/S298G/N325G,
L234K/L235R/Q295M/Y296G/S298G/N325H,
and (ii) the thermal stability of the modified human IgG1 Fc region is greater than the thermal stability of a naturally occurring human IgG Fc region, and the greater thermal stability is a basis for selecting the antibody in step (a); and (b) producing the selected antibody by expression of nucleic acid encoding the antibody.

8. The method of claim 1, wherein the antibody comprises antibody heavy chains and antibody light chains.

9. The method of claim 7, wherein the modified antibody Fc region further comprises a lysine residue at EU numbering position 409.

10. The method of claim 1, wherein the modified antibody Fc region has a deletion of EU numbering positions 446 and 447.

11. The method of claim 7, wherein the modified antibody Fc region has a deletion of EU numbering positions 446 and 447.

12. The method of claim 2, wherein the ability of the antibody to bind to each of the following human FcγR receptors is lower than the ability of the control protein to bind to the same human FcγR receptor: hFcγRIa, hFcγRIIaR, hFcγRIIaH, hFcγRIIb, hFcγRIIIaF, and hFcγRIIIaV.

13. The method of claim 1, further comprising collecting the produced antibody.

\* \* \* \* \*

SEQUENCE LISTING

```
<160> NUMBER OF SEQ ID NOS: 92

<210> SEQ ID NO 1
<211> LENGTH: 2268
<212> TYPE: DNA
<213> ORGANISM: Homo sapiens

<400> SEQUENCE: 1
aatatcttgc atgttacaga tttcactgct cccaccagct tggagacaac atgtggttct      60
tgacaactct gctcctttgg gttccagttg atgggcaagt ggacaccaca aaggcagtga     120
tcactttgca gcctccatgg gtcagcgtgt tccaagagga aaccgtaacc ttgcactgtg     180
aggtgctcca tctgcctggg agcagctcta cacagtggtt tctcaatggc acagccactc     240
agacctcgac ccccagctac agaatcacct ctgccagtgt caatgacagt ggtgaataca     300
ggtgccagag aggtctctca gggcgaagtg accccataca gctggaaatc cacagaggct     360
ggctactact gcaggtctcc agcagagtct tcacggaagg agaacctctg gccttgaggt     420
gtcatgcgtg gaaggataag ctggtgtaca atgtgcttta ctatcgaaat ggcaaagcct     480
ttaagttttt ccactggaat tctaacctca ccattctgaa aaccaacata agtcacaatg     540
gcacctacca ttgctcaggc atgggaaagc atcgctacac atcagcagga atatctgtca     600
ctgtgaaaga gctatttcca gctccagtgc tgaatgcatc tgtgacatcc ccactcctgg     660
aggggaatct ggtcacccctg agctgtgaaa caaagttgct cttgcagagg cctggtttgc     720
agctttactt ctccttctac atgggcagca agaccctgcg aggcaggaac acatcctctg     780
aataccaaat actaactgct agaagagaag actctgggtt atactggtgc gaggctgcca     840
cagaggatgg aaatgtcctt aagcgcagcc ctgagttgga gcttcaagtg cttggcctcc     900
agttaccaac tcctgtctgg tttcatgtcc ttttctatct ggcagtggga ataatgtttt     960
tagtgaacac tgttctctgg gtgacaatac gtaaagaact gaaaagaaag aaaaagtggg    1020
atttagaaat ctctttggat tctggtcatg agaagaaggt aatttccagc cttcaagaag    1080
acagacattt agaagaagag ctgaaatgtc aggaacaaaa agaagaacag ctgcaggaag    1140
gggtgcaccg gaaggagccc caggggcca cgtagcagcg gctcagtggg tggccatcga    1200
tctggaccgt cccctgccca cttgctcccc gtgagcactg cgtacaaaca tccaaaagtt    1260
caacaacacc agaactgtgt gtctcatggt atgtaactct taaagcaaat aaatgaactg    1320
acttcaactg ggatacattt ggaaatgtgg tcatcaaaga tgacttgaaa tgaggcctac    1380
tctaaagaat tcttgaaaaa cttacaagtc aagcctagcc tgataatcct attacatagt    1440
ttgaaaaata gtattttatt tctcagaaca aggtaaaaag gtgagtgggt gcatatgtac    1500
agaagattaa gacagagaaa cagacagaaa gagacacaca cacagccagg agtgggtaga    1560
```

```
tttcaggag  acaagaggga  atagtataga  caataaggaa  ggaaatagta  cttacaaatg    1620
actcctaagg  gactgtgaga  ctgagagggc  tcacgcctct  gtgttcagga  tacttagttc    1680
atggcttttc  tctttgactt  tactaaaaga  gaatgtctcc  atacgcgttc  taggcataca    1740 aggggtaac   tcatgatgag  aaatggatgt  gttattcttg  ccctctcttt  tgaggctctc    1800
tcataacccc  tctatttcta  gagacaacaa  aaatgctgcc  agtcctaggc  ccctgccctg    1860
taggaaggca  gaatgtaact  gttctgtttg  tttaacgatt  aagtccaaat  ctccaagtgc    1920
ggcactgcaa  agagacgctt  caagtgggga  gaagcggcga  taccatagag  tccagatctt    1980
gcctccagag  atttgcttta  ccttcctgat  tttctggtta  ctaattagct  tcaggatacg    2040
ctgctctcat  acttgggctg  tagtttggag  acaaaatatt  ttcctgccac  tgtgtaacat    2100
agctgaggta  aaaactgaac  tatgtaaatg  actctactaa  aagtttaggg  aaaaaaaaca    2160
ggaggagtat  gacacaaaaa  aaaaaaaaaa  aaaaaaaaaa  aaaaaaaaaa  aaaaaaaaaa    2220
aaaaaaaaaa  aaaaaaaaaa  aaaaaaaaaa  aaaaaaaaaa  aaaaaaaa                  2268
```

<210> SEQ ID NO 2
<211> LENGTH: 374
<212> TYPE: PRT
<213> ORGANISM: Homo sapiens

<400> SEQUENCE: 2

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
```

| | | 245 | | | | 250 | | | | 255 | | |
|---|---|---|---|---|---|---|---|---|---|---|---|---|

Leu Tyr Trp Cys Glu Ala Ala Thr Glu Asp Gly Asn Val Leu Lys Arg
              260                 265                 270

Ser Pro Glu Leu Glu Leu Gln Val Leu Gly Leu Gln Leu Pro Thr Pro
            275                 280                 285

Val Trp Phe His Val Leu Phe Tyr Leu Ala Val Gly Ile Met Phe Leu
        290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
                340                 345                 350

Cys Gln Glu Gln Lys Glu Glu Gln Leu Gln Glu Gly Val His Arg Lys
            355                 360                 365

Glu Pro Gln Gly Ala Thr
        370

<210> SEQ ID NO 3
<211> LENGTH: 1396
<212> TYPE: DNA
<213> ORGANISM: Homo sapiens

<400> SEQUENCE: 3

```
gggatgacta tggagaccca aatgtctcag aatgtatgtc ccagaaacct gtggctgctt      60
caaccattga cagttttgct gctgctggct tctgcagaca gtcaagctgc tcccccaaag     120
gctgtgctga acttgagcc cccgtggatc aacgtgctcc aggaggactc tgtgactctg     180
acatgccagg gggctcgcag ccctgagagc gactccattc agtggttcca caatgggaat     240
ctcattccca cccacacgca gcccagctac aggttcaagg ccaacaacaa tgacagcggg     300
gagtacacgt gccagactgg ccagaccagc ctcagcgacc ctgtgcatct gactgtgctt     360
tccgaatggc tggtgctcca gacccctcac ctggagttcc aggagggaga accatcatg     420
ctgaggtgcc acagctggaa ggacaagcct ctggtcaagg tcacattctt ccagaatgga     480
aaatcccaga attctcccca tttggatccc accttctcca tcccacaagc aaaccacagt     540
cacagtggtg attaccactg cacaggaaac ataggctaca cgctgttctc atccaagcct     600
gtgaccatca ctgtccaagt gcccagcatg ggcagctctt accaatgggg ggtcattgtg     660
gctgtggtca ttgcgactgc tgtagcagcc attgttgctg ctgtagtggc cttgatctac     720
tgcaggaaaa agcggatttc agccaattcc actgatcctg tgaaggctgc ccaatttgag     780
ccacctggac gtcaaatgat tgccatcaga aagagacaac ttgaagaaac caacaatgac     840
tatgaaacag ctgacggcgg ctacatgact ctgaacccca gggcacctac tgacgatgat     900
aaaaacatct acctgactct tcctcccaac gaccatgtca acagtaataa ctaaagagta     960
acgttatgcc atgtggtcat actctcagct tgctgagtgg atgacaaaaa gaggggaatt    1020
gttaaaggaa aatttaaatg gagactggaa aaatcctgag caaacaaaac cacctggccc    1080
ttagaaatag ctttaacttt gcttaaacta caaacacaag caaaacttca cggggtcata    1140
ctacatacaa gcataagcaa aacttaactt ggatcatttc tggtaaatgc ttatgttaga    1200
aataagacaa ccccagccaa tcacaagcag cctactaaca tataattagg tgactaggga    1260
cttttctaaga agatacctac ccccaaaaaa caattatgta attgaaaacc aaccgattgc    1320
ctttattttg cttccacatt ttcccaataa atacttgcct gtgactaaaa aaaaaaaaaa    1380
```
aaaaaaaaaa aaaaa                                               1396

<210> SEQ ID NO 4
<211> LENGTH: 316
<212> TYPE: PRT
<213> ORGANISM: Homo sapiens

<400> SEQUENCE: 4

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 5
<211> LENGTH: 1497
<212> TYPE: DNA
<213> ORGANISM: Homo sapiens

<400> SEQUENCE: 5

| | |
|---|---:|
| tgtgactgct gtgctctggg cgccagctcg ctccaggag tgatgggaat cctgtcattc | 60 |
| ttacctgtcc ttgccactga gagtgactgg gctgactgca agtcccccca gccttggggt | 120 |
| catatgcttc tgtggacagc tgtgctattc ctggctcctg ttgctgggac acctgcagct | 180 |
| cccccaaagg ctgtgctgaa actcgagccc cagtggatca acgtgctcca ggaggactct | 240 |
| gtgactctga catgccgggg gactcacagc cctgagagcg actccattca gtggttccac | 300 |
| aatgggaatc tcattcccac ccacacgcag cccagctaca ggttcaaggc caacaacaat | 360 |
| gacagcgggg agtacacgtg ccagactggc cagaccagcc tcagcgaccc tgtgcatctg | 420 |
| actgtgcttt ctgagtggct ggtgctccag acccctcacc tggagttcca ggagggagaa | 480 |
| accatcgtgc tgaggtgcca cagctggaag gacaagcctc tggtcaaggt cacattcttc | 540 |
| cagaatggaa aatccaagaa atttcccgt tcggatccca acttctccat cccacaagca | 600 |
| aaccacagtc acagtggtga ttaccactgc acaggaaaca taggctacac gctgtactca | 660 |
| tccaagcctg tgaccatcac tgtccaagct cccagctctt caccgatggg gatcattgtg | 720 |
| gctgtggtca ctgggattgc tgtagcggcc attgttgctg ctgtagtggc cttgatctac | 780 |
| tgcaggaaaa agcggatttc agccaatccc actaatcctg atgaggctga caaagttggg | 840 |
| gctgagaaca caatcaccta ttcacttctc atgcacccgg atgctctgga agagcctgat | 900 |
| gaccagaacc gtatttagtc tccattgtct tgcattggga tttgagaaga aaatcagaga | 960 |
| gggaagatct ggtatttcct ggcctaaatt cccttgggg aggacaggga gatgctgcag | 1020 |
| ttccaaaaga gaaggtttct tccagagtca tctacctgag tcctgaagct ccctgtcctg | 1080 |
| aaagccacag acaatatggt cccaaataac cgactgcacc ttctgtgctt cagctcttct | 1140 |
| tgacatcaag gctcttccgt tccacatcca cacagccaat ccaattaatc aaaccactgt | 1200 |
| tattaacaga taatagcaac ttgggaaatg cttatgttac aggttacgtg agaacaatca | 1260 |
| tgtaaatcta tatgatttca gaaatgttaa aatagactaa cctctaccag cacattaaaa | 1320 |
| gtgattgttt ctgggtgata aaattattga tgattttat tttctttatt tttctataaa | 1380 |
| gatcatatat tacttttata ataaacatt ataaaacaa aaaaaaaaa aaaaaaaaa | 1440 |
| aaaaaaaaaa aaaaaaaaaa aaaaaaaaaa aaaaaaaaaa aaaaaaaaaa aaaaaaa | 1497 |

<210> SEQ ID NO 6
<211> LENGTH: 291
<212> TYPE: PRT
<213> ORGANISM: Homo sapiens

<400> SEQUENCE: 6

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110
```

```
Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
        130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 7
<211> LENGTH: 2137
<212> TYPE: DNA
<213> ORGANISM: Homo sapiens

<400> SEQUENCE: 7
cttgtccact ccagtgtggc atcatgtggc agctgctcct cccaactgct ctgctacttc      60
tagtttcagc tggcatgcgg actgaagatc tcccaaaggc tgtggtgttc ctggagcctc     120
aatggtacag ggtgctcgag aaggacagtg tgactctgaa gtgccaggga gcctactccc     180
ctgaggacaa ttccacacag tggtttcaca atgagagcct catctcaagc caggcctcga     240
gctacttcat tgacgctgcc acagttgacg acagtggaga gtacaggtgc cagacaaacc     300
tctccaccct cagtgacccg gtgcagctag aagtccatat cggctggctg ttgctccagg     360
cccctcggtg ggtgttcaag gaggaagacc ctattcacct gaggtgtcac agctggaaga     420
acactgctct gcataaggtc acatatttac agaatggcaa aggcaggaag tattttcatc     480
ataattctga cttctacatt ccaaaagcca cactcaaaga cagcggctcc tacttctgca     540
gggggcttgt tgggagtaaa aatgtgtctt cagagactgt gaacatcacc atcactcaag     600
gtttgtcagt gtcaaccatc tcatcattct ttccacctgg gtaccaagtc tcttctgct      660 tggtgatggt actcctttt gcagtggaca caggactata tttctctgtg aagacaaaca     720
ttcgaagctc aacaagagac tggaaggacc ataaatttaa atggagaaag gaccctcaag     780
acaaatgacc cccatcccat gggggtaata agagcagtag cagcagcatc tctgaacatt     840
tctctggatt tgcaacccca tcatcctcag gcctctctac aagcagcagg aaacatagaa     900
ctcagagcca gatcccttat ccaactctcg acttttcctt ggtctccagt ggaagggaaa     960
agcccatgat cttcaagcag ggaagcccca gtgagtagct gcattcctag aaattgaagt    1020
ttcagagcta cacaaacact ttttctgtcc caaccgttcc ctcacagcaa agcaacaata    1080
```

-continued

```
caggctaggg atggtaatcc tttaaacata caaaaattgc tcgtgttata aattacccag    1140
tttagagggg aaaaaaaaac aattattcct aaataaatgg ataagtagaa ttaatggttg    1200
aggcaggacc atacagagtg tgggaactgc tggggatcta gggaattcag tgggaccaat    1260
gaaagcatgg ctgagaaata gcaggtagtc caggatagtc taagggaggt gttcccatct    1320
gagcccagag ataagggtgt cttcctagaa cattagccgt agtggaatta acaggaaatc    1380
atgagggtga cgtagaattg agtcttccag gggactctat cagaactgga ccatctccaa    1440
gtatataacg atgagtcctc ttaatgctag gagtagaaaa tggtcctagg aaggggactg    1500
aggattgcgg tggggggtgg ggtggaaaag aaagtacaga acaaaccctg tgtcactgtc    1560
ccaagttgct aagtgaacag aactatctca gcatcagaat gagaaagcct gagaagaaag    1620
aaccaaccac aagcacacag gaaggaaagc gcaggaggtg aaaatgcttt cttggccagg    1680
gtagtaagaa ttagaggtta atgcagggac tgtaaaacca cctttctgc ttcaatatct    1740 aattcctgtg tagctttgtt cattgcattt attaaacaaa tgttgtataa ccaatactaa    1800
atgtactact gagcttcgct gagttaagtt atgaaacttt caaatccttc atcatgtcag    1860
ttccaatgag gtggggatgg agaagacaat tgttgcttat gaaagaaagc tttagctgtc    1920
tctgttttgt aagctttaag cgcaacattt cttggttcca ataaagcatt ttacaagatc    1980
ttgcatgcta ctcttagata gaagatggga aaaccatggt aataaaatat gaatgataaa    2040
aaaaaaaaaa aaaaaaaaaa aaaaaaaaaa aaaaaaaaa aaaaaaaaaa aaaaaaaaa    2100 aaaaaaaaaa aaaaaaaaaa aaaaaaaaaa aaaaaaa                              2137
```

<210> SEQ ID NO 8
<211> LENGTH: 254
<212> TYPE: PRT
<213> ORGANISM: Homo sapiens

<400> SEQUENCE: 8

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
```

```
            180                 185                 190
Gly Leu Ser Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

```
<210> SEQ ID NO 9
<211> LENGTH: 820
<212> TYPE: DNA
<213> ORGANISM: Homo sapiens

<400> SEQUENCE: 9
cactccagtg tggcatcatg tggcagctgc tcctcccaac tgctctgcta cttctagttt      60
cagctggcat gcggactgaa gatctcccaa aggctgtggt gttcctggag cctcaatggt     120
acagcgtgct tgagaaggac agtgtgactc tgaagtgcca gggagcctac tcccctgagg     180
acaattccac acagtggttt cacaatgaga gcctcatctc aagccaggcc tcgagctact     240
tcattgacgc tgccacagtc aacgacagtg gagagtacag gtgccagaca aacctctcca     300
ccctcagtga cccggtgcag ctagaagtcc atatcggctg gctgttgctc aggcccctc     360 ggtgggtgtt caaggaggaa gaccctattc acctgaggtg tcacagctgg aagaacactg     420
ctctgcataa ggtcacatat ttacagaatg caaagacag gaagtatttt catcataatt     480
ctgacttcca cattccaaaa gccacactca agatagcgg ctcctacttc tgcaggggc     540 ttgttgggag taaaaatgtg tcttcagaga ctgtgaacat caccatcact caaggtttgg     600
cagtgtcaac catctcatca ttctctccac ctgggtacca agtctctttc tgcttggtga     660
tggtactcct ttttgcagtg gacacaggac tatatttctc tgtgaagaca aacatttgaa     720
gctcaacaag agactggaag gaccataaac ttaaatggag aaaggaccct caagacaaat     780
gacccccatc ccatgggagt aataagagca gtggcagcag                           820
```

```
<210> SEQ ID NO 10
<211> LENGTH: 233
<212> TYPE: PRT
<213> ORGANISM: Homo sapiens

<400> SEQUENCE: 10

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110
```

```
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 11
<211> LENGTH: 330
<212> TYPE: PRT
<213> ORGANISM: Artificial Sequence
<220> FEATURE:
<223> OTHER INFORMATION: an artificially synthesized sequence

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 326
<212> TYPE: PRT
<213> ORGANISM: Artificial Sequence
<220> FEATURE:
<223> OTHER INFORMATION: an artificially synthesized sequence

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 13
<211> LENGTH: 377
<212> TYPE: PRT
<213> ORGANISM: Artificial Sequence
<220> FEATURE:
<223> OTHER INFORMATION: an artificially synthesized sequence

<400> SEQUENCE: 13

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 14
<211> LENGTH: 327
<212> TYPE: PRT
<213> ORGANISM: Artificial Sequence
<220> FEATURE:
<223> OTHER INFORMATION: an artificially synthesized sequence

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

```
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro
            325

<210> SEQ ID NO 16
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
            325

<210> SEQ ID NO 17
<211> LENGTH: 115

```
<212> TYPE: PRT
<213> ORGANISM: Artificial Sequence
<220> FEATURE:
<223> OTHER INFORMATION: an artificially synthesized sequence

<400> SEQUENCE: 17

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

<210> SEQ ID NO 19
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
         50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                 85                  90                  95
Pro Val Thr Lys Ser Phe Asn Arg Gly Glu Cys
            100                 105
```

<210> SEQ ID NO 20
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 20

```
Gln Val Gln Leu Gln Glu Ser Gly Pro Gly Leu Val Arg Pro Ser Gln
  1               5                  10                  15
Thr Leu Ser Leu Thr Cys Thr Val Ser Gly Tyr Ser Ile Thr Ser Asp
             20                  25                  30
His Ala Trp Ser Trp Val Arg Gln Pro Pro Gly Arg Gly Leu Glu Trp
         35                  40                  45
Ile Gly Tyr Ile Ser Tyr Ser Gly Ile Thr Thr Tyr Asn Pro Ser Leu
     50                  55                  60
Lys Ser Arg Val Thr Met Leu Arg Asp Thr Ser Lys Asn Gln Phe Ser
 65                  70                  75                  80
Leu Arg Leu Ser Ser Val Thr Ala Ala Asp Thr Ala Val Tyr Tyr Cys
                 85                  90                  95
Ala Arg Ser Leu Ala Arg Thr Thr Ala Met Asp Tyr Trp Gly Gln Gly
            100                 105                 110
Ser Leu Val Thr Val Ser Ser
        115
```

<210> SEQ ID NO 21
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 21

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Asp Ile Ser Ser Tyr
             20                  25                  30
Leu Asn Trp Tyr Gln Gln Lys Pro Gly Lys Ala Pro Lys Leu Leu Ile
         35                  40                  45
Tyr Tyr Thr Ser Arg Leu His Ser Gly Val Pro Ser Arg Phe Ser Gly
     50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Gly Asn Thr Leu Pro Tyr
                 85                  90                  95
Thr Phe Gly Gln Gly Thr Lys Val Glu Ile Lys
            100                 105
```

```
<210> SEQ ID NO 22
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 22
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Thr | Val | Ser | Cys | Lys | Ala | Ser | Gly | Tyr | Thr | Phe | Thr | Asp | Tyr |
| | | | 20 | | | | | 25 | | | | | 30 | | |
| Glu | Met | His | Trp | Ile | Arg | Gln | Pro | Pro | Gly | Glu | Gly | Leu | Glu | Trp | Ile |
| | | 35 | | | | | 40 | | | | | 45 | | | |
| Gly | Ala | Ile | Asp | Pro | Lys | Thr | Gly | Asp | Thr | Ala | Tyr | Ser | Glu | Ser | Phe |
| 50 | | | | | 55 | | | | | 60 | | | | | |
| Gln | Asp | Arg | Val | Thr | Leu | Thr | Ala | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Thr | Ser | Glu | Asp | Thr | Ala | Val | Tyr | Tyr | Cys |
| | | | | 85 | | | | | 90 | | | | | 95 | |
| Thr | Arg | Phe | Tyr | Ser | Tyr | Thr | Tyr | Trp | Gly | Gln | Gly | Thr | Leu | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Ser | Ser | Lys | Ser | Thr | Ser | Gly | Gly | Thr | Ala | Ala | Leu | Gly | Cys | Leu | Val |
| 130 | | | | | 135 | | | | | 140 | | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Gln | Thr | Tyr | Ile | Cys | Asn | Val | Asn | His | Lys | Pro | Ser | Asn | Thr | Lys |
| | | 195 | | | | | 200 | | | | | 205 | | | |
| Val | Asp | Lys | Lys | Val | Glu | Pro | Lys | Ser | Cys | Asp | Lys | Thr | His | Thr | Cys |
| 210 | | | | | 215 | | | | | 220 | | | | | |
| Pro | Pro | Cys | Pro | Ala | Pro | Glu | Leu | Leu | Gly | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Val | Asp | Val | Ser | His | Glu | Asp | Pro | Glu | Val | Lys |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Tyr | Asn | Ser | Thr | Tyr | Arg | Val | Val | Ser | Val | Leu |
| 290 | | | | | 295 | | | | | 300 | | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Ala | Leu | Pro | Ala | Pro | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Arg | Asp | Glu | Leu | Thr | Lys | Asn | Gln | Val | Ser | Leu | Thr | Cys | Leu | Val | Lys |
| | | 355 | | | | | 360 | | | | | 365 | | | |

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
                435                 440

<210> SEQ ID NO 23
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 23

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290             295                 300

Val Ser Val Leu Thr Val Leu His Gln Asp Trp Leu Asn Gly Lys Glu
305             310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 24
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Cys Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

Lys Ala Leu Pro Ala Pro Ile Glu Cys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 25
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Cys Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Cys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 26
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ile Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 27
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Ile Ser Gln Asp Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 28
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

```
<210> SEQ ID NO 29
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Tyr Asn Ser Thr Glu Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 30
<211> LENGTH: 328
<212> TYPE: PRT
<213> ORGANISM: Artificial Sequence
<220> FEATURE:
```

<223> OTHER INFORMATION: an artificially synthesized sequence

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 31
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 31

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Ser Ala Leu Pro His Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 32
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val His Asn
        195                 200                 205

Ser Ala Leu Pro His Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 33
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ala Ala Leu Pro Tyr Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 34
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

```
Pro Ala Pro Glu Lys Lys Gly Gly Pro Ser Val Phe Leu Phe Pro Pro
            115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325
```

<210> SEQ ID NO 35
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 35

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Lys Arg Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 36
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Arg Lys Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 37
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Arg Arg Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 38
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Pro Met Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 39
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 39

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Met Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 40
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 41
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

```
<210> SEQ ID NO 42
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 43
<211> LENGTH: 328
<212> TYPE: PRT
<213> ORGANISM: Artificial Sequence
```

```
<220> FEATURE:
<223> OTHER INFORMATION: an artificially synthesized sequence

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Met
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 44
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 44

Ala Ser Thr Lys Gly Pro Ser Val Phe Pro Leu Ala Pro Ser Ser Lys
```

```
              1               5                  10                 15
            Ser Thr Ser Gly Gly Thr Ala Ala Leu Gly Cys Leu Val Lys Asp Tyr
                        20                  25                 30

Phe Pro Glu Pro Val Thr Val Ser Trp Asn Ser Gly Ala Leu Thr Ser
                        35                  40                 45

Gly Val His Thr Phe Pro Ala Val Leu Gln Ser Ser Gly Leu Tyr Ser
                        50                  55                 60

Leu Ser Ser Val Val Thr Val Pro Ser Ser Leu Gly Thr Gln Thr
             65                 70                  75                  80

Tyr Ile Cys Asn Val Asn His Lys Pro Ser Asn Thr Lys Val Asp Lys
                            85                  90                 95

Lys Val Glu Pro Lys Ser Cys Asp Lys Thr His Thr Cys Pro Pro Cys
                        100                 105                110

Pro Ala Pro Glu Leu Leu Gly Gly Pro Lys Val Phe Leu Phe Pro Pro
                        115                 120                125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
            145                 150                 155                160

Tyr Val Asp Gly Val Glu Val His Asn Ala Lys Thr Lys Pro Arg Glu
                            165                 170                175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser His
                        195                 200                 205

Lys Ala Leu Pro Ala Pro Ile Glu Lys Thr Ile Ser Lys Ala Lys Gly
                        210                 215                 220

Gln Pro Arg Glu Pro Gln Val Tyr Thr Leu Pro Pro Ser Arg Asp Glu
            225                 230                 235                240

Leu Thr Lys Asn Gln Val Ser Leu Thr Cys Leu Val Lys Gly Phe Tyr
                            245                 250                255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                        290                 295                 300

Val Phe Ser Cys Ser Val Met His Glu Ala Leu His Asn His Tyr Thr
            305                 310                 315                320

Gln Lys Ser Leu Ser Leu Ser Pro
                        325

<210> SEQ ID NO 45
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 45

Ala Ser Thr Lys Gly Pro Ser Val Phe Pro Leu Ala Pro Ser Ser Lys
            1               5                   10                 15

Ser Thr Ser Gly Gly Thr Ala Ala Leu Gly Cys Leu Val Lys Asp Tyr
                        20                  25                 30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ser Ala Leu Pro His Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 46
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Met Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Ala Ala Leu Pro Tyr Pro Ile Glu Lys Thr Ile Ser Lys Ala Lys Gly
                210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 47
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 47

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
```

-continued

```
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Leu Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Ser Ala Leu Pro His Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325
```

<210> SEQ ID NO 48
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 48

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Ala Ala Leu Pro Tyr Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 49
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                        165                 170                 175
Glu Met Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                195                 200                 205

Ser Ala Leu Pro Tyr Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 50
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Ala Ala Leu Pro His Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 51
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Ser Ala Leu Pro Tyr Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 52
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Ala Ala Leu Pro His Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro
                325
```

<210> SEQ ID NO 53
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 53

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Lys Lys Gly Gly Pro Lys Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser Lys Glu Phe Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Met Gly Asn Gly Thr Tyr Arg Val Val Ser Val Leu Thr Val Leu
            180                 185                 190
His Gln Asp Trp Leu Asn Gly Lys Glu Tyr Lys Cys Lys Val Ser Gly
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 54
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Lys Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 55
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Lys Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 56
<211> LENGTH: 328
<212> TYPE: PRT

<213> ORGANISM: Artificial Sequence
<220> FEATURE:
<223> OTHER INFORMATION: an artificially synthesized sequence

<400> SEQUENCE: 56

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Lys Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 57
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 57

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Lys Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 58
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Lys Lys Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 59
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Lys Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 60
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Lys Lys Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 61
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Lys Val Phe Leu Phe Pro Pro
            115                 120                 125
```

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
                180                 185                 190

His Gln Asp Trp Leu Asn Gly Lys Glu Tyr Lys Cys Lys Val Ser Gly
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 62
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 63
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Lys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
              195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 64
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Lys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 65
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 66
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Lys Glu Phe Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 67
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser Gly
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320
```

Gln Lys Ser Leu Ser Leu Ser Pro
            325

<210> SEQ ID NO 68
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Lys Arg Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Met Gly Asn Gly Thr Tyr Arg Val Val Ser Val Leu Thr Val Leu
            180                 185                 190

His Gln Asp Trp Leu Asn Gly Lys Glu Tyr Lys Cys Lys Val Ser His
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 69
<211> LENGTH: 328

<212> TYPE: PRT
<213> ORGANISM: Artificial Sequence
<220> FEATURE:
<223> OTHER INFORMATION: an artificially synthesized sequence

<400> SEQUENCE: 69

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Val Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 70
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Phe Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 71
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Ile Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 72
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Met Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 73
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Val Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 74
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Trp Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 75
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Tyr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 76
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Gly Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 77
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Ala Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 78
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 79
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 80
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Ala
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 81
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Asp
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 82

```
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Arg
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 83
<211> LENGTH: 328
<212> TYPE: PRT
<213> ORGANISM: Artificial Sequence
<220> FEATURE:
<223> OTHER INFORMATION: an artificially synthesized sequence
```

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Pro
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 84
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                20              25              30
Phe Pro Glu Pro Val Thr Val Ser Trp Asn Ser Gly Ala Leu Thr Ser
            35              40              45
Gly Val His Thr Phe Pro Ala Val Leu Gln Ser Ser Gly Leu Tyr Ser
        50              55              60
Leu Ser Ser Val Val Thr Val Pro Ser Ser Ser Leu Gly Thr Gln Thr
65              70              75              80
Tyr Ile Cys Asn Val Asn His Lys Pro Ser Asn Thr Lys Val Asp Lys
                85              90              95
Lys Val Glu Pro Lys Ser Cys Asp Lys Thr His Thr Cys Pro Pro Cys
            100             105             110
Pro Ala Pro Glu Leu Leu Gly Gly Pro Ser Val Phe Leu Phe Pro Pro
        115             120             125
Lys Pro Lys Asp Thr Leu Met Ile Ser Arg Thr Pro Glu Val Thr Cys
    130             135             140
Val Val Val Asp Val Ser His Glu Asp Pro Glu Val Lys Phe Asn Trp
145             150             155             160
Tyr Val Asp Gly Val Glu Val His Asn Ala Lys Thr Lys Pro Arg Glu
                165             170             175
Glu Gln Tyr Asn Ser Thr Tyr Arg Val Val Ser Val Leu Thr Val Leu
            180             185             190
His Gln Asp Trp Leu Ala Gly Lys Glu Tyr Lys Cys Lys Val Ser Asn
        195             200             205
Lys Ala Leu Pro Ala Pro Ile Glu Lys Thr Ile Ser Lys Ala Lys Gly
    210             215             220
Gln Pro Arg Glu Pro Gln Val Tyr Thr Leu Pro Pro Ser Arg Asp Glu
225             230             235             240
Leu Thr Lys Asn Gln Val Ser Leu Thr Cys Leu Val Lys Gly Phe Tyr
                245             250             255
Pro Ser Asp Ile Ala Val Glu Trp Glu Ser Asn Gly Gln Pro Glu Asn
            260             265             270
Asn Tyr Lys Thr Thr Pro Pro Val Leu Asp Ser Asp Gly Ser Phe Phe
        275             280             285
Leu Tyr Ser Lys Leu Thr Val Asp Lys Ser Arg Trp Gln Gln Gly Asn
    290             295             300
Val Phe Ser Cys Ser Val Met His Glu Ala Leu His Asn His Tyr Thr
305             310             315             320
Gln Lys Ser Leu Ser Leu Ser Pro
                325

<210> SEQ ID NO 85
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 85

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr His Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 86
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 86

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Asp Pro Pro Glu Ser
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 87
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 87

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Glu Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 88
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
            145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val His His Glu Ala Leu His Asn His Tyr Thr
305                 310                 315                 320

Gln Lys Ser Leu Ser Leu Ser Pro
                325

<210> SEQ ID NO 89
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                180             185             190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Trp His Glu Ala Leu His Asn His Tyr Thr
305                 310                 315                 320

Gln Lys Ser Leu Ser Leu Ser Pro
                325
```

<210> SEQ ID NO 90
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 90

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Tyr His Glu Ala Leu His Asn His Tyr Thr
305                 310                 315                 320

Gln Lys Ser Leu Ser Leu Ser Pro
                325

<210> SEQ ID NO 91
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Phe His Glu Ala Leu His Asn His Tyr Thr
305                 310                 315                 320

Gln Lys Ser Leu Ser Leu Ser Pro
                325

<210> SEQ ID NO 92
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
              275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu Lys Asn His Tyr Thr
305                 310                 315                 320

Gln Lys Ser Leu Ser Leu Ser Pro
                325
```